US010363103B2

(12) United States Patent
Alvarez et al.

(10) Patent No.: US 10,363,103 B2
(45) Date of Patent: *Jul. 30, 2019

(54) FLEXIBLE AND STEERABLE ELONGATE INSTRUMENTS WITH SHAPE CONTROL AND SUPPORT ELEMENTS

(71) Applicant: Auris Health, Inc., Redwood City, CA (US)

(72) Inventors: Jeffery B. Alvarez, San Mateo, CA (US); Enrique Romo, Dublin, CA (US); Francis MacNamara, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 605 days.

This patent is subject to a terminal disclaimer.

(21) Appl. No.: 15/017,147

(22) Filed: Feb. 5, 2016

(65) Prior Publication Data
US 2016/0151122 A1 Jun. 2, 2016

Related U.S. Application Data

(63) Continuation of application No. 12/432,683, filed on Apr. 29, 2009, now Pat. No. 9,254,123.

(51) Int. Cl.
*A61B 1/00* (2006.01)
*A61M 25/01* (2006.01)
(Continued)

(52) U.S. Cl.
CPC ............ *A61B 34/30* (2016.02); *A61B 1/0055* (2013.01); *A61B 1/0057* (2013.01);
(Continued)

(58) Field of Classification Search
CPC .......... A61M 25/0136; A61M 25/0147; A61M 2025/0062; A61M 2025/0161;
(Continued)

(56) References Cited

U.S. PATENT DOCUMENTS 3,572,325 A 3/1971 Bazell et al.
4,741,326 A 5/1988 Sidall et al.
(Continued)

FOREIGN PATENT DOCUMENTS

CA 2285342 A1 10/1998
CN 101500470 8/2009
(Continued)

OTHER PUBLICATIONS

PCT International Search Report for International Patent Application No. PCT/US2005/007108, dated Jun. 27, 2005 (4 pages).
(Continued)

*Primary Examiner* — Rebecca E Eisenberg
(74) *Attorney, Agent, or Firm* — Knobbe, Martens, Olson & Bear, LLP

(57) ABSTRACT

An instrument having a flexible and elongated body includes at least a lumen and a flex member disposed within the lumen. The flex member may be capable of providing steering control to a first portion of the elongate body while providing load bearing support to a second portion of the elongate body. A pull wire may be disposed within the flex member, and at least a distal portion of the pull wire may be coupled to the elongate body and a proximal portion of the pull wire may be operatively coupled to a control unit. The control unit may be coupled to a proximal portion of the elongate body. In addition, a control member may be operatively coupled to the control unit such that a distal portion of the control member may be positioned near a proximal portion of the flex member. The control member may be configured to support the flex member and control the movement or displacement of the flex member. Furthermore, the flex member may be configured to selectively decouple articulation or steering forces of a first portion of the elongate body away from a second portion of the elongate
(Continued)

body; thereby, preventing compression of the second portion of the elongate body while maintaining elasticity or flexibility of the second portion of the elongate body.

20 Claims, 40 Drawing Sheets

(51) Int. Cl.
*A61B 34/30* (2016.01)
*A61B 17/00* (2006.01)
*A61B 1/005* (2006.01)
*A61B 34/00* (2016.01)

(52) U.S. Cl.
CPC .... *A61B 1/00078* (2013.01); *A61B 17/00234* (2013.01); *A61B 34/71* (2016.02); *A61M 25/0136* (2013.01); *A61M 25/0138* (2013.01); *A61M 25/0144* (2013.01); *A61M 25/0147* (2013.01); *A61B 2017/00318* (2013.01); *A61B 2017/00327* (2013.01); *A61B 2034/301* (2016.02); *A61B 2034/303* (2016.02); *A61M 2025/015* (2013.01); *A61M 2025/0161* (2013.01)

(58) Field of Classification Search
CPC .... A61B 2017/003; A61B 2017/00318; A61B 2017/00323; A61B 2017/00327
See application file for complete search history.

(56) References Cited

U.S. PATENT DOCUMENTS

| | | |
|---|---|---|
| 4,745,903 A | 5/1988 | Wardle |
| 4,748,969 A | 6/1988 | Wardle |
| 4,869,238 A | 9/1989 | Opie et al. |
| 4,907,168 A | 3/1990 | Boggs |
| 4,925,445 A | 5/1990 | Sakamoto et al. |
| 4,945,305 A | 7/1990 | Blood |
| 4,967,732 A | 11/1990 | Inoue |
| 5,078,714 A | 1/1992 | Katims |
| 5,106,387 A | 4/1992 | Kittrell et al. |
| 5,168,864 A | 12/1992 | Shockey |
| 5,287,861 A | 2/1994 | Wilk |
| 5,313,934 A | 5/1994 | Wiita et al. |
| 5,339,799 A | 8/1994 | Kami et al. |
| 5,341,807 A | 8/1994 | Nardella |
| 5,368,015 A | 11/1994 | Wilk |
| 5,394,875 A | 3/1995 | Lewis et al. |
| 5,397,443 A | 3/1995 | Michaels |
| 5,398,691 A | 3/1995 | Martin et al. |
| 5,408,409 A | 4/1995 | Glassman et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,507,725 A | 4/1996 | Savage et al. |
| 5,531,664 A | 7/1996 | Adachi et al. |
| 5,580,200 A | 12/1996 | Fullerton |
| 5,600,330 A | 2/1997 | Blood |
| 5,631,973 A | 5/1997 | Green |
| 5,662,108 A | 9/1997 | Budd et al. |
| 5,673,704 A | 10/1997 | Marchlinski et al. |
| 5,697,377 A | 12/1997 | Wittkampf |
| 5,704,534 A | 1/1998 | Huitema et al. |
| 5,713,946 A | 2/1998 | Ben-Haim |
| 5,733,245 A | 3/1998 | Kawano |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,784,542 A | 7/1998 | Ohm et al. |
| 5,799,055 A | 8/1998 | Peshkin et al. |
| 5,815,640 A | 9/1998 | Wang et al. |
| 5,825,982 A | 10/1998 | Wright et al. |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,843,076 A | 12/1998 | Webster, Jr. et al. |
| 5,873,817 A | 2/1999 | Kokish et al. |
| 5,876,325 A | 3/1999 | Mizuno et al. |
| 5,878,193 A | 3/1999 | Wang et al. |
| 5,891,095 A | 4/1999 | Eggers et al. |
| 5,910,129 A | 6/1999 | Koblish et al. |
| 5,925,078 A | 7/1999 | Anderson |
| 5,935,079 A | 8/1999 | Swanson et al. |
| 5,950,629 A | 9/1999 | Taylor et al. |
| 5,953,683 A | 9/1999 | Hansen et al. |
| 5,983,126 A | 11/1999 | Wittkampf |
| 6,004,271 A | 12/1999 | Moore |
| 6,012,494 A | 1/2000 | Balazs |
| 6,063,022 A | 5/2000 | Ben-Haim |
| 6,063,095 A | 5/2000 | Wang et al. |
| 6,080,181 A | 6/2000 | Jensen et al. |
| 6,083,170 A | 7/2000 | Ben-Haim |
| 6,096,004 A | 8/2000 | Meglan et al. |
| 6,106,511 A | 8/2000 | Jensen |
| 6,129,668 A | 10/2000 | Haynor et al. |
| 6,132,368 A | 10/2000 | Cooper |
| 6,157,853 A | 12/2000 | Blume et al. |
| 6,161,032 A | 12/2000 | Acker |
| 6,172,499 B1 | 1/2001 | Ashe |
| 6,198,974 B1 | 3/2001 | Webster, Jr. |
| 6,203,493 B1 | 3/2001 | Ben-Haim |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,504 B1 | 5/2001 | Das et al. |
| 6,246,200 B1 | 6/2001 | Blumenkranz et al. |
| 6,266,551 B1 | 7/2001 | Osadchy et al. |
| 6,272,371 B1 | 8/2001 | Shlomo |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,315,715 B1 | 11/2001 | Taylor et al. |
| 6,331,181 B1 | 12/2001 | Tierney et al. |
| 6,363,279 B1 | 3/2002 | Ben-Haim et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,393,340 B2 | 5/2002 | Funda et al. |
| 6,398,731 B1 | 6/2002 | Mumm et al. |
| 6,400,979 B1 | 6/2002 | Stoianovici et al. |
| 6,415,171 B1 | 7/2002 | Gueziec et al. |
| 6,424,885 B1 | 7/2002 | Niemeyer et al. |
| 6,436,107 B1 | 8/2002 | Wang et al. |
| 6,491,626 B1 | 12/2002 | Stone et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,530,913 B1 | 3/2003 | Giba et al. |
| 6,544,230 B1 | 4/2003 | Flaherty et al. |
| 6,554,793 B1 | 4/2003 | Pauker et al. |
| 6,565,554 B1 | 5/2003 | Niemeyer |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,669,709 B1 | 12/2003 | Cohn et al. |
| 6,685,698 B2 | 2/2004 | Morley et al. |
| 6,699,235 B2 | 3/2004 | Wallace et al. |
| 6,716,166 B2 | 4/2004 | Govari |
| 6,716,178 B1 | 4/2004 | Kilpatrick et al. |

(56) References Cited

U.S. PATENT DOCUMENTS

| | | |
|---|---|---|
| 6,726,675 B1 | 4/2004 | Beyar |
| 6,774,624 B2 | 8/2004 | Anderson et al. |
| 6,783,524 B2 | 8/2004 | Anderson et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,963,792 B1 | 11/2005 | Green |
| 7,008,401 B2 | 3/2006 | Thompson et al. |
| 7,021,173 B2 | 4/2006 | Stoianovici et al. |
| 7,074,179 B2 | 7/2006 | Wang et al. |
| 7,087,049 B2 | 8/2006 | Nowlin et al. |
| 7,130,700 B2 | 10/2006 | Gardeski et al. |
| 7,169,141 B2 | 1/2007 | Brock et al. |
| 7,192,438 B2 | 3/2007 | Margolis |
| 7,225,012 B1 | 5/2007 | Susil et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock et al. |
| 7,494,494 B2 | 2/2009 | Stoianovici et al. |
| 7,569,052 B2 | 8/2009 | Phan et al. |
| 7,850,642 B2 | 12/2010 | Moll et al. |
| 7,930,065 B2 | 4/2011 | Larkin et al. |
| 7,963,288 B2 | 6/2011 | Rosenberg et al. |
| 7,972,298 B2 | 7/2011 | Wallace et al. |
| 8,052,636 B2 | 11/2011 | Moll et al. |
| 8,092,397 B2 | 1/2012 | Wallace et al. |
| 8,190,238 B2 | 5/2012 | Moll et al. |
| 8,391,957 B2 | 3/2013 | Carlson et al. |
| 8,444,637 B2 | 5/2013 | Podmore et al. |
| 8,498,691 B2 | 7/2013 | Moll et al. |
| 8,515,215 B2 | 8/2013 | Younge et al. |
| 8,602,031 B2 | 12/2013 | Reis et al. |
| 8,720,448 B2 | 5/2014 | Reis et al. |
| 8,827,947 B2 | 9/2014 | Bosman et al. |
| 8,827,948 B2 | 9/2014 | Romo et al. |
| 8,894,610 B2 | 11/2014 | MacNamara et al. |
| 8,961,533 B2 | 2/2015 | Stahler et al. |
| 9,138,166 B2 | 9/2015 | Wong et al. |
| 9,173,713 B2 | 11/2015 | Hart et al. |
| 9,186,046 B2 | 11/2015 | Ramamurthy et al. |
| 9,204,933 B2 | 12/2015 | Reis et al. |
| 9,254,123 B2 | 2/2016 | Alvarez et al. |
| 9,408,669 B2 | 8/2016 | Kokish et al. |
| 9,427,551 B2 | 8/2016 | Leeflang et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 2001/0000040 A1 | 3/2001 | Adams et al. |
| 2001/0009976 A1 | 7/2001 | Panescu et al. |
| 2001/0029366 A1 | 10/2001 | Swanson et al. |
| 2002/0087169 A1 | 7/2002 | Brock et al. |
| 2002/0156369 A1 | 10/2002 | Chakeres |
| 2002/0177789 A1 | 11/2002 | Ferry et al. |
| 2003/0074011 A1 | 4/2003 | Gilboa et al. |
| 2003/0109780 A1 | 6/2003 | Goste-Maniere et al. |
| 2003/0135204 A1 | 7/2003 | Lee et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0034282 A1 | 2/2004 | Quaid, III |
| 2004/0034365 A1 | 2/2004 | Lentz et al. |
| 2004/0138525 A1 | 7/2004 | Saadat et al. |
| 2004/0176751 A1 | 9/2004 | Weitzner et al. |
| 2004/0193146 A1 | 9/2004 | Lee et al. |
| 2005/0004515 A1 | 1/2005 | Hart et al. |
| 2005/0059960 A1 | 3/2005 | Simaan et al. |
| 2005/0070844 A1 | 3/2005 | Chow et al. |
| 2005/0125005 A1 | 6/2005 | Fujikura |
| 2005/0131343 A1 | 6/2005 | Abrams et al. |
| 2005/0131460 A1 | 6/2005 | Gifford, III et al. |
| 2005/0154262 A1 | 7/2005 | Banik et al. |
| 2005/0159646 A1 | 7/2005 | Nordstrom et al. |
| 2005/0165276 A1 | 7/2005 | Belson et al. |
| 2005/0182295 A1 | 8/2005 | Soper et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2005/0272975 A1 | 12/2005 | McWeeney et al. |
| 2005/0288549 A1 | 12/2005 | Mathis |
| 2006/0013523 A1 | 1/2006 | Childers et al. |
| 2006/0041188 A1 | 2/2006 | Dirusso et al. |
| 2006/0058647 A1 | 3/2006 | Strommer et al. |
| 2006/0111692 A1 | 5/2006 | Hlavka et al. |
| 2006/0178556 A1 | 8/2006 | Hasser et al. |
| 2006/0200049 A1 | 9/2006 | Leo et al. |
| 2006/0264708 A1 | 11/2006 | Horne |
| 2006/0276775 A1 | 12/2006 | Rosenberg et al. |
| 2006/0276827 A1 | 12/2006 | Mitelberg et al. |
| 2007/0016130 A1 | 1/2007 | Leeflang et al. |
| 2007/0043261 A1 | 2/2007 | Watanabe et al. |
| 2007/0043338 A1 | 2/2007 | Moll et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0112355 A1 | 5/2007 | Salahieh |
| 2007/0123851 A1 | 5/2007 | Alejandro et al. |
| 2007/0135733 A1 | 6/2007 | Soukup et al. |
| 2007/0135763 A1 | 6/2007 | Musbach et al. |
| 2007/0156123 A1 | 7/2007 | Moll et al. |
| 2007/0197896 A1 | 8/2007 | Moll et al. |
| 2007/0232858 A1 | 10/2007 | Macnamara et al. |
| 2007/0249901 A1 | 10/2007 | Ohline et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0287999 A1 | 12/2007 | Malecki et al. |
| 2007/0293724 A1 | 12/2007 | Saadat et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0033284 A1 | 2/2008 | Hauck |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0177285 A1 | 7/2008 | Brock et al. |
| 2008/0183071 A1 | 7/2008 | Strommer et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0255505 A1 | 10/2008 | Carlson et al. |
| 2008/0262480 A1 | 10/2008 | Stahler et al. |
| 2008/0281293 A1 | 11/2008 | Peh et al. |

(56) References Cited

U.S. PATENT DOCUMENTS

| | | |
|---|---|---|
| 2008/0300592 A1 | 12/2008 | Weitzner et al. |
| 2008/0319311 A1 | 12/2008 | Hamadeh |
| 2009/0024141 A1 | 1/2009 | Stahler et al. |
| 2009/0054884 A1 | 2/2009 | Farley et al. |
| 2009/0062602 A1 | 3/2009 | Rosenberg et al. |
| 2009/0099420 A1 | 4/2009 | Woodley et al. |
| 2009/0099554 A1 | 4/2009 | Forster et al. |
| 2009/0137952 A1 | 5/2009 | Ramamurthy et al. |
| 2009/0221908 A1 | 9/2009 | Glossop |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0318797 A1 | 12/2009 | Hadani |
| 2010/0030023 A1 | 2/2010 | Yoshie |
| 2010/0073150 A1 | 3/2010 | Olson et al. |
| 2010/0081920 A1 | 4/2010 | Whitmore, III et al. |
| 2010/0114115 A1 | 5/2010 | Schlesinger et al. |
| 2010/0130823 A1 | 5/2010 | Ando |
| 2010/0228191 A1 | 9/2010 | Alvarez et al. |
| 2010/0280320 A1 | 11/2010 | Alvarez et al. |
| 2010/0280449 A1 | 11/2010 | Alvarez et al. |
| 2010/0280525 A1 | 11/2010 | Alvarez et al. |
| 2010/0331856 A1 | 12/2010 | Carlson et al. |
| 2011/0015648 A1 | 1/2011 | Alvarez et al. |
| 2011/0152880 A1 | 1/2011 | Alvarez et al. |
| 2011/0046441 A1 | 2/2011 | Wiltshire et al. |
| 2011/0130718 A1 | 6/2011 | Kidd et al. |
| 2011/0261183 A1 | 10/2011 | Ma et al. |
| 2011/0306836 A1 | 12/2011 | Ohline et al. |
| 2012/0071822 A1 | 3/2012 | Romo et al. |
| 2012/0071894 A1 | 3/2012 | Tanner et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2013/0018400 A1 | 1/2013 | Milton et al. |
| 2013/0030363 A1 | 1/2013 | Wong et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0144116 A1 | 6/2013 | Cooper et al. |
| 2013/0165654 A1 | 6/2013 | Sandhu et al. |
| 2013/0165908 A1 | 6/2013 | Purdy et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012276 A1 | 1/2014 | Alvarez |
| 2014/0046313 A1 | 2/2014 | Pederson et al. |
| 2014/0069437 A1 | 3/2014 | Reis et al. |
| 2014/0142591 A1 | 5/2014 | Alvarez et al. |
| 2014/0200402 A1 | 7/2014 | Snoke et al. |
| 2014/0276391 A1 | 9/2014 | Yu |
| 2014/0276936 A1 | 9/2014 | Kokish et al. |
| 2014/0309649 A1 | 10/2014 | Alvarez et al. |
| 2014/0316397 A1 | 10/2014 | Brown |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0071684 A1 | 3/2017 | Kokish et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |

FOREIGN PATENT DOCUMENTS

| | | |
|---|---|---|
| CN | 102665590 | 9/2012 |
| EP | 0 543 539 | 5/1993 |
| EP | 0 776 739 | 6/1997 |
| EP | 0904796 A2 | 3/1999 |
| EP | 1 442 720 | 8/2004 |
| EP | 2204208 A2 | 7/2010 |
| JP | 2010-046384 | 3/2010 |
| JP | 2011-015992 | 1/2011 |
| WO | 9744089 A1 | 11/1997 |
| WO | 0011495 A1 | 3/2000 |
| WO | 0045193 A1 | 8/2000 |
| WO | WO 00/67640 | 11/2000 |
| WO | 0156457 A1 | 8/2001 |
| WO | WO 02/074178 | 9/2002 |
| WO | 03077769 A1 | 9/2003 |
| WO | 03091839 A2 | 11/2003 |
| WO | 2004039273 A2 | 5/2004 |
| WO | WO 04/105849 | 12/2004 |
| WO | 2005032637 A2 | 4/2005 |
| WO | 2005081202 A1 | 9/2005 |
| WO | WO 09/097461 | 6/2007 |
| WO | 2007149841 A2 | 12/2007 |
| WO | 20080033589 A1 | 3/2008 |
| WO | WO 08/097540 | 8/2008 |
| WO | WO 09/092059 | 7/2009 |
| WO | WO 10/088187 | 8/2010 |
| WO | 2010127162 A1 | 11/2010 |
| WO | WO 11/005335 | 1/2011 |
| WO | 2011132409 A1 | 10/2011 |
| WO | WO 16/003052 | 1/2016 |

OTHER PUBLICATIONS

PCT Written Opinion for International Patent Application No. PCT/US2005/007108, dated Jun. 27, 2005 (6 pages).

Camarillo et al., "Mechanics Modeling of Tendon-Driven Continuum Manipulators," IEEE Transaction on Robotics, Dec. 2008, pp. 1262-1273, vol. 24, No. 6.

Jung et al., "A Modeling Approach for Continuum Robotic Manipulators: Effects of Nonlinear Internal Device Friction," IEEE/RSJ International Conference on Intelligent Robots and Systems, Sep. 2011, pp. 5139-5146.

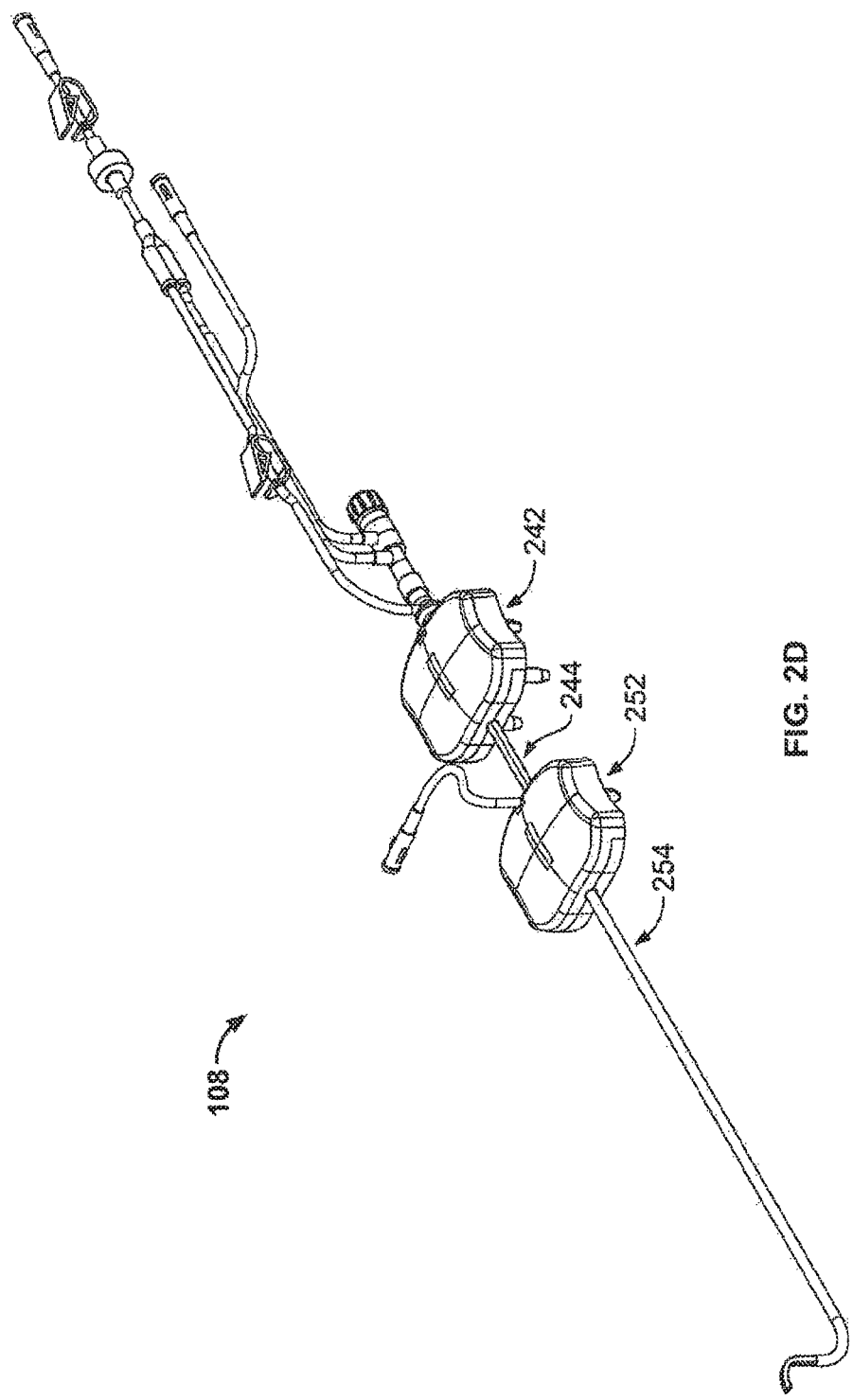

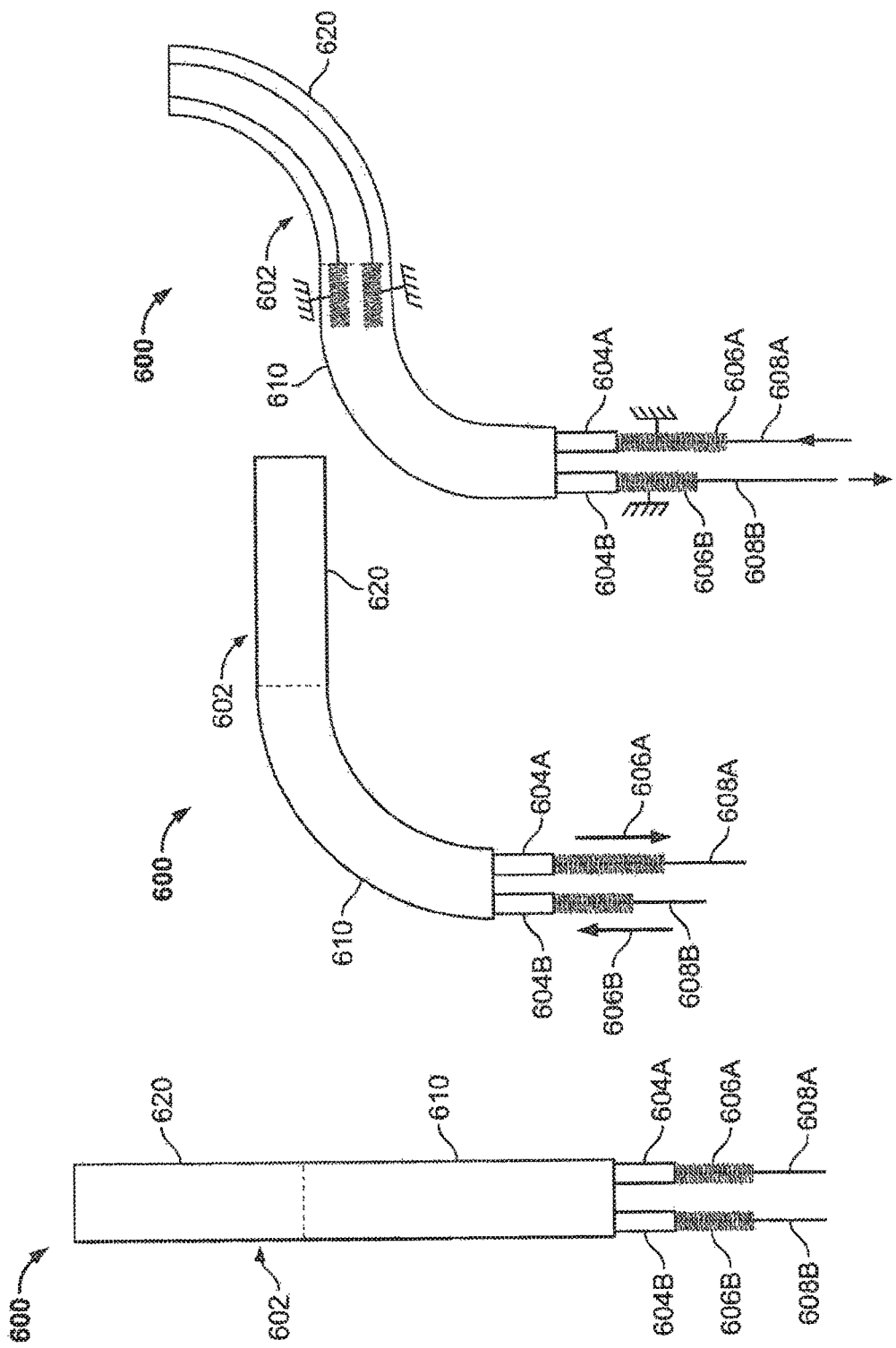

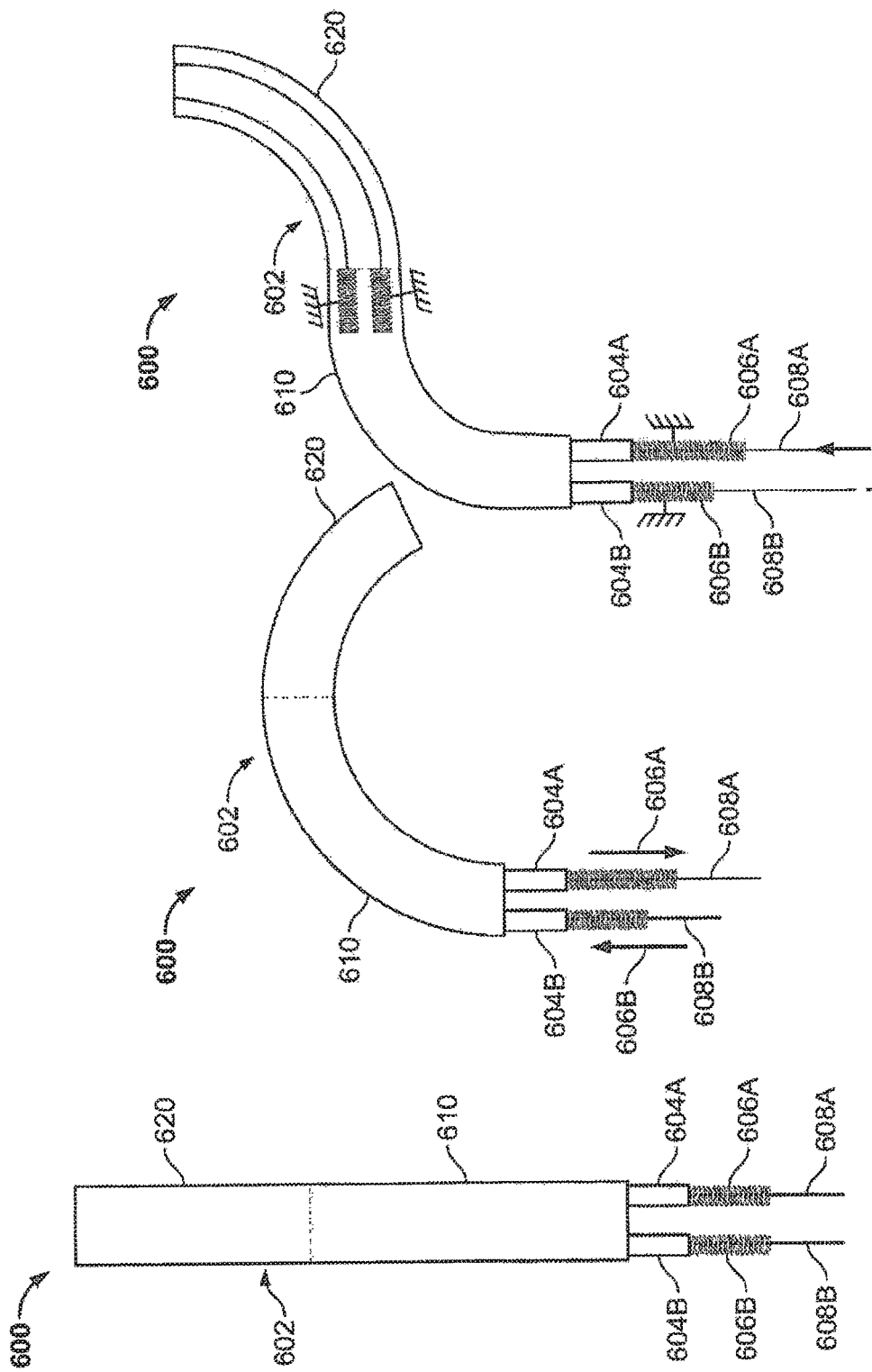

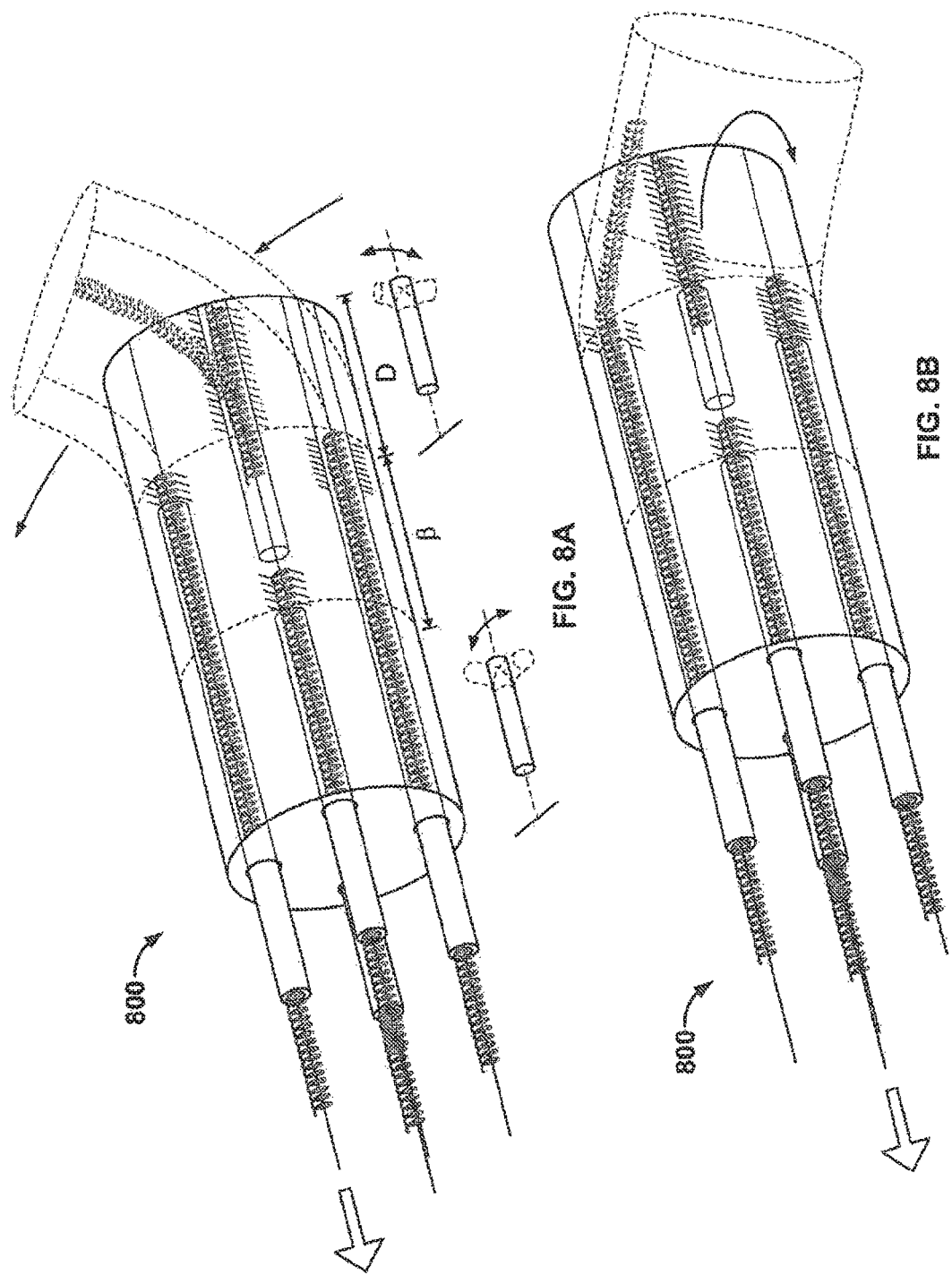

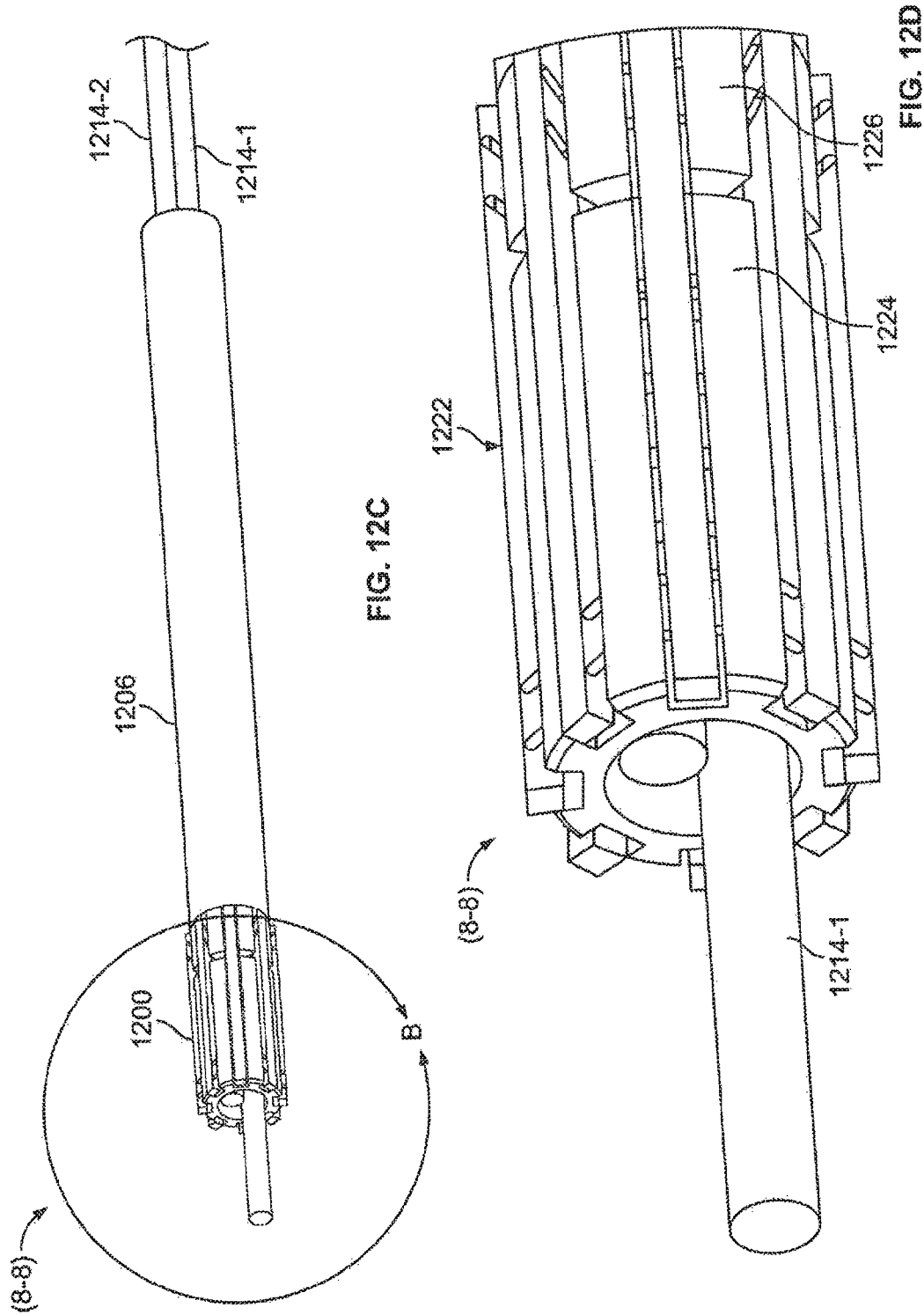

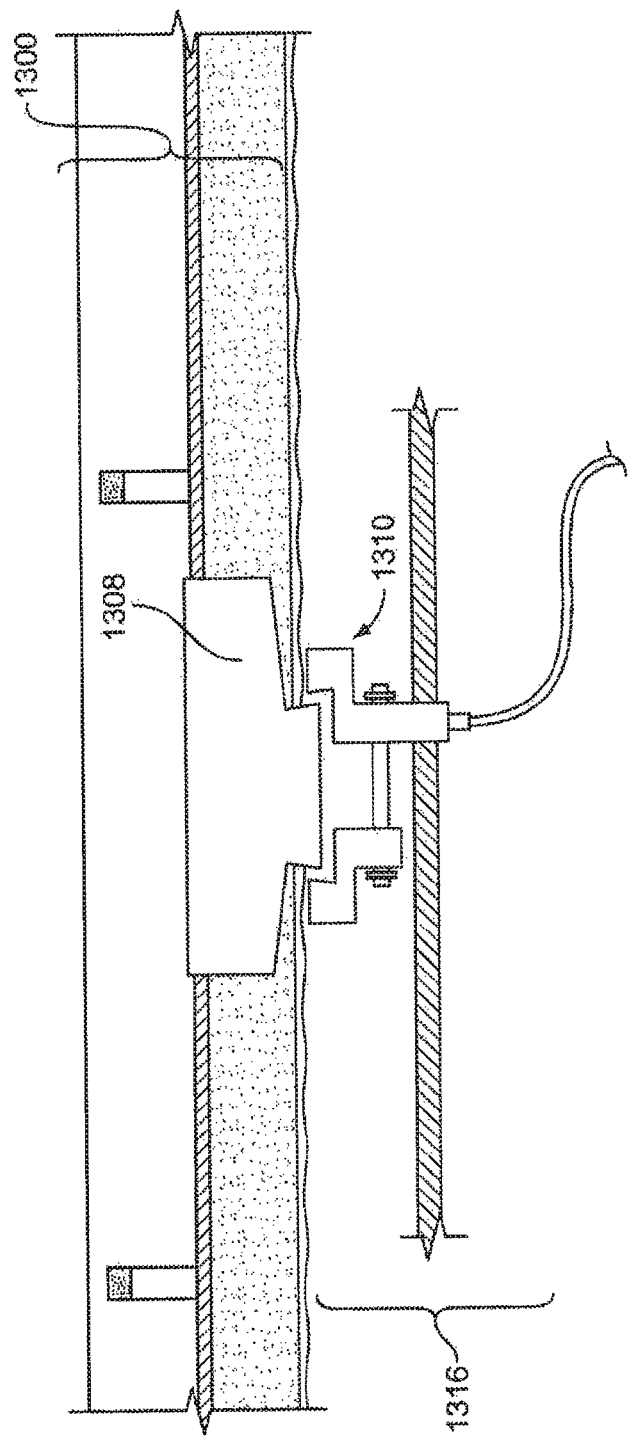

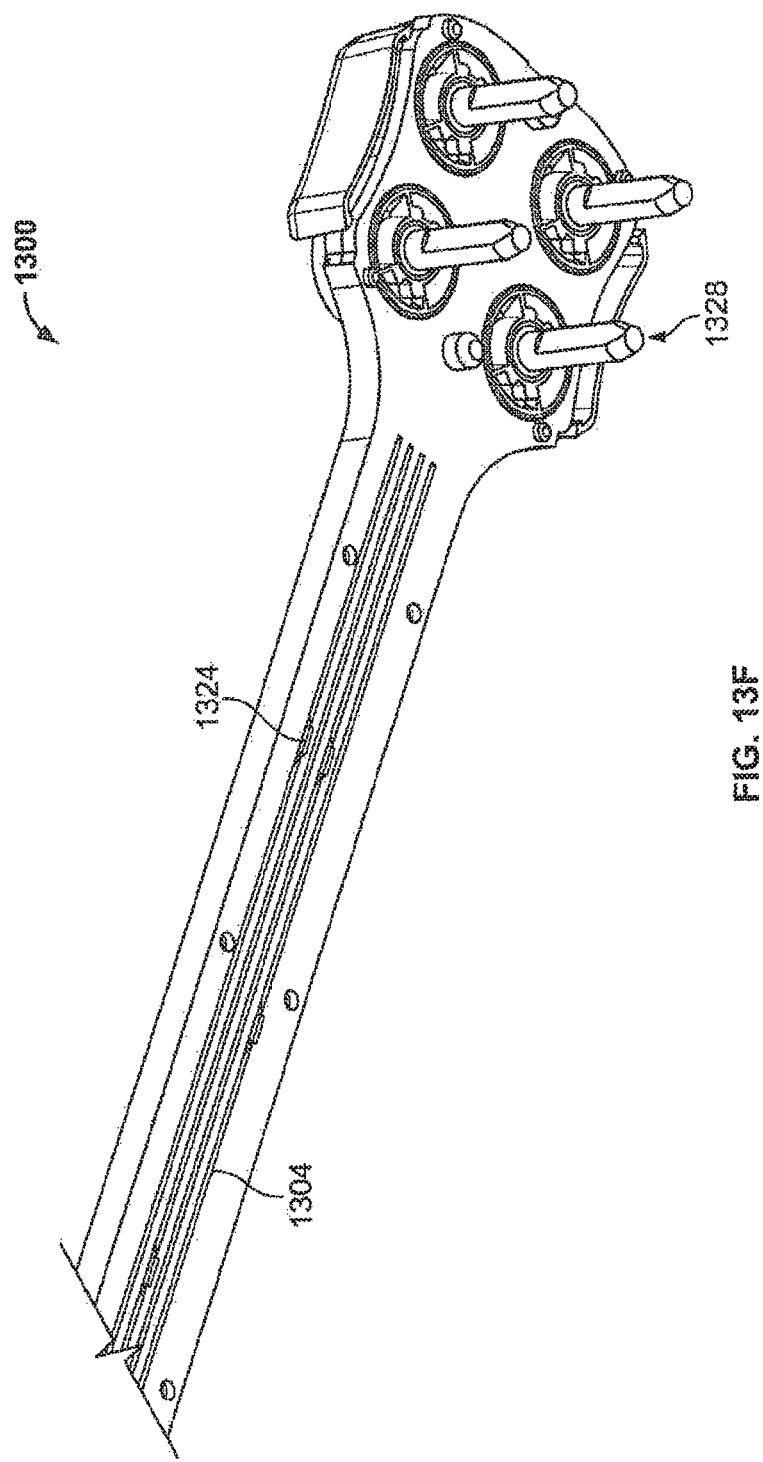

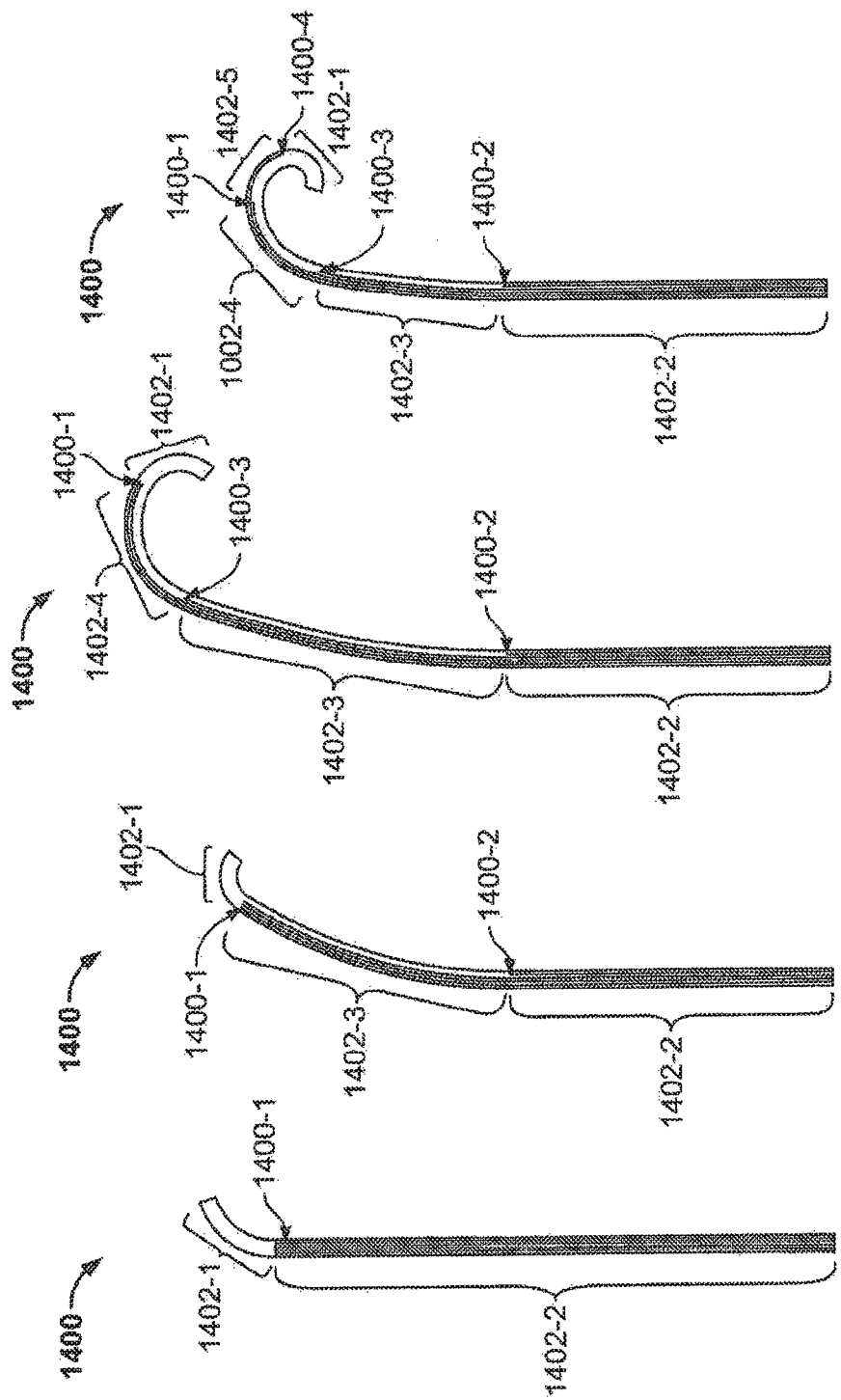

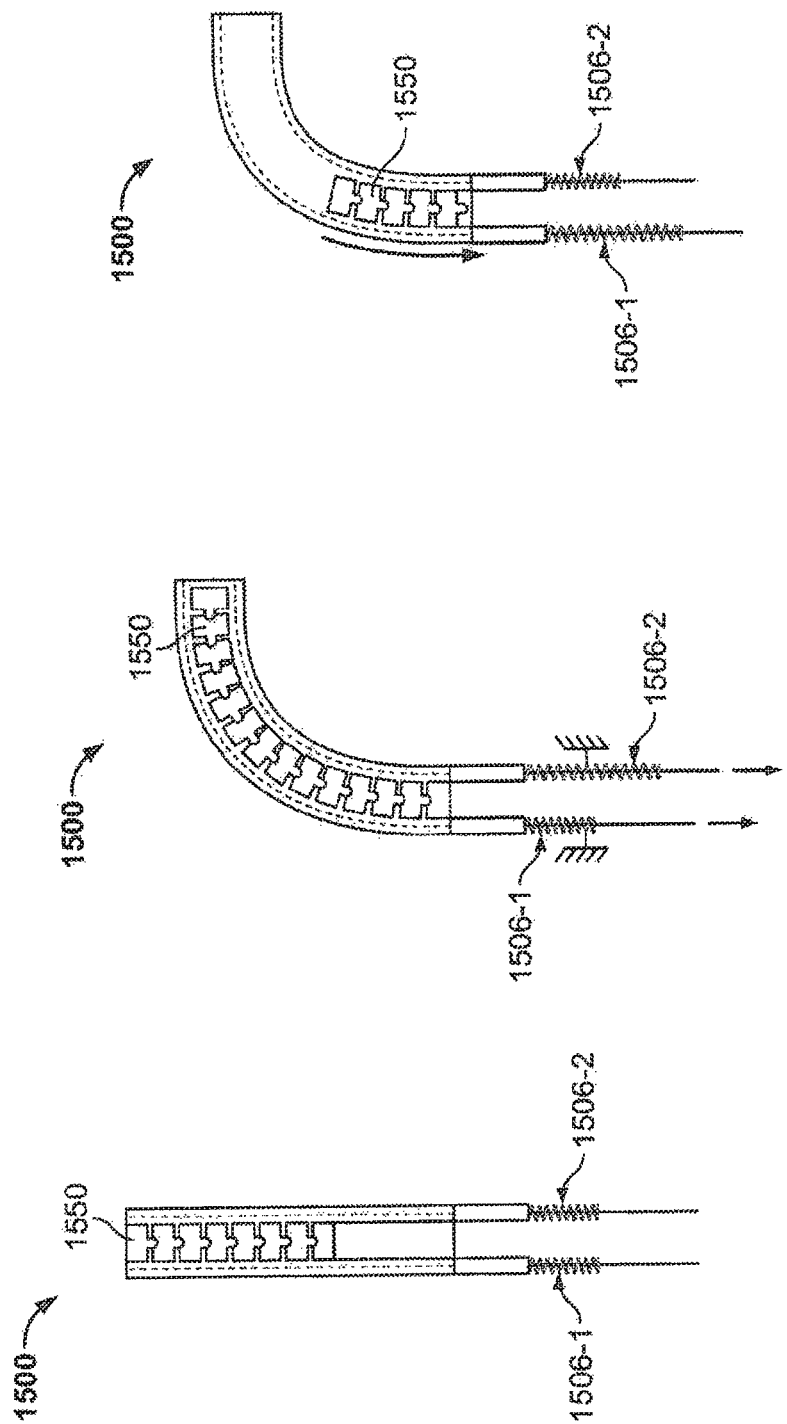

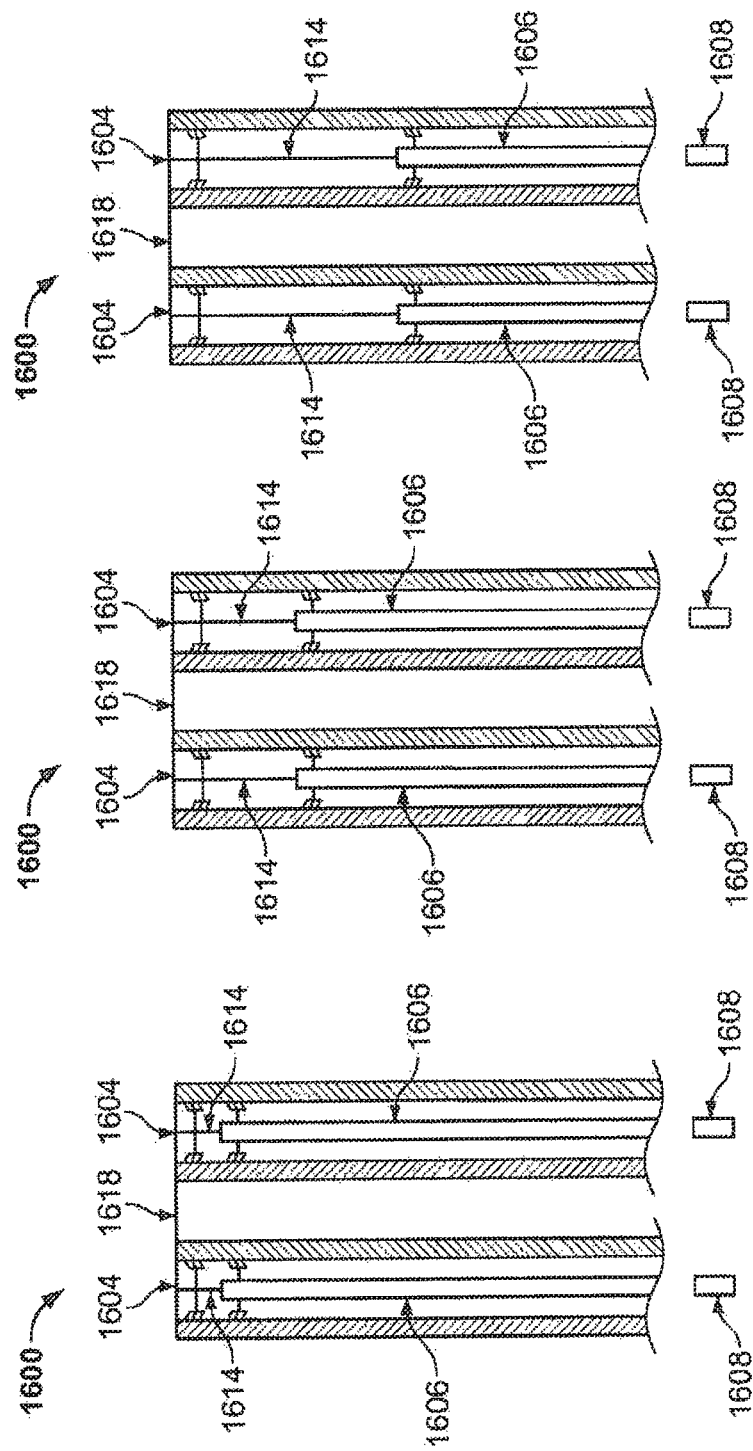

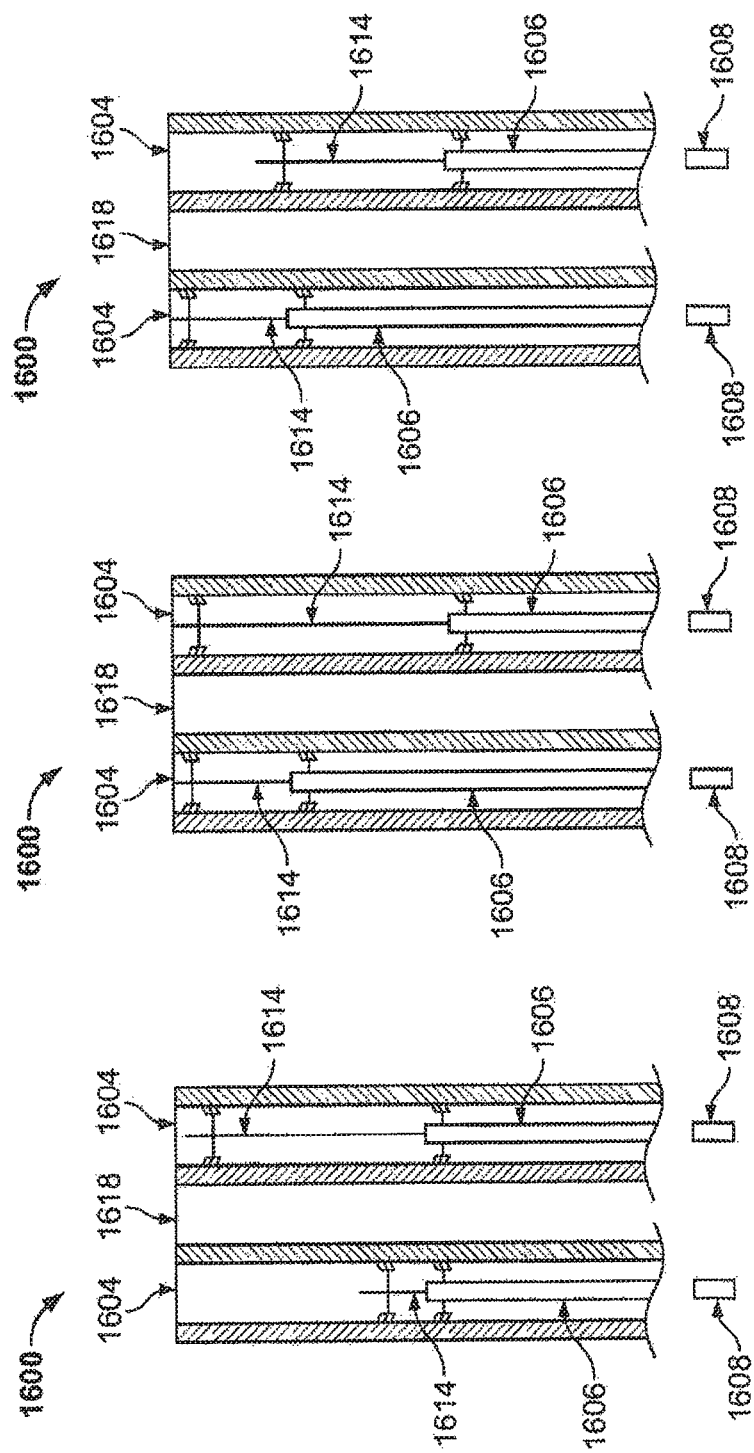

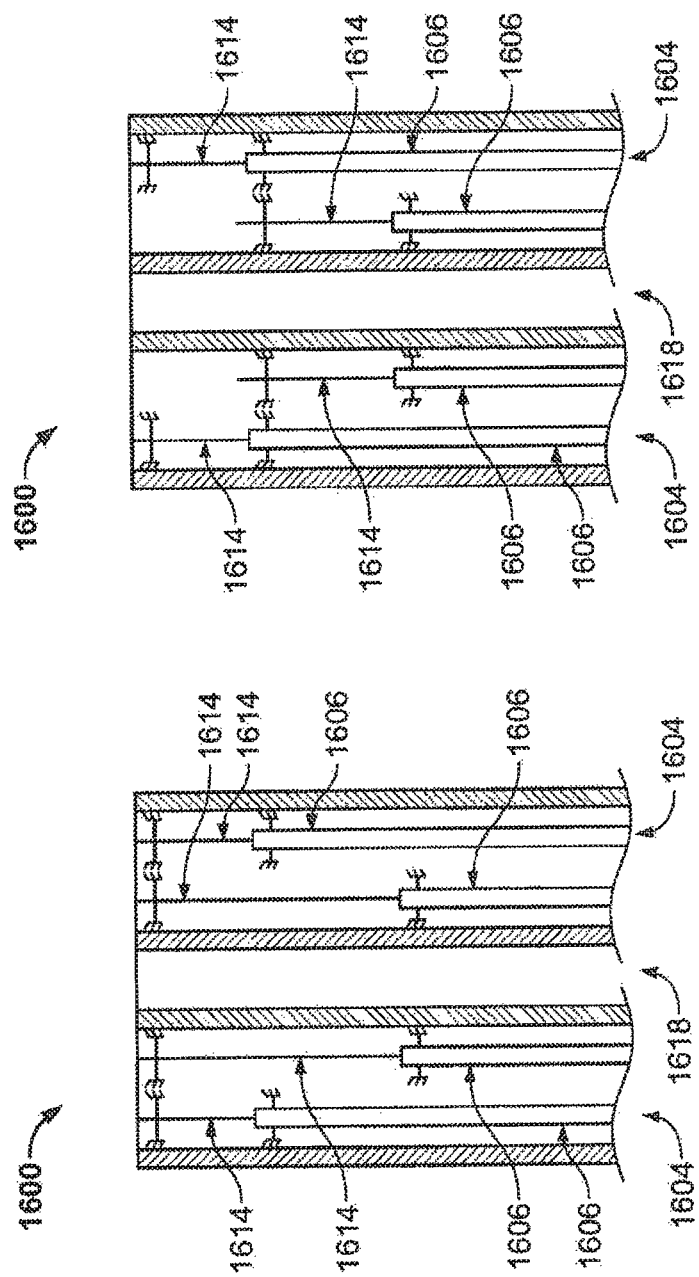

FLEXIBLE AND STEERABLE ELONGATE INSTRUMENTS WITH SHAPE CONTROL AND SUPPORT ELEMENTS

CROSS-REFERENCE TO RELATED APPLICATION

This application is a continuation of U.S. patent application Ser. No. 12/432,683, filed Apr. 29, 2009, entitled "FLEXIBLE AND STEERABLE ELONGATE INSTRUMENTS WITH SHAPE CONTROL AND SUPPORT ELEMENTS," the entirety of which is herein incorporated by reference.

FIELD OF INVENTION

The present invention relates generally to robotically controlled systems, such as robotic or telerobotic surgical systems, and more particularly to flexible and steerable elongate instruments or catheters with adjustable or changeable shape and articulation control for performing minimally invasive surgical operations.

BACKGROUND

Standard surgical procedures or open surgeries typically involve using a scalpel to create an opening of sufficient size to allow a surgical team to gain access to an area in the body of a patient for the surgical team to diagnose and treat one or more target sites. When possible, minimally invasive surgical procedures may be used instead of standard surgical procedures to minimize physical trauma to the patient and reduce recovery time for the patient to recuperate from the surgical procedures. However, minimally invasive surgical procedures typically require using extension tools to approach and address the target site, and the typical extension tools may be difficult to use, manipulate, and control. Consequently, only a limited number of surgeons may have the necessary skills to proficiently manipulate and control the extension tools for performing complex minimally invasive surgical procedures. As such, standard surgical procedures or open surgery might be chosen for the patient even though minimally invasive, surgical procedures may be more effective and beneficial for treating the patient.

Accordingly, there is a need to develop extension tools that are easy to use, manipulate, and control, especially for performing complex minimally invasive surgical procedures.

SUMMARY

In accordance with one embodiment, a steerable elongate instrument has an elongate body with a first lumen and a second lumen within the elongate body. A flex member may be disposed within the second lumen, and a pull wire may be disposed within the flex member. A distal portion of the pull wire may be coupled to a distal portion of the elongate body and a proximal portion of the pull wire may be operatively coupled to a control unit. The control unit may be coupled to a proximal portion of the elongate body.

According to another embodiment, a steerable elongate instrument has an elongate body with a primary lumen, a plurality of secondary lumens within the elongate body, and a plurality of flex members wherein each one of the flex members may be disposed within each one of the plurality of secondary lumens. The steerable elongate instrument may further include a plurality of pull wires wherein each of the pull wires may be respectively disposed within one of the flex members, and the distal portions of the pull wires may be coupled to different locations or portions of the elongate body and proximal portions of the pull wires may be operatively coupled to a control unit. The control unit may be coupled to a proximal portion of the elongate body.

According to another embodiment, a steerable elongated instrument has an elongate body with a plurality of lumens within the elongate body. The steerable elongate instrument may also include a plurality of flex members, and each of the flex members may be respectively disposed within each one of the lumens. The steerable elongate instrument may further include a plurality of pull wires, and each of the pull wires may be respectively disposed within one of the flex members such that distal portions of the pull wires may be coupled to different locations or portions of the elongate body and proximal portions of the pull wires may be operatively coupled to a control unit. The control unit may be coupled to a proximal portion of the elongate body.

According to another embodiment, a steerable elongate instrument has an elongate body with a first lumen and a second lumen within the elongate body. A flex member may be disposed within the second lumen, and the flex member may be configured to provide steering control to a first portion of the elongate body and load bearing support to a second portion of the elongate body. A pull wire may be disposed within the flex member wherein a distal portion of the pull wire may be coupled to a distal portion of the elongate and a proximal portion of the pull wire may be operatively coupled to a control unit. The control unit may be coupled to a proximal portion of the elongate body and the control unit may be configured to operate the pull wire for applying forces to articulate or steer the first portion of the elongate body.

According to another embodiment, a steerable elongate instrument has an elongate body with a primary lumen and a plurality of secondary lumens within the elongate body. The elongate instrument may also include a plurality of flex members such that each of the flex members may be respectively disposed within each of the plurality of secondary lumens. The flex members may be configured to provide steering control to different distal portions of the elongate body and load bearing support to different proximal portions of the elongate body. The elongate instrument further includes a plurality of pull wires and each of the pull wires may be respectively disposed within each of the plurality of the flex members. The distal portions of the pull wires may be coupled to different distal locations or portions of the elongate body and proximal portions of the pull wires may be operatively coupled to a control unit. The control unit may be coupled to a proximal portion of the elongate body, and the control unit may be configured to operate the pull wires for applying forces to articulate or steer the different distal locations or portions of the elongate body.

According to another embodiment, a steerable elongate instrument has an elongate body with a plurality of lumens within the elongate body. The elongate instrument also has a plurality of flex members, and each of the flex members may be respectively disposed within each of the plurality of lumens. The flex members may be configured to provide steering control to different distal portions of the elongate body and load bearing support to different proximal portions of the elongate body. The elongate instrument also includes a plurality of pull wires, and each of the pull wires may be respectively disposed within each of the flex members. Distal portion of respective pull wires may be coupled to different distal locations or portions of the elongate body, and proximal portion of respective pull wires may be operatively coupled to a control unit. The control unit may be coupled to a proximal portion of the elongate body. The control unit may be configured to operate the respective pull wires for applying forces or loads to articulate or steer the different distal locations or portions of the elongate body.

According to another embodiment, an instrument has a flexible and elongate body that has at least one lumen. A flex member may be disposed within the lumen, and the flex member may be capable of providing steering control to a first portion of the elongate body while providing load bearing support to a second portion of the elongate body. A pull wire may be disposed within the flex member, and at least a distal portion of the pull wire may coupled to the elongate body and a proximal portion of the pull wire may be operatively coupled to a control unit. The control unit may be coupled to a proximal portion of the elongate body.

According to another embodiment, an instrument includes a flexible and elongate body that has at least one lumen. A flex member may be disposed within the lumen, and the flex member may be capable of providing steering control to a first portion of the elongate body while providing load bearing support to a second portion of the elongate body. A pull wire may be disposed within the flex member, and at least a distal portion of the pull wire may coupled to the elongate body and a proximal portion of the pull wire may be operatively coupled to a control unit. The control unit may be coupled to a proximal portion of the elongate body. The flex member may be further configured to selectively decouple articulation or steering forces of a first portion of the elongate body away from a second portion of the elongate body; thereby, preventing compression of the second portion of the elongate body while maintaining elasticity or flexibility of the second portion of the elongate body.

According to another embodiment, a method of shape or articulation control of an elongate instrument may be provided. The method may include inserting an elongate instrument into a patient through either an incision or orifice, advancing the elongate instrument through a pathway inside the patient, manipulating the elongate instrument to conform or match a shape or curvature of the pathway as the elongate instrument is being advanced through the pathway, and steering or articulating a distal portion of the elongate instrument around other curvatures of the pathway.

According to another embodiment, a steerable elongate instrument has an elongate body with a first lumen and a second lumen within the elongate body, and a flex member may be disposed within the second lumen. A pull wire may be disposed within the flex member, wherein a distal portion of the pull wire may be coupled to a distal portion of the elongate body and a proximal portion of the pull wire may be operatively coupled to a control unit. The control unit may be coupled to a proximal portion of the elongate body, and a control member may be operatively coupled to the control unit wherein a distal portion of the control member may be positioned near a proximal portion of the flex member.

According to another embodiment, a steerable elongate instrument has an elongate body with a primary lumen and a plurality of secondary lumens within the elongate body. The steerable elongate instrument may also include a plurality of flex members, and each of the plurality of flex members may be respectively disposed within each of the secondary lumens. The steerable elongate instrument may further include a plurality of pull wires wherein each of the pull wires may be respectively disposed within each of the flex members, and distal portion of each of the pull wires may be coupled to different locations or portions of the elongate body and proximal portion of each of the pull wires are operatively coupled to a control unit. The control unit may be coupled to a proximal portion of the elongate body. A plurality of control members may be operatively coupled to the control unit such that distal portions of the control members may positioned near the proximal portions of the flex members.

According to another embodiment, a steerable elongate instrument has an elongate body with a plurality of lumens within the elongate body and a plurality of flex members. Each of the flex members may be respectively disposed within each of the lumens. The steerable elongate instrument may also includes a plurality of pull wires, and each of the pull wires may be respectively disposed within each of the flex members such that distal portion of each of the pull wires may coupled to different locations or portions of the elongate body and proximal portion of each of the pull wires may be operatively coupled to a control unit. The control unit may be coupled to a proximal portion of the elongate body, and a plurality of control members may be operatively coupled to the control unit wherein distal portions of the control members may be positioned near the proximal portions of the flex members.

According to another embodiment, a steerable elongate instrument has an elongate body having a first lumen and a second lumen within the elongate body and a flex member disposed within the second lumen. The flex member may be configured to provide steering control to a first portion of the elongate body and load bearing support to a second portion of the elongate body. A pull wire may be disposed within the flex member, and a distal portion of the pull wire may be coupled to a distal location or portion of the elongate body and a proximal portion of the pull wire may be operatively coupled to a control unit. The control unit may be coupled to a proximal portion of the elongate body and the control unit may be configured to operate the pull wire for applying forces to articulate or steer the first portion of the elongate body. A control member may be operatively coupled to the control unit wherein a distal portion of the control member may be positioned near a proximal portion of the flex member. The control member may be configured to support the flex member and control movement or displacement of the flex member.

According to another embodiment, an instrument having a flexible and elongated body includes at least a lumen and a flex member disposed within the lumen. The flex member may be configured to provide steering control to a first portion of the elongate body while providing load bearing support to a second portion of the elongate body. A pull wire may be disposed within the flex member, and at least a distal portion of the pull wire may be coupled to the elongate body and a proximal portion of the pull wire may be operatively coupled to a control unit. The control unit may be coupled to a proximal portion of the elongate body. In addition, a control member may be operatively coupled to the control unit such that a distal portion of the control member may be positioned near a proximal portion of the flex member. The control member may be. configured to support the flex member and control the movement or displacement of the flex member. Furthermore, the flex member may be configured to selectively decouple articulation or steering forces of a first portion of the elongate body away from a second portion of the elongate body; thereby, preventing compression of the second portion of the elongate body while maintaining elasticity or flexibility of the second portion of the elongate body.

According to another embodiment, a steerable elongate instrument has an elongate body with a primary lumen, a plurality of secondary lumens within the elongate body, and a plurality of flex members. Each of the plurality of flex members may be disposed within each of the secondary lumens. The flex members may be configured to provide steering control to different distal portions of the elongate body and load bearing support to different proximal portions of the elongate body. The steerable elongate instrument may also include a plurality of pull wires wherein each of the pull wires may be disposed within each of the flex members. In addition, distal portion of each of the pull wires may be coupled to different distal locations or portions of the elongate body and proximal portion of each of the pull wires may be operatively coupled to a control unit. The control unit may be coupled may be coupled to a proximal portion of the elongate body. Furthermore, a plurality of control members may be operatively coupled to the control unit wherein distal portions of the control members may be positioned near the proximal portions of the flex members, and the control members may be configured to support the flex members and control movement or displacement of the flex members.

According to another embodiment, a steerable elongate instrument has an elongate body with a plurality of lumens within the elongate body and a plurality of flex members. Each of the flex members may be disposed within each of the lumens, and the flex members may be configured to provide steering control to different distal portions of the elongate body and load bearing support to different proximal portions of the elongate body. The steerable elongate instrument may also include a plurality of pull wires. Each of the pull wires may be disposed within each of the flex members, wherein distal portion of each of the pull wires may be coupled to different distal locations or portions of the elongate body and proximal portion of each of the pull wires may be operatively coupled to a control unit. The control unit may be coupled to a proximal portion of the elongate body. The steerable instrument may further include a plurality of control members that may be operatively coupled to the control unit such that distal portions of the control members may be positioned near the proximal portions of the flex members. The control members may be configured to support the flex members and control movement or displacement of the flex members.

According to another embodiment, a method of shape or articulation control of an elongate instrument may be provided. The method may include inserting an elongate instrument into a patient through either an incision or orifice, advancing the elongate instrument through a pathway inside the patient, manipulating the elongate instrument to conform or match a shape or curvature of the pathway as the elongate instrument is being advanced through the pathway, and steering or articulating a distal portion of the elongate instrument around other curvatures of the pathway. In addition, the method may further include advancing a control member against a proximal portion of a flex member of the elongate instrument. The method may also include locking the conformed or matched shape or curvature of a proximal portion of the elongate instrument.

According to another embodiment, a method of shape of articulation control of an instrument may be provided. The method may include inserting an elongate instrument into a patient, wherein the elongate instrument comprises a distal portion, a mid portion, and a proximal portion. The method may also include advancing the distal and mid portions of the elongate instrument through a pathway inside the patient, manipulating the mid portion of the elongate instrument to conform to a shape or curvatures in the pathway as the elongate instrument is being advanced through the pathway, and locking the mid portion of the elongate instrument such that the mid portion maintains the conformed shape or curvatures while the distal portion of the elongate instrument is manipulated to assume a curvature independent of the mid portion.

According to another embodiment, a steerable elongate instrument has an elongate body with a first lumen and a second lumen within the elongate body, a flex member disposed within the second lumen, and a first pull wire disposed within the flex member wherein a distal portion of the first pull wire may be coupled to a distal portion of the elongate body and a proximal portion of the first pull wire may be operatively coupled to a control unit. The control unit may be coupled to a proximal portion of the elongate body. A second pull wire may be disposed within the flex member, and a distal portion of the second pull wire may be coupled to a distal portion of the flex member and a proximal portion of the second pull wire may be operatively coupled to the control unit. Additionally, a control member may be operatively coupled to control unit such that a distal portion of the control member may be positioned near a proximal portion of the flex member.

According to another embodiment, a steerable elongate instrument has an elongate body with a first lumen and a second lumen within the elongate body, and a flex member disposed within the second lumen. The flex member may be configured to provide steering control to a first portion of the elongate body and load bearing support to a second portion of the elongate body. The steerable instrument may also include a first pull wire and a second pull wire. A distal portion of the first pull wire may be coupled to a distal portion of the elongate body and a proximal portion of the first pull wire may be operatively coupled to a control unit. The control unit may be coupled to a proximal portion of the elongate body, and the control unit may be configured to operate the first pull wire for applying forces to articulate or steer the first portion of the elongate body. In addition, a distal portion of the second pull wire may be coupled to a distal portion of the flex member and a proximal portion of the second pull wire may be operatively coupled to the control unit. The control unit may be configured to operate the second pull wire to control displacement of the flex member. The steerable instrument may further include a control member that may be operatively coupled to the control unit such that a distal portion of the control member may be positioned near a proximal portion of the flex member. The control member may be configured to control displacement of the flex member.

According to another embodiment, a method for shape or articulation control may be provided. The method may include inserting an elongate instrument into a patient through either an incision or orifice, advancing the elongate instrument through a pathway inside the patient, manipulating the elongate instrument to conform or match a shape or curvature of the pathway as the elongate instrument is being advanced through the pathway, controlling the displacement of a flex member along a length of the elongate instrument, and steering a first portion or a second portion of the elongate instrument around curvatures of the pathway.

According to another embodiment, a method of shape or articulation control may be provided. The method may include inserting an elongate instrument into a patient through either an incision or orifice, advancing the elongate instrument through a pathway inside the patient, manipulating the elongate instrument to conform or match a shape or curvature of the pathway as the elongate instrument is being advanced through the pathway, controlling the displacement of a flex member along a length of the elongate instrument, altering the stiffness of a first portion of the elongate instrument, changing the radius of curvature of the elongate instrument, and steering the first portion or second portion of the elongate instrument around curvatures of the pathway.

According to another embodiment, an instrument having a flexible and elongated body includes at least two lumens and a flex member disposed within one of the lumens. The flex member may be capable of providing steering control to a first portion of the elongate body while providing load bearing support to a second portion of the elongate body. A pull wire may be disposed within the flex member, and at least a distal portion of the pull wire may be coupled to the elongate body and a proximal portion of the pull wire may be operatively coupled to a control unit. The control unit may be coupled to a proximal portion of the elongate body. In addition, a control member may be operatively coupled to the control unit such that a distal portion of the control member may be positioned near a proximal portion of the flex member. The control member may be configured to support the flex member and control the movement or displacement of the flex member. Furthermore, the flex member may be configured to be anchored to the elongate body between the first and second portion of the elongate body to selectively decouple articulation or steering forces of a first portion of the elongate body away from a second portion of the elongate body; thereby, preventing twist or compression of the second portion of the elongate body while maintaining elasticity or flexibility of the second portion of the elongate body.

According to another embodiment, an instrument having a flexible and elongated body includes at least two lumens and a flex member disposed within one of the lumens. The flex member may be capable of providing steering control to a first portion of the elongate body while providing load bearing support to a second portion of the elongate body. A pull wire may be disposed within the flex member, and at least a distal portion of the pull wire may be coupled to the elongate body and a proximal portion of the pull wire may be operatively coupled to a control unit. The control unit may be coupled to a proximal portion of the elongate body. In addition, a control member may be operatively coupled to the control unit such that a distal portion of the control member may be positioned near a proximal portion of the flex member. The control member may be configured to support the flex member and control the movement or displacement of the flex member. Furthermore, the flex member may be configured to be anchored to the elongate body between the first and second portion of the elongate body to selectively decouple articulation or steering forces of a first portion of the elongate body away from a second portion of the elongate body; thereby, preventing twist or compression of the second portion of the elongate body while maintaining elasticity or flexibility of the second portion of the elongate body. In addition, the flex member may not be anchored to the elongate body; instead, it may be positioned at various locations of the elongate body to affect or alter the bending stiffness of various sections or portions of the elongate body. Moreover, by way of a retractable anchor, the flex tube may operate as a structure or device that decouples articulation forces from at least a portion of the elongate body, and the flex tube may also operate as a structure or device that could affect or alter the bending stiffness to at least a portion of the elongate body.

Other and further features and advantages of embodiments of the invention will become apparent from the following detailed description, when read in view of the accompanying figures.

BRIEF DESCRIPTION OF THE DRAWINGS

The present invention will be readily understood by the following detailed description, taken in conjunction with accompanying drawings, illustrating by way of examples the principles of the invention. The objects and elements in the drawings are not necessarily drawn to scale, proportion, precise orientation or positional relationships; instead, emphasis is focused on illustrating the principles of the invention. The drawings illustrate the design and utility of various embodiments of the present invention, in which like elements are referred to by like reference symbols or numerals. The drawings, however, depict the embodiments of the invention, and should not be taken as limiting its scope. With this understanding, the embodiments of the invention will be described and explained with specificity and detail through the use of the accompanying drawings in which:

FIG. 2A through FIG. 2D illustrate various embodiments of an instrument assembly.

FIG. 6A through FIG. 6C illustrate the operation of a substantially flexible and steerable elongate instrument in accordance with one embodiment.

FIG. 7A through FIG. 7C illustrate the operation of a substantially flexible and steerable elongate instrument in accordance with one embodiment.

FIG. 8A and FIG. 8B illustrate curve aligned steering of a flexible and steerable elongate instrument in accordance with one embodiment.

FIG. 12A through FIG. 12F illustrate a deployable and retractable anchor in accordance with one embodiment.

FIG. 13A through FIG. 13F illustrate a control unit or splayer configured to operate multiple flex tubes or flex members in accordance with one embodiment.

FIG. 14A through 14D illustrate various embodiments of elongate instruments having flex tubes located or secured at various positions or locations along the length of the elongate instruments.

FIG. 15A through 15C illustrate a simplified construction of an elongate instrument (1500) with variable shape control and support in accordance with one embodiment.

FIG. 16A through 16F illustrate a sample of variations in which one set of flex tubes may be configured or implemented in a set of control lumens within the body of an elongate instrument.

FIG. 16G through FIG. 16J illustrate a sample of variations in which a plurality of flex tubes may be disposed or implemented in a control lumen of an elongate instrument.

FIG. 16I and FIG. 16J illustrate a sample of variations in which one of the plurality of flex tubes in a control lumen may be configured in a passively controlled manner, while one or more other flex tubes may be configured in a passively controlled manner, actively controlled manner, or displaceable controlled manner.

DETAILED DESCRIPTION OF ILLUSTRATED EMBODIMENTS

Reference will now be made in detail to the preferred embodiments of the present invention, examples of which are illustrated in the accompanying drawings. While the invention will be described in conjunction with the preferred embodiments, it will be understood that they are not intended to limit the scope of the invention to these embodiments. On the contrary, the invention is intended to cover alternatives, modifications, and equivalents that may be included within the spirit and scope of the invention. Furthermore, in the following detailed description of the present invention, numerous specific details are set forth in to order to provide a thorough understanding of the present invention. However, it will be readily apparent to one of ordinary skilled in the art that the present invention may be practiced without these specific details.

Figure 1:
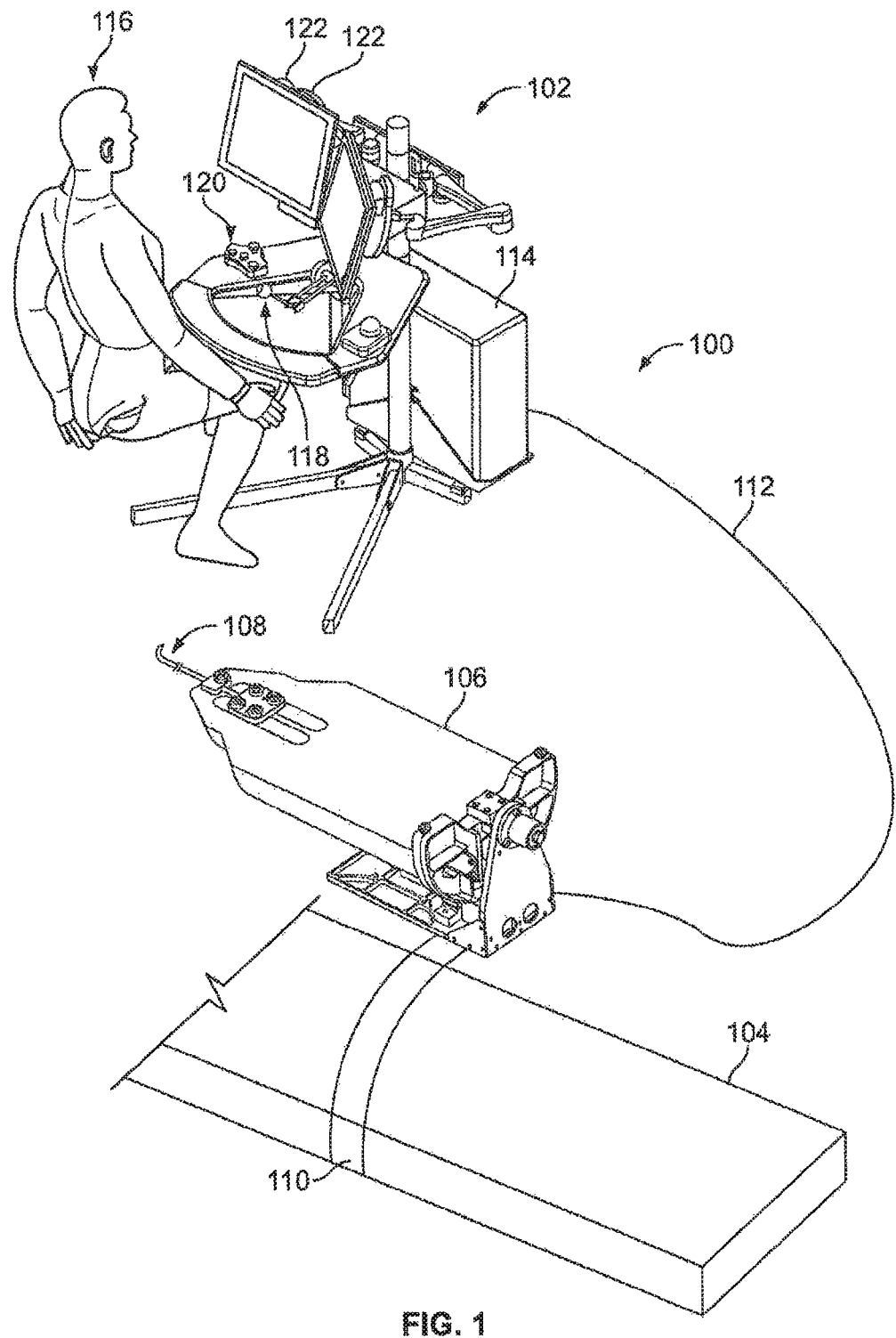
FIG. 1 illustrates one example of a robotic or telerobotic surgical system.

The contents of the following applications are incorporated herein by reference as though set forth in full for all purposes: U.S. patent application Ser. No. 11/073,363, filed on Mar. 4, 2005; U.S. patent application Ser. No. 11/418, 398, filed on May 3, 2006; U.S. patent application Ser. No. 11/637,951, filed on Dec. 11, 2006; and U.S. patent application Ser. No. 12/079,500, filed on Mar. 26, 2008. All of the following technologies may be utilized or compatible with manually or robotically steerable instruments, such as those described in the aforementioned U.S. patent application Ser. No. 11/073,363; U.S. patent application Ser. No. 11/418, 398; U.S. patent application Ser. No. 11/637,951; and U.S. patent application Ser. No. 12/079,500. FIG. 1 illustrates one example of a robotic or telerobotic surgical system (100), e.g., the Sensei® Robotic Catheter System from Hansen Medical, Inc. in Mountain View, Calif., U.S.A., with an operator control station (102) located remotely from an operating table (104) to which an electromechanical device, instrument driver, or robotic catheter manipulator (RCM) (106) and instrument assembly or steerable catheter assembly (108), e.g., the Artisan™ Control Catheter also from Hansen Medical, Inc. in Mountain View, Calif., U.S.A., may be supported by an instrument driver mounting brace (110) that is mounted on the operation table (104). A wired connection (112) transfers signals between an electronics rack (114) near the operator control station (102) and the instrument driver (106) mounted near the operation table (104). The electronics rack (114) includes system hardware and software that operate and perform the many functions of the robotic or telerobotic surgical system (100). The instrument driver mounting brace (110) may be a substantially arcuate-shaped structural member configured to position the instrument driver (106) above a patient (not shown) who is lying on the operating table (104). The wired connection (112) may transmit manipulation, articulation, and control commands from an operator or surgeon (116) who is working at the operator control station (102) and who may be providing the necessary input to the instrument driver (106) by way of one or more input devices, such as an instinctive Motion™ controller (118), joystick, keyboard (120), trackball, data gloves, exoskeletal gloves, or the like, for operating the instrument assembly (108) to perform various operations, such as minimally invasive procedures, on the patient who is lying on the operating table (104). The wired connection (112) may also transmit information (e.g., visual, tactile, force feedback, position, orientation, shape, localization, electrocardiogram, etc.) from the instrument assembly (108), patient, and operation site monitors (not shown in this figure) to the operator control station (102) for providing the necessary information to the operator or surgeon (116) to facilitate monitoring the instruments, patient, and target site for performing various precise manipulation and control of the instrument assembly (108) during minimally invasive surgical procedures. The wired connection (112) may be a hard wire connection, such as an electrical wire configured to transmit electrical signals (e.g., digital signals, analog signals, etc.), an optical fiber configured to transmit optical signals, a wireless link connection configured to transmit various types of wireless signals (e.g., RF signals, microwave signals, etc.), etc., or any combinations of electrical wire, optical fiber, and/or wireless links. The wire connection (112) allows the surgeon or operator (116) to be remotely located from the patient. The surgeon or operator (116) may be located across the operation room from the patient, in a different room, in a different building, or in a different geographical region away from where the patient is located. Information or feedback transmitted by way of the wire connection (112) may be displayed on one or more monitors (122) at the operator control station (102).

Figure 2A:
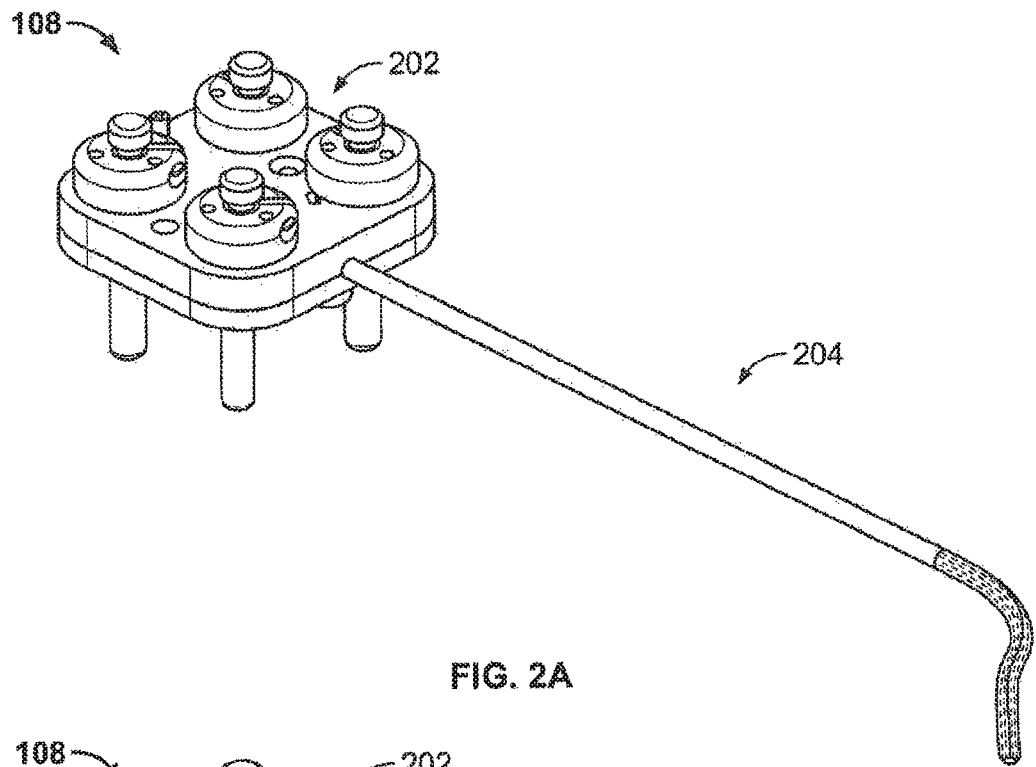
Figure 2B:
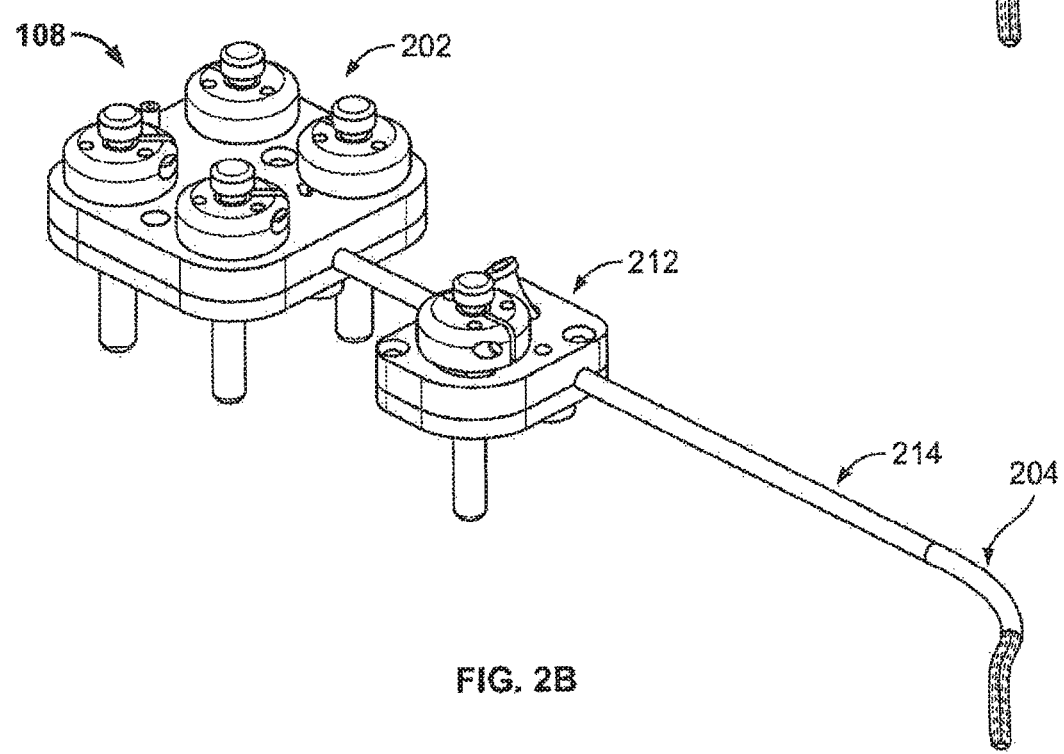
Figure 2C:
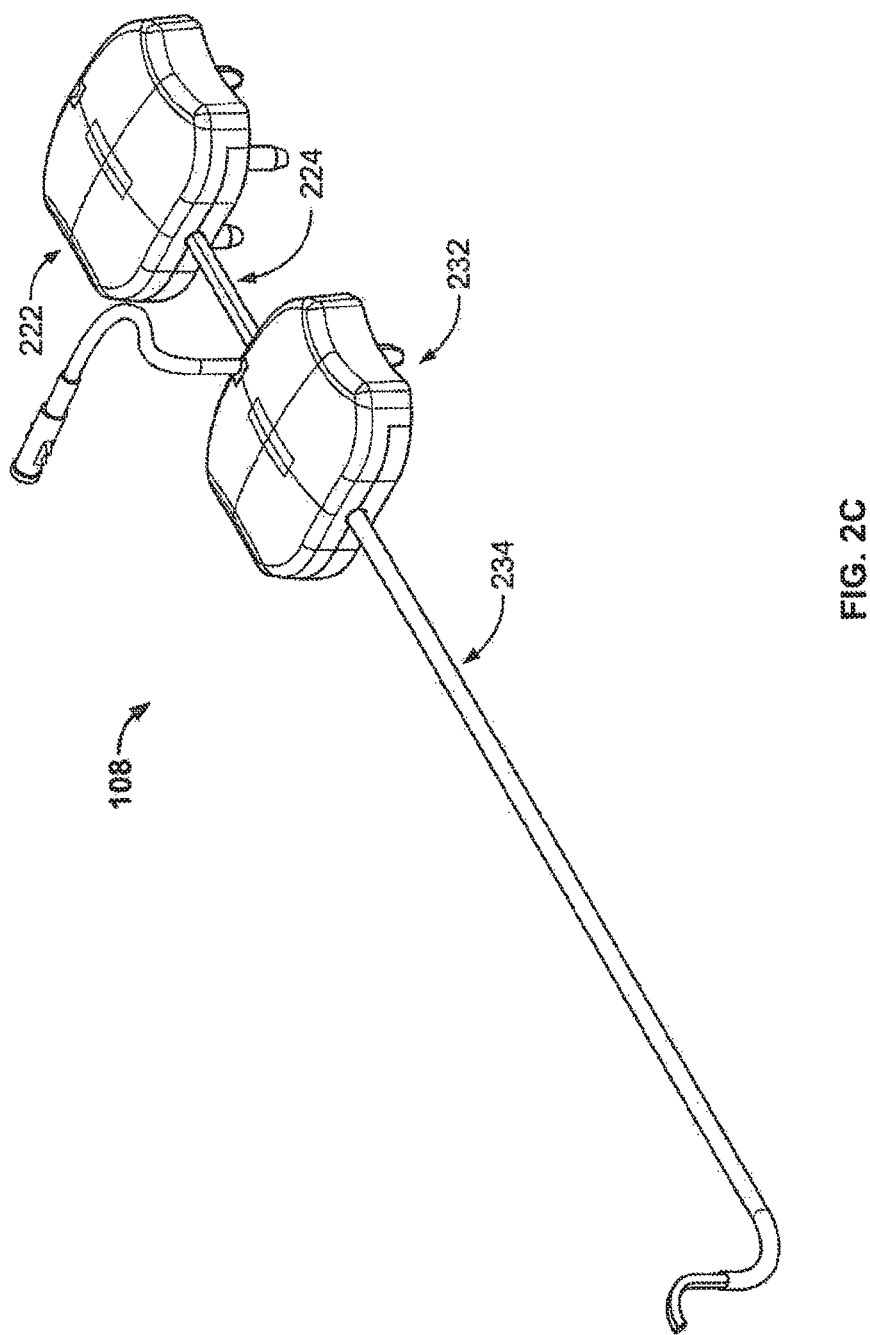

FIG. 2A through FIG. 2D illustrate various embodiments of an instrument assembly (108) that may be configured to perform various minimally invasive surgical procedures. An instrument assembly (108) may be comprised of a single steerable elongate instrument assembly or catheter system, as illustrated in FIG. 2A, or a combination of steerable elongate instrument assemblies or catheter systems, as illustrated in FIG. 2B through 2D. As illustrated in FIG. 2B through 2D, the steerable elongate instrument assemblies or catheter systems may be positioned or mounted in a substantially coaxial manner and configured to be operated in a substantially coordinated or tandem-type manner or as a coordinated or tandem-type combination. As described in the aforementioned patent applications that have been incorporated by reference, the instrument assembly (108) may include a control unit or splayer; which may be comprised of gears, pulleys, and control or pull wires to steer or articulate an elongate instrument or catheter in various degrees of motion (e.g., up, down, pitch, yaw, or any motion in-between as well as any other motions). For example, FIG. 2A illustrates one embodiment of an instrument assembly or catheter system (108) which includes a control unit (202) that may be configured to steer an elongate instrument or catheter (204). FIG. 2B illustrates another embodiment of an instrument assembly (108) that includes a combination of steerable elongate instrument assemblies or catheter systems which includes respective control units (202 and 212) and corresponding associated elongate instruments or catheters (204 and 214). The elongate instrument assemblies or catheter systems, as those illustrated in FIG. 2B as well as other similar systems or combinations, may be positioned or mounted coaxially with the elongate instrument or catheter of one elongate instrument assembly or catheter system threaded or loaded through a lumen of another elongate instrument assembly or catheter system. FIG. 2C also illustrates an instrument assembly (108) that includes a combination of steerable elongate instrument assemblies or catheter systems which are comprised of respective control units or splayers (222 and 232) and corresponding associated elongate instruments or catheters (224 and 234). FIG. 2D illustrates another embodiment of an instrument assembly (108) that includes a combination of steerable elongate instrument assemblies and catheter systems which may also include respective control units or splayers (242 and 252) and corresponding associated elongate instruments or catheters (244 and 254).

Basic Structure of a Steerable Instrument

Figure 3A:
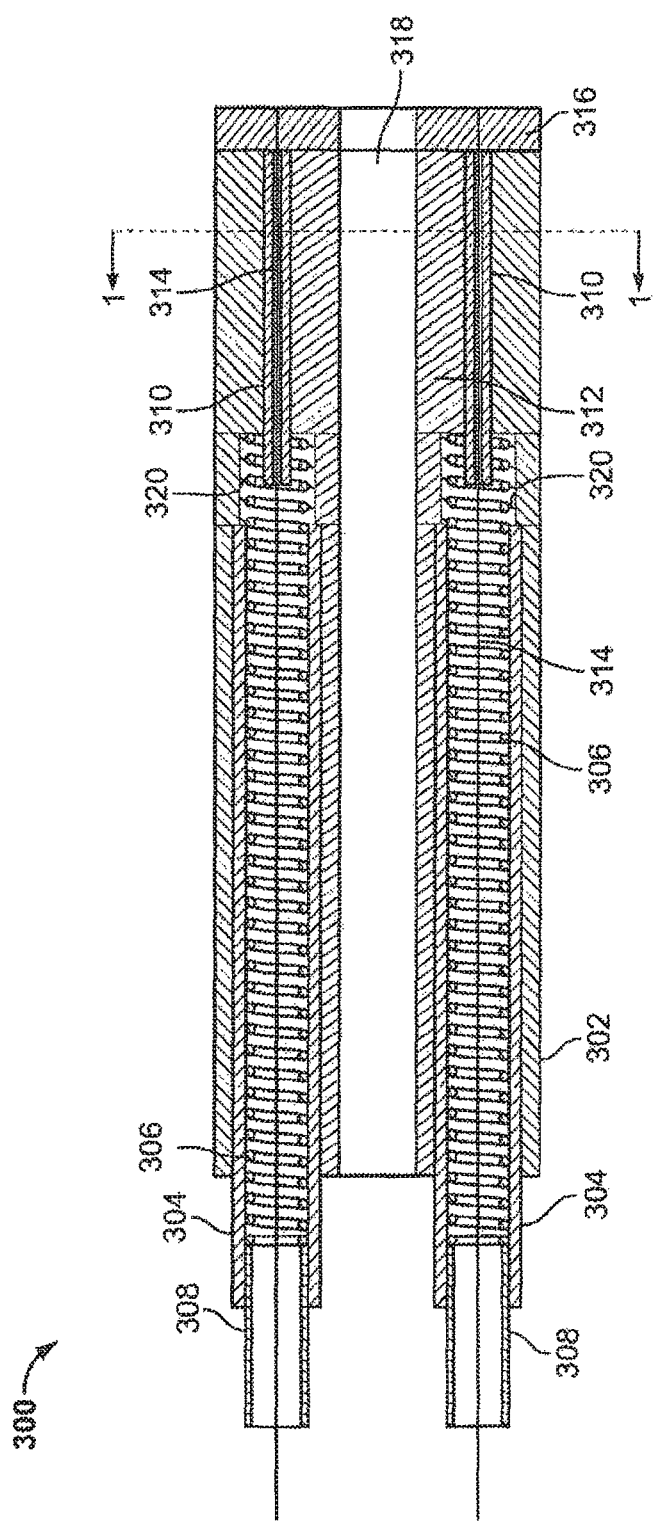
FIG. 3A illustrates a cross-sectional view of a flexible and steerable elongate instrument with variable or changeable shape control and support elements in accordance with one embodiment.

FIG. 3A illustrates a cross-sectional view of a section or portion of a flexible and steerable elongate instrument or catheter (300) of an instrument assembly (108) in accordance with one embodiment. The steerable elongate instrument (300) may be substantially pliable or flexible such that when it is advanced into a patient, an operator or surgeon may easily manipulate the instrument (300) to conform, adopt, or match the shape or curvatures of the internal pathways (e.g., gastrointestinal tract, blood vessels, etc.) of the patient. As illustrated, the flexible and steerable elongate instrument or catheter (300) may be comprised of multiple layers of materials and/or multiple tube structures. For example, the elongate instrument (300) may includes an outer layer or outer tube (302), a main lumen, primary lumen, or central lumen (318) defined by an inner layer or inner tube (312), and minor, secondary, or peripheral lumens incorporated in the body of the elongate instrument (300) substantially between the outer layer (302) and the inner layer (312) where operational tubes (304), flexible tubes (306), push tubes (308), and support tubes (310) are disposed or contained. The lumen (318) may be used to deliver one or more surgical instruments or tools from the proximal portion of the elongate instrument (300) to the distal portion of the elongate instrument (300) where they maybe positioned and used to treat a target tissue structure inside a patient. The outer layer or outer tube (302) and the inner layer or inner tube (312) may be made of any flexible, pliable, or suitable polymer material or bio-compatible polymer material (e.g., nylon-12, plastic, Pebax®, Pellathane, Polycarbonate, etc.) or braided plastic composite structure. In some embodiments, outer layer or outer tube (302) and the inner layer or inner tube (312) may be one layer of material or one tube structure instead of separate layers of material or separate tube structures. Operational tubes (304) may not be actual tubes but may be the minor, secondary, or peripheral lumens or channels through the body of the outer layer or outer tube (302) or the operational tubes (304) may be separate operational tube structures that are disposed inside the minor, secondary, or peripheral lumens or channels in the body structure of the outer layer or outer tube (302). The operational tubes (304) may be made of any suitable polymer material, biocompatible polymer material or metallic material (e.g., polyimide, stainless steel or spiral cut stainless steel, Nitinol, etc.). The separate operational tubes (304) may be melted and/or braided into the wall of the minor, secondary, or peripheral lumens of the outer tube (302) or inner tube (312). The operational tubes (304) may provide a substantially slidable surface and interface for the flex tubes (306), such that the flex tubes (306) may slide substantially freely about the interior of the operational tubes (304) in a substantially decoupled configuration. In some embodiments, a distal end or portion of the flex tubes (306) may be fixedly coupled to the elongate instrument. In some variations, a proximal end or portion of the flex tubes may also be fixedly coupled to the elongate instrument (300) as in a passively controlled configuration of the flex tubes (306).

For example, in a passively controlled configuration, the flex tubes (306) may passively slide along the interior of the operational tubes as the elongate instrument or catheter (300) is navigated through the anatomy, articulated or steered. As will be discussed in more detail, the slidable interface between the flex tubes (306) and the operational tubes (304) together with buffer loops of the flex tubes in the control unit substantially decouple the flex tubes (306) from the elongate instrument or catheter (300). Because of the decoupled configuration of these two structures, articulation forces supported by the flex tubes may be decoupled from at least a portion of the catheter body or structure (300). As a result of decoupling the flex tubes (306) from at least a portion the catheter body or structure, articulation forces applied to articulate or steer the distal portion of the elongate instrument or catheter (300) may not be transmitted through or along the body of the elongate instrument from the distal portion to the proximal portion of the elongate instrument, for example. Consequently, as described in this example, articulation forces may be prevented or minimized from compressing the proximal portion of the elongate instrument or catheter body; such compression if allowed to occur, may affect the stiffness or bending stiffness of the proximal portion of the catheter. In addition, this decoupling of the articulation forces for the elongate member allows that changes in the shape or length of the elongate member as it is navigated through the anatomy may not have any impact or minimal impact on the articulation performance of the distal section of the elongate instrument. As will be also discussed in more detail, in some embodiments, the flex tubes (306) may also be utilized as support or reinforcing structures to vary or change the stiffness and/or bend radius of at least a portion of the catheter. In particular, the flex tubes (306) may be very effective support or reinforcing structures when they are compressed and stiffened. In other words, an elongate instrument (300) or a section of the elongate instrument without any flex tubes (306) may be substantially flexible. With the introduction of one or more flex tubes (306) into the body of the elongate instrument or a section of the elongate instrument, the elongate instrument or the section of the elongate instrument with the flex tubes (306) may become less flexible; even though the flex tubes (306) are flexible, they still have inherent axial stiffness, lateral stiffness, and bending stiffness. When the flex tubes (306) are compressed, such as using pull wires to apply a compressible force or load to the flex tubes, for example, they may become substantially more stiff laterally, such that the stiffened structures may affect or alter the stiffness and/or bend radius of at least a portion of the catheter where the flex tubes (306) are located. Accordingly, the flex tubes (306) may be utilized to vary or change the stiffness and/or bend radius of a portion or certain portion of the catheter by changing the positioning or placement of the flex tubes (306) in the elongate instrument (300). For example, the flex tubes (306) may be moved from one portion of the elongate instrument or catheter to another portion of the catheter. The portion from which where the flex tubes (306) were moved may become substantially more flexible or pliable without the flex tubes (306). Whereas, the portion to which where the flex tubes (306) were moved to may become substantially more stiff or less flexible or pliable. Consequently, the changes of stiffness along various portions of the elongate instrument or catheter may substantially affect the bend radius of at least a portion of the elongate instrument as pull wires are operated to articulate or steer the elongate instrument.

Referring back to the structural make up of the steerable instrument (300) as illustrated in FIG. 3A, the flex tubes (306) may be made from a coil of wire, a stack of rings, or a tube with spirally cut features. As may be appreciated, a substantially stiff tube may become less stiff or more flexible or more pliable as a spiral cut or spirally cut feature is imparted onto a substantially stiff tube. The tube may be made from a of a high durometer plastic such as Peek™ or stainless steel or other suitable material. One of the features of the flex tube (306) is that it may provide structural support to the elongate instrument (e.g., axial and lateral support) as well as being substantially flexible (e.g., able to bend in various directions and orientations). In some embodiments, the flex tubes (306) may be constructed from one continuous coil of wire, e.g., coil tube. In some other embodiment, the flex tube (306) may be constructed from a stack of rings, e.g., ring tube. For a ring tube, the rings may be stacked, grouped, or maintained together in any suitable manner. In some of the embodiments, the rings may be stacked, grouped, or maintained together by a substantially flexible sleeve, sheath, membrane, or covering. The coil of wire or rings may be made from a polymer material or metallic material. For example, a coil wire or rings may be made from stainless steel, Nitinol, etc. The coil wire may be made from a round stock or a flat stock or a stock having any cross-section or profile. Similarly, the rings of the ring tube may be made from a round stock or a flat stock or a stock having any cross-section or profile. In accordance with embodiments of the present invention, the flex tubes (306) may be generally constructed from a substantially tightly wound coil of wire or a stack of rings.

Still referring to FIG. 3A, the support tubes (310) may be made of any suitable polymer material, bio-compatible polymer material, or metallic material (e.g., polyimide, stainless steel, Nitinol, etc.). The inner layer or inner tube (312) may be made of any suitable polymer material or bio-compatible polymer material (e.g., nylon-12, plastic, Pebax®, Pellathane, Polycarbonate, etc.). In addition, the elongate instrument (300) may include a control ring (316) that may be secured near a distal portion of the elongate instrument (300). In various embodiments, the proximal end or portion of one or more pull wires (314) may be operatively coupled to various mechanisms (e.g., gears, pulleys, etc.) of a control unit or splayer of the instrument assembly (108). The pull wire (314) may be a metallic wire, cable or thread, or it may be a polymeric wire, cable or thread. The pull wire (314) may also be made of natural or organic materials or fibers. The pull wire (314) may be any type of suitable wire, cable or thread capable of supporting various kinds of loads without deformation, significant deformation, or breakage. The distal end or portion of one or more pull wires (314) may be anchored or mounted to the control ring (316), such that operation of the pull wires (314) by the control unit or splayer may apply force or tension to the control ring (316) which may steer or articulate (e.g., up, down, pitch, yaw, or any direction in-between) certain section or portion (e.g., distal section) of the elongate instrument (300). In other embodiments, no control ring may be used, instead the distal portion of the pull wires may be attached directly to a section or portion of the elongate instrument (300) where it may be steered, articulated, or bent. The wires may be crimped, soldered, welded or interlocked in any suitable manner to a specific location on a bending section or portion of the elongate instrument (300). The control ring (316) or the attachment point(s) may be located at any location, section, portion, or region along the length of the elongate instrument (300). Operation of the pull wires (314) may steer or articulate any of the location, section, portion, or region of the elongate instrument (300), which may in effect provide or define various bend radii for the articulated portion of the elongate instrument (300). In addition, in some embodiments there may be more than one control ring (316) mounted or installed to the elongate instrument (300) or more than one control wire attachment control locations, sections, or portions for controlling, steering, or articulating more than one section or portion of the elongate instrument (300). As will be described further, the flexible and steerable elongate instrument (300) having more than one control rings (316) or more than one control sections may be steered, articulated, or deflected into various complex shapes or curvatures (e.g., "S" curved shapes or "J" curved shapes, etc.). For example, the steerable elongate instrument (300) may be steered, articulated, or deflected into various complex shapes or curvatures that may conform to various complex shapes or curvatures of internal pathways of a patient to reach a target tissue structure of an organ inside the patient.

In some embodiments, one or more portions of the flex tubes (306) may be incorporated or coupled to the wall of the catheter (300) and such incorporation or coupling may be used for multiple functional purposes. For example, the coupling of the flex tubes (306) to the elongate instrument (300) may be used to support articulation forces as the elongate instrument or catheter is steered or articulated. As one or more of the pull wires (314) are operated by the control unit to steer or articulate the elongate instrument (300), the articulation or steering forces may be substantially transmitted along the body of the elongate instrument (300) from the portion (e.g., distal portion) of the elongate instrument (300) where the distal end or portion of the pull wires (314) may be anchored to the proximal portion of the elongate instrument (300). Since the flex tubes (306) are incorporated or coupled to the wall of the elongate instrument (300) and the flex tubes (306) are substantially configured to support axial loading, the articulation or steering loads may be decoupled from the elongate instrument (300) at the point or location where the flex tubes (306) are incorporated or coupled to the wall of the elongate instrument (300). Hence, the proximal portion of the elongate instrument may be substantially unaffected by the articulation or steering of the particular section or portion (e.g., distal section or portion) of the elongate instrument (300). The proximal portion of the elongate instrument may remain substantially flexible and pliable even when a particular portion (e.g., distal portion) of the elongate instrument is being articulated or steered. As such, an operator or surgeon may easily manipulate the elongate instrument (300) and urge it to conform, adopt, or match the various shape or curvatures of the internal pathways of a patient while the elongate instrument is being advanced and steered to reach various tissue structures or target sites inside a patient. in another example or application of the elongate instrument (300), the flex tubes (306) may be used as a structural support member to the catheter (300); in particular, when the flex tubes are stiffened by tensioning pull wires that may be attached to the flex tubes (306). In such application, the flex tubes (306) may support not only axial forces or loads, but also lateral forces or loads. As such, the flex tubes may increase the lateral as well as bending stiffness of at least a portion or section of the elongate instrument (300). In addition, the flex tubes (306) may also affect the bending radius of at least a portion or section of the elongate instrument (300) as the elongate instrument is steered, articulated, or manipulated.

Figure 3B:
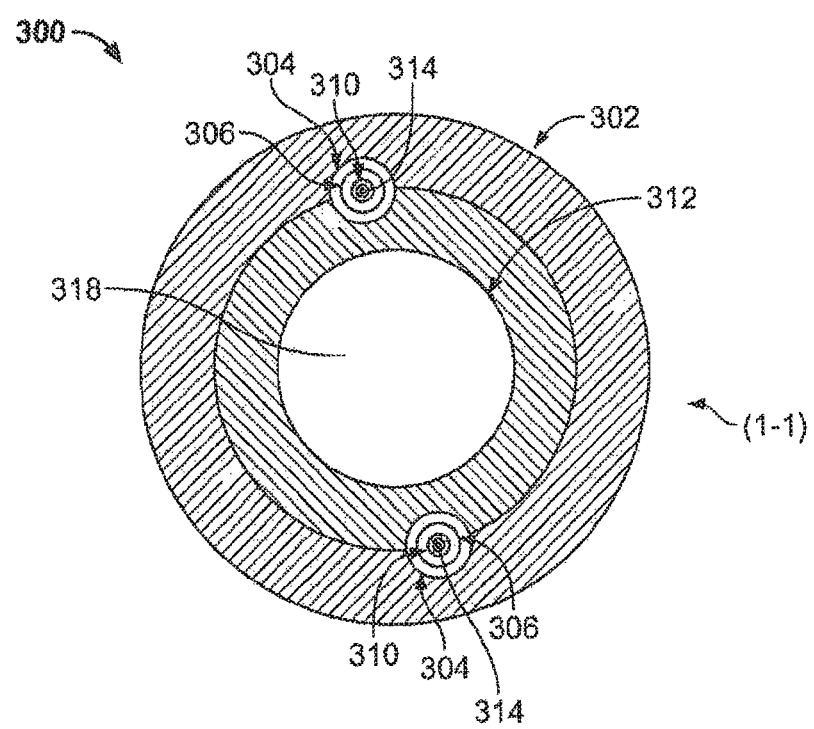
FIG. 3B illustrates another cross-sectional view (View 1-1) of a flexible and steerable elongate instrument with variable or changeable shape control and support elements in accordance with one embodiment.

FIG. 3B illustrates another cross-sectional view (View 1-1) of a section or portion of a steerable elongate instrument or catheter (300). As illustrated in FIG. 3B, the components of the elongate instrument (300) may be contained within or between the outer layer of material or outer tube (302) and the inner layer of material or inner tube (312). A primary, main, central, or working lumen (318) may be provided or defined by the inner layer of material or inner tube (312). The main lumen or central lumen (318) may be used to pass surgical instruments from the proximal end to the distal end of the elongate instrument (300) for performing various minimally invasive surgical procedures. Many of the components of the elongate instrument (300), e.g., operational tubes (304), flexible tubes (306), push tubes (308), and support tubes (310), are disposed within the minor, secondary, or peripheral lumens in the body structure of the elongate instrument, as illustrated in FIG. 3A and FIG. 3B. In some embodiments, one or more pull wires (314) may be disposed within lumens of the support tubes (310), lumens of the flex tubes (306), and lumens of the push tubes (308). As illustrated in FIG. 3A, the distal end or portion of the support tubes (310) may be secured or anchored near the distal portion of the elongate instrument (300) and the proximal end of the support tubes (310) may be slidably coupled to the distal end or portion of the flex tubes (306). In one embodiment, the distal portion of the flex tubes (306) may be secured at respective anchor points or regions (320) of the elongate instrument (300). Anchoring the flex tubes (306) to the elongate instrument (300) may provide the connections or couplings that allow force or load to be transferred from the flex tubes (306) to the elongate instrument (300) when force or load is applied to the flex tubes. For example, in some embodiments the flex tubes (306) may be actively controlled, that is one or more push tubes (308) or control members (308) may be configured to push against respective flex tubes (306). The applied force from the push tubes or control members (308) may be transmitted by way of the anchoring points (320) through the flex tubes (306) to the elongated instrument (300). In this way, at least a portion of the elongate instrument (300) may be steered or shaped by the push tubes or control members (308). Similarly, articulation or steering forces or loads may be transferred or coupled at the anchor points (320) from one portion (e.g., distal portion) of the elongate instrument (300) to the flex tubes (306), such that the flex tubes (306) may act as load bearing support elements for another portion (e.g., proximal portion) of the elongate instrument (300) where the force or load may be decoupled or not transmitted. In other words, the anchor points (320) may function as coupling points from one portion (e.g., distal portion) of the elongate instrument (300) to the flex tubes (306) where force or load may be transferred from one portion (e.g., distal portion) of the elongate instrument to the flex tubes. Similarly, the anchor points (320) may also function as decoupling points between one portion (e.g., distal portion) of the elongate instrument (300) to another portion (e.g., proximal portion) of the elongate instrument (300) where force or load may be decoupled or not transferred from one portion (e.g., distal portion) of the elongate instrument to another portion (e.g., proximal portion) of the elongate instrument. As will be discussed in more details, the location of the anchor points (320) may be varied to control the radius of curvature of a bending section of the elongate instrument (300) as the elongate instrument is articulated or steered. In some embodiments, the flex tubes (306) may be anchored at substantially the same points or regions of the elongated instrument (300). In some embodiments, the flex tubes (306) may be anchored at substantially different points or regions of the elongate instrument (300) to affect the bend radius of various portions of the elongate instrument (300) and/or various directions of steering or bending. The flex tubes (306) may be secured to the elongate instrument (300) in any suitable manner. In some embodiments, the distal portion of the flex tubes (306) may be fused with the material of the outer layer or outer tube (302), such as by thermal fusion. Similarly, the material of the outer layer or outer tube (302) may be fused to the flex tubes (306). For example, the flex tubes (306) may be fused to the outer layer or outer tube (302) at various places where it is not covered by the operational tubes (304), as illustrated in FIG. 3A. In some embodiments, the elongate instrument may be configured with displacement control of the flex members (306). That is a flex tube (306) may not be fixedly coupled to the elongate instrument, instead it may be displaced along the length of the elongate instrument (300). Once the flex tube (306) is displaced to a desired location, the distal portion of the flex tube (306) may be secured or coupled to the elongate instrument (300) by a deployable and retractable anchor. The displacement of proximal portion of the flex tube (306) may be controlled by the push tube or control member (308). The deployable anchor may be deployed to couple the flex tube (306) to a particular anchor point at a particular location on the elongate instrument. The anchor may also be retracted such that the flex tube (306) may be disengaged or separated from the elongate instrument (300) such that it may be displaced to a different location along the elongate instrument (300).

Passively Controlled Flex Member

Figure 4A:
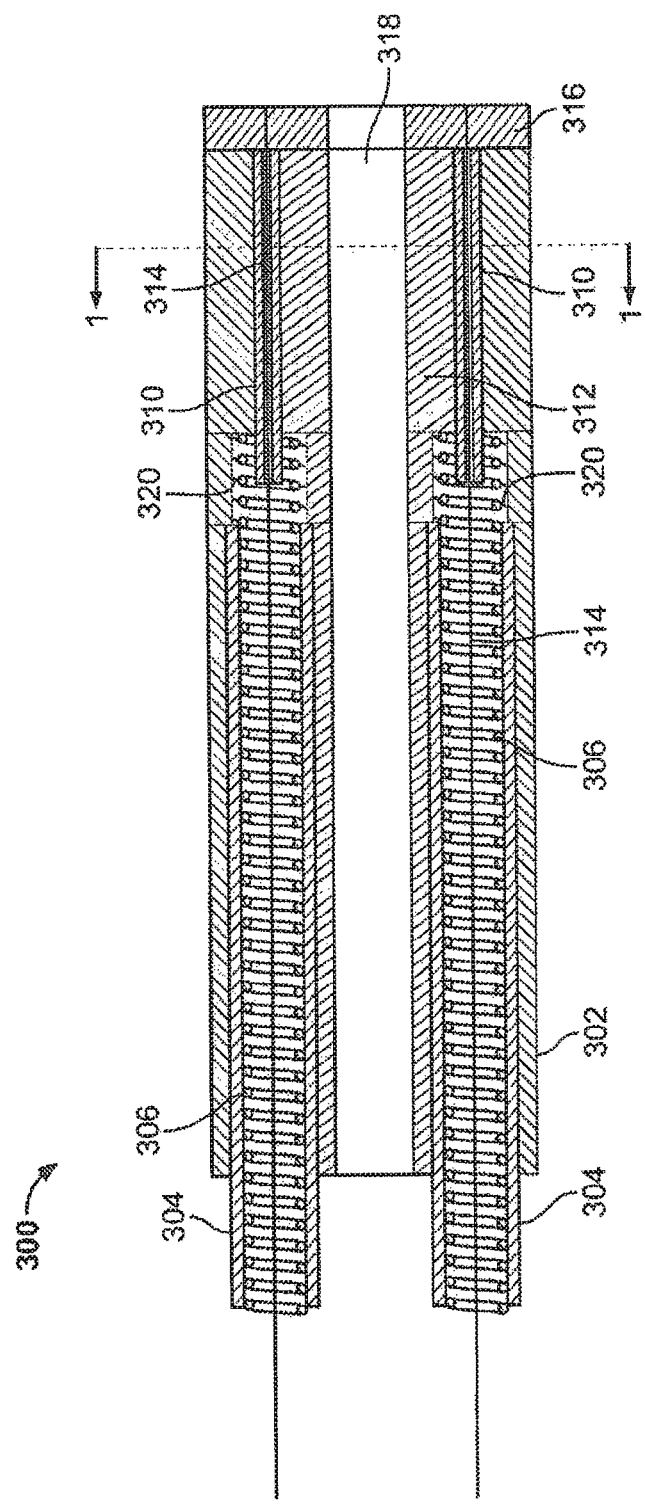
FIG. 4A illustrates an elongate instrument with passively controlled flex member in accordance with one embodiment.
Figure 4B:
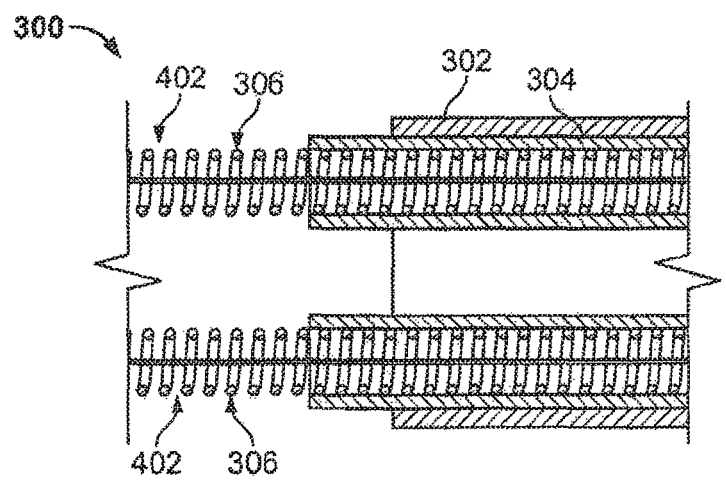
FIG. 4B illustrates a passively controlled flex member with a service or buffer loop in accordance with one embodiment.

As illustrated in FIG. 4A, an elongate instrument (300) with passively controlled flex members (300) may be similarly configured as the elongate instrument structure illustrated in FIG. 3A with the exception that the proximal portion of the flex members (300) may be fixedly coupled to the body of the elongate instrument, the control unit or splayer, or some other structural element or component. In some embodiments, the push tube or control member (308) may not be included as a component of the elongate instrument (300) for a passively controlled flex member. In the passively controlled configuration, the flex members (306) may include a service or buffer loop (402), as more clearly illustrated in FIG. 4B. The service loop or buffer loop (402) on the flex members (306) may provide the extra service length or buffer length needed for articulation as the elongate instrument (300) is pushed through the anatomy, articulated or steered.

Figure 4C:
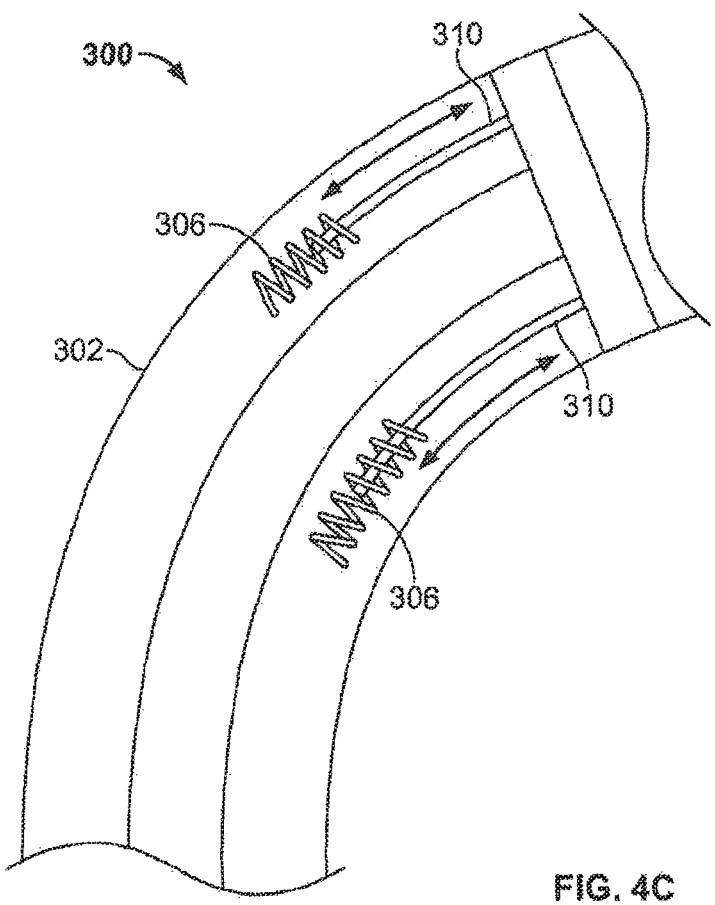
FIG. 4C illustrates support tubes or support members sliding along the flex tubes or flex members in accordance with one embodiment.

As the elongate instrument is pushed through the anatomy, steered or articulated, the support tubes (310) in the distal section may slide along the flex tubes (306) as indicated by the arrows in FIG. 4C. The support tubes (310) may provide a lumen or path for the pull wires (314) to connect to the distal section of the catheter. The support tubes (310) may also provide some amount of structural rigidity or support to the distal portion of the elongate instrument (300). In some embodiments, the elongate instrument (300) may not include any support tubes (310). In some embodiments, one or more flex tubes (306) may be extended further into the distal portion of the elongate instrument (300) to provide some structural rigidity or support to the distal portion of the elongate instrument. In some embodiments, the flex tubes (306) may be substantially more stiff or more rigid than the support tubes (310), such that when one or more flex tubes (306) are used as support structures to reinforce the distal portion of the elongate instrument (300), the distal portion of the elongate instrument may be substantially more stiff or more rigid than when it is supported by the support tubes (310). In some embodiments, the flex tube (306) may provide substantially the same or similar stiffness or structural support as the support tubes (310), such that there may not be any significant difference if the flex tubes (306) or support tubes (310) are used to provide structural support to the distal portion of the elongate instrument (300). In some embodiments, the flex tubes (306) may be substantially more flexible than the support tubes (310), such that the distal portion of the elongate instrument may be substantially more flexible or less rigid than when it is supported by the flex tubes (306).

Figure 4D:
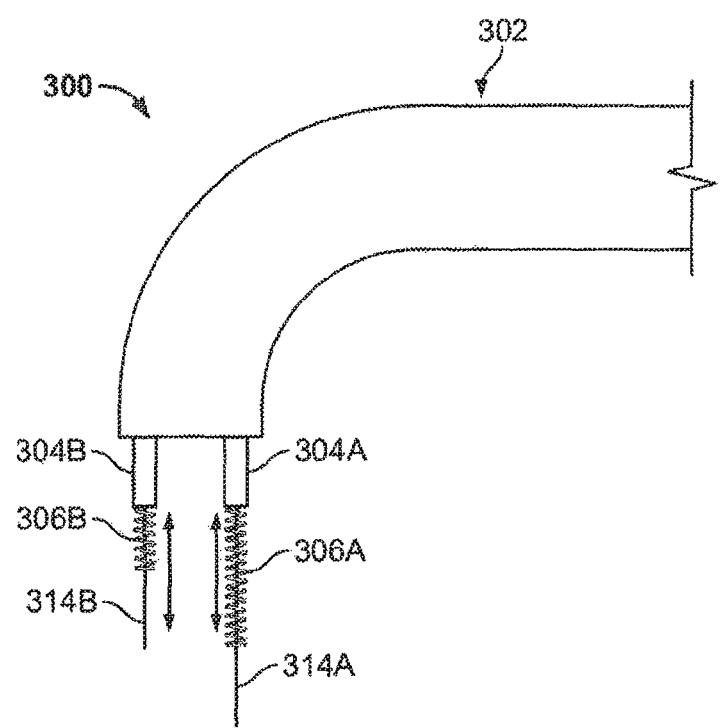
FIG. 4D illustrates slidable couplings of variable shape control and support components near the proximal section of a flexible and steerable elongate instrument in accordance with one embodiment.

Referring back to FIG. 4A, the flex tubes (306) may be slidably coupled to the operational tubes (304) while fixed at the distal end (320). As the elongate instrument (300) is steered or articulated, or as the catheter is advanced through the natural curvature of the body lumens, the flex tubes (306) may slide along the operational tubes (304) as indicated by the arrows illustrated in FIG. 4D. In one scenario, for example, the elongate instrument (300) may be steered by operating or applying tension to one of the pull wires (e.g., 314A) through operation of one or more gears and/or pulleys in the control unit or splayer. The tension on one of the pull wires (e.g., 314A) may cause the elongate instrument (300) to bend, as illustrated in FIG. 4D. The inside edge or inside region of the bend may be contracted or foreshortened, while the outside edge or outside region of the bend may be lengthened or stretched. The bend of the elongate instrument as described may cause one of the flex tubes (e.g., 306A) to slide "out" near the proximal portion of the elongate instrument (300) at the contracted or foreshorten edge or region. In this same example, another one of the flex tubes (e.g., 306B) may slide "in" near the proximal portion of the elongate instrument (300) at the lengthened or stretched edge or region, as illustrated in FIG. 4D. In order to accommodate the sliding of "in" and "out" of the flex tubes (306), the flex tubes may include a service loop or buffer loop (402) to allow for these "in" and "out" displacements or movements of the flex tubes (306). As discussed, the flex tubes (306) may be passively constrained or restrained. The flex tubes (306) may be constrained or restrained by being coupled to the elongate instrument (300), the control unit, or splayer. In addition, the flex tubes (306) may be constrained or restrained by hard-stops, tethers, etc. In some embodiments, the operational tubes (304) may be configured or allowed to float or slide substantially freely relative to the outer layer or outer tube (302). In some other embodiments, the operational tubes (304) may not be configured or allowed to float or slide substantially freely relative to the outer layer or outer tube (302).

Actively Controlled Flex Member

Figure 5A:
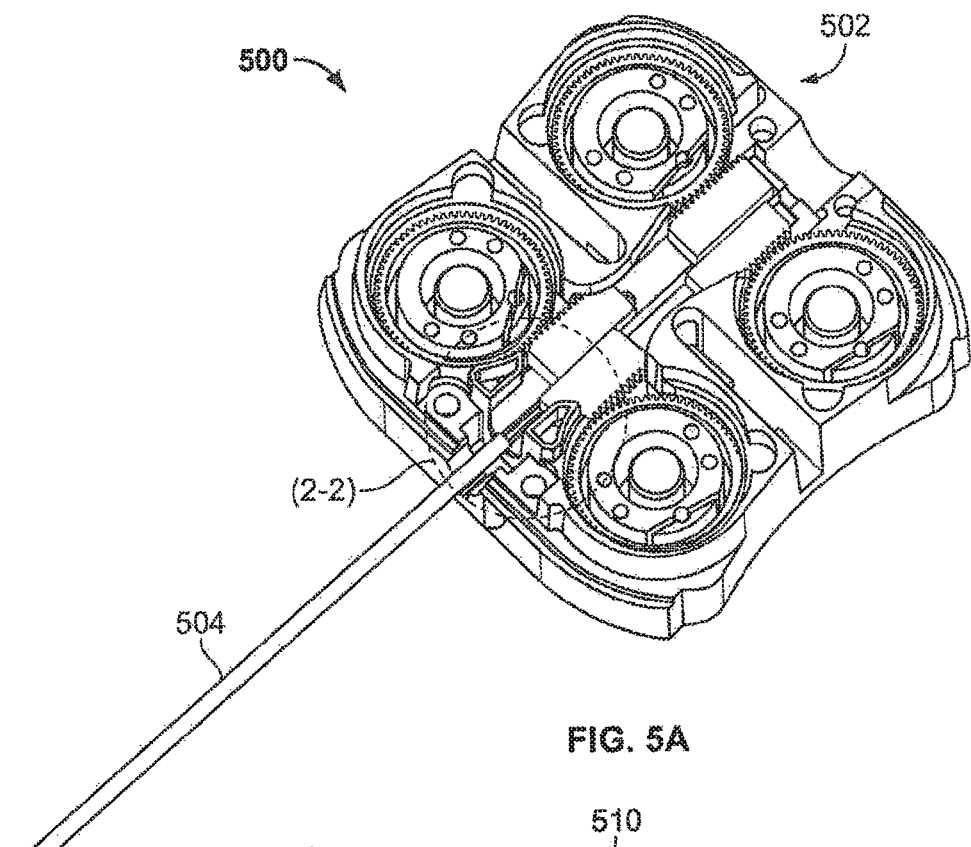
FIG. 5A through FIG. 5D illustrate rack and pinion drive mechanisms in a drive unit or splayer for variable shape control and support in accordance with one embodiment.
Figure 5B:
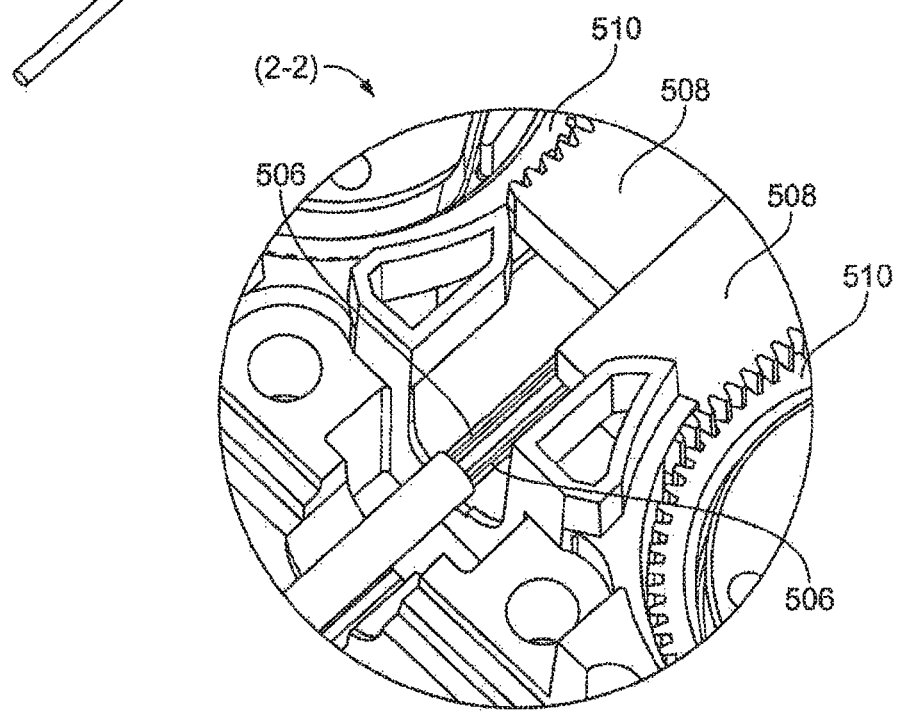

In some embodiments, the flex member (306) of an elongate instrument may be actively controlled. For example, the distal portion of the flex member (306) may be coupled to the body of an elongate instrument, while the proximal portion of the flex member (306) may be displaced or moved by various control mechanisms or members of the elongate instrument assembly or system. In some embodiments, the proximal portion of the flex members (306) may be displaced by push tubes or control members. The push tubes or control members may be operated by mechanisms of an instrument assembly, control unit, or splayer of an elongate instrument assembly or catheter system. A control unit or splayer in an elongate instrument assembly or catheter system may include drive mechanisms that are configured to operate or drive the push tubes or control members. In one example, as illustrated in FIG. 5A through 5D, the drive mechanisms in a control unit (502) of a catheter system (500) may include racks (508) and pinions (510) for operating or driving the push tubes (506) or control members (506). In some embodiments, the pinions (510) may be operated by output torque provided by the instrument driver (106) of a robotic or telerobotic surgical system (100). In some embodiments, the pinions (510) may be operated by output torque provided by various mechanical or manually operated systems. Other drive mechanisms may also be configured to operate or drive the push tubes, e.g., rotary gears, worm gears, linear gears, etc. FIG. 5A illustrates an exposed view of a control unit or splayer (502) of an elongate instrument assembly or catheter system (500). A close-up view (View 2-2) of the control unit (502) is illustrated in FIG. 5B. As illustrated in FIG. 5B in View 2-2, push tubes (506) or control members (506) may be controlled or driven by racks (508) and pinions (510) in a "forward" or "backward" manner, movement or displacement, so as to apply or release force exerted onto the flex tubes (506) of a steerable elongate instrument or catheter (504). As the racks (508) are driven "forward", the flex tubes (506) may be driven forward and they may also be compressed in the axial direction. The "forward" displacement of the flex tubes (506) may apply an axial load to the distal section of the elongate instrument or catheter (504). This axial load may cause the distal section of the catheter (504) to bend, deflect, steer, or articulate at a particular position or location of the catheter. Since the flex tubes (506) may be anchored or secured at the distal section, compression force applied at the proximal section by the racks (508) may cause at least a portion, e.g., distal portion, of the elongate instrument or catheter (504) to bend, deflect, steer, or articulate in response to the compression force exerted by the racks (508) and form a particular induced shape or orientation. Accordingly, active control of the push tubes (506) may allow "shaping" or putting the elongate instrument or catheter (504) into various shapes or curvatures. The elongate instrument or catheter (504) or portion (e.g., proximal portion) of the catheter (504) may be induced and then locked in place by the push tubes (506) into various shape or curvatures that may substantially match the natural pathways or anatomy where the elongate instrument or catheter may be used in a minimally invasive procedure. In addition, another portion (e.g., distal portion) of the catheter may be articulated or steered by pull wires to navigate the catheter (504) through torture pathways inside the patient.

Figure 5C:
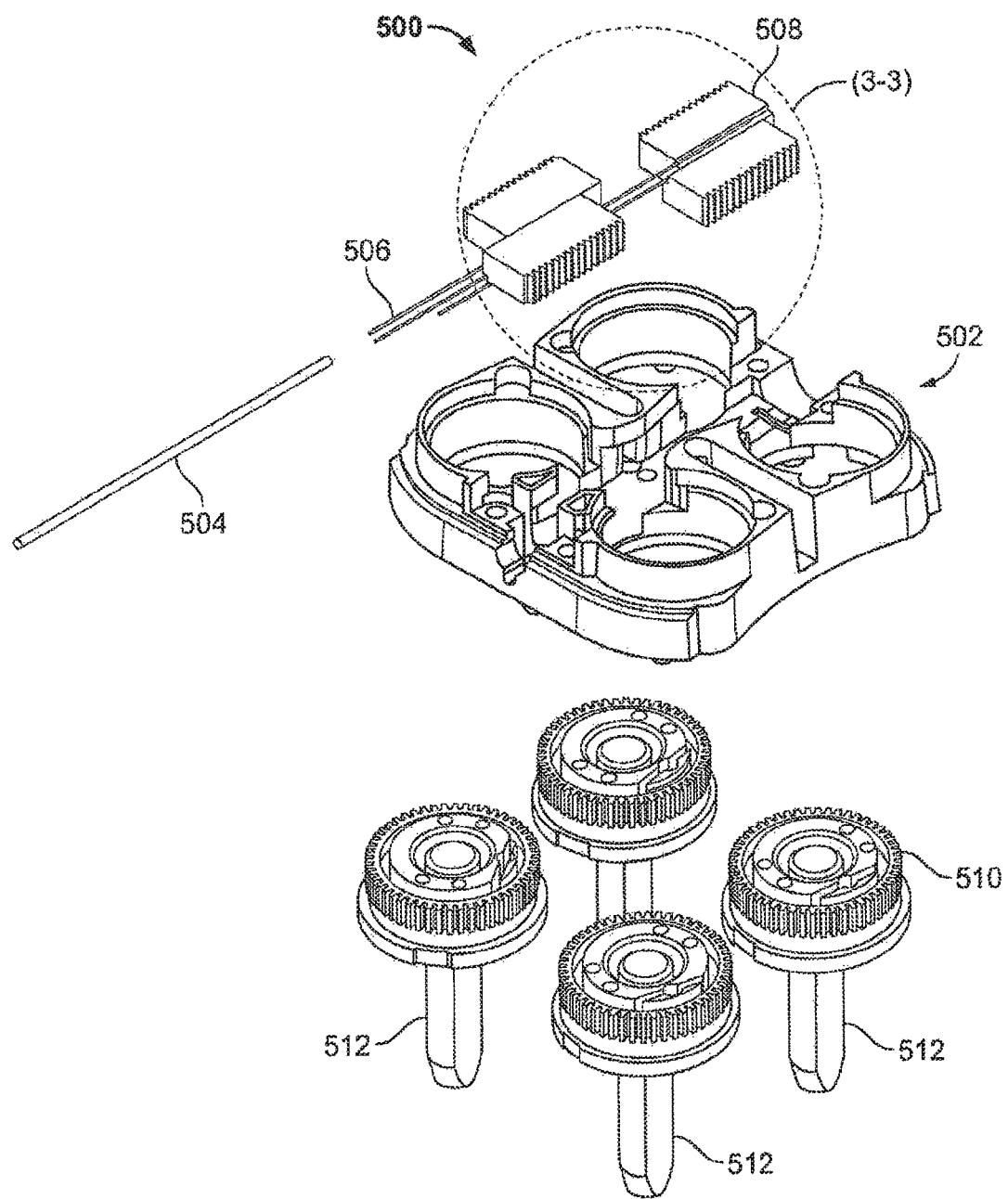
Figure 5D:
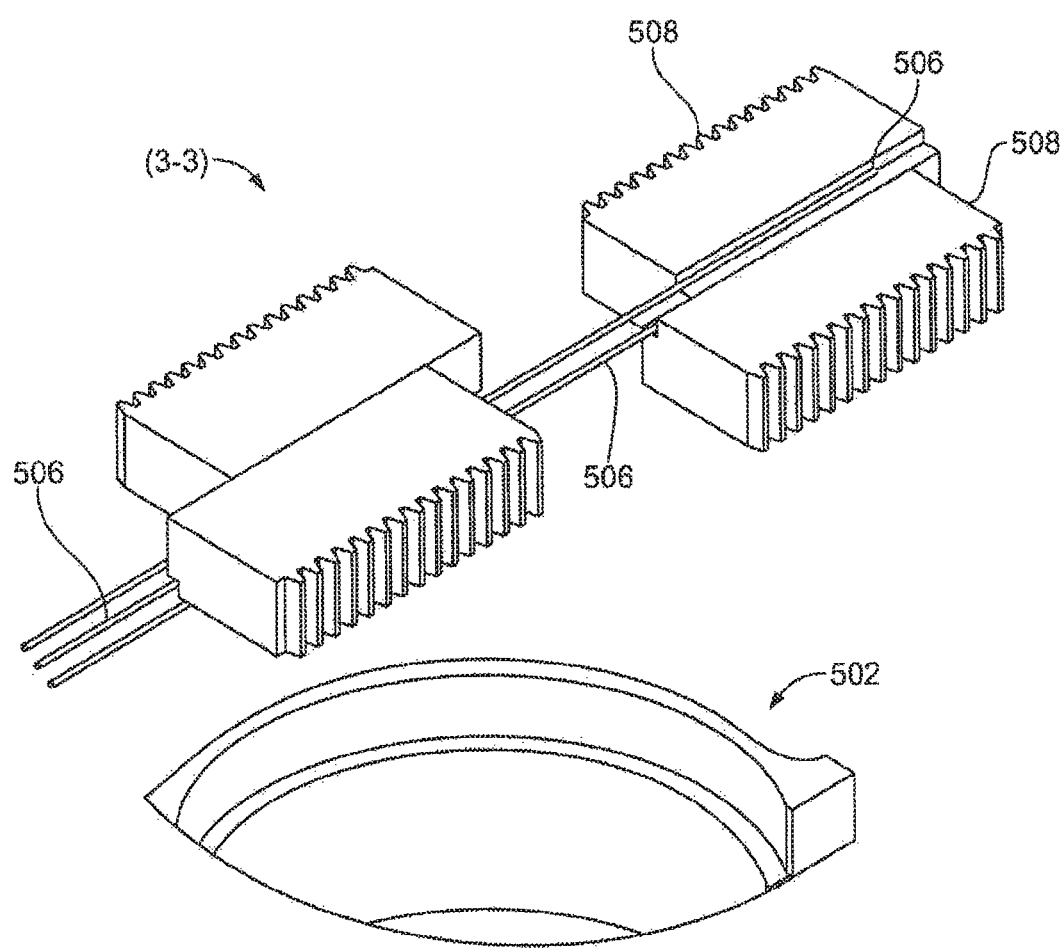

FIG. 5C illustrates another exposed view of a catheter system (500). As illustrated in FIG. 5C, drive pins (512), which may be engaged to a torque output system (e.g., instrument driver), provide the necessary torque or motion to operate the pinions (510) for controlling or driving the racks (508) in a "forward" or "backward" manner, movement, or displacement. The forward and backward movements of the racks (508) may be used to actively control or operate the push tubes (506). FIG. 5D illustrates a close-up view (View 3-3) of the racks (508) and push tubes (506). The drive mechanisms in the instrument driver may operate each set of racks (508) and pinions (510) independently or in concert in a coordinated manner. As such, the push tubes or control members (506) may be operated independently or in concert in a coordinated manner to apply or release force or tension on the flex tubes (506).

FIG. 6A through FIG. 6C illustrate the operation of a substantially flexible and steerable elongate instrument in accordance with one embodiment. FIG. 6A illustrates an elongate instrument (600) of an instrument assembly in a substantially neutral state. In this example, the elongate instrument (600) includes an outer body (602), two sets of support tubes (not shown), operational tubes (604A and 604B), flex tubes (606A and 606B), and pull wires (608A and 608B). Each set of support tubes, operational tubes (604A and 604B), flex tubes (606A and 606B), and pull wires (56A and 568B) may be substantially axially aligned, and the pull wires (608A and 608B) may be coupled to a control ring (not shown) or mounting points that are located at the distal section or portion of the elongate instrument (600). As illustrated in FIG. 6A, in the neutral state the flex tubes (606A and 606B) and pull wires (608A and 608B) may extend out of the operational tubes (604A and 604B) at about the same amount or distance. As the substantially flexible and steerable elongate instrument (600) is advanced into the anatomy and natural pathway (e.g., blood vessel, gastrointestinal tract, etc.) of a patient, it may take on the shape of the natural pathway, as illustrated in FIG. 6B. In this example, the proximal section (610) of the elongate instrument may be bent at a curvature induced by the natural pathway (e.g., blood vessel, gastrointestinal tract, etc.), while the distal section (620) may remain relatively straight or in a substantially neutral state. Due to the bend at the proximal section (610), the flex tube (606A) and pull wire (608A) may slide "out" of the operational tube (604A) near the inside edge or inside region of the bend as it may be contracted or foreshortened, as indicated by the arrow illustrated in FIG. 6B. At the same time, due to the bend at the proximal section (610), the flex tube (606B) and pull wire (608B) may slide "in" to the operational tube (604B) near the outside edge or outside region of the bend as it may be lengthened or stretched, as indicated by the arrow illustrated in FIG. 6B. As may be appreciated, it may be advantageous to maintain the induced shape or curvature of the proximal section (610) of the elongate instrument (600) and at the same time articulate or steer the distal section (620) of the elongate instrument (600) to treat a target site or toward a different direction down the natural pathway. As illustrated in FIG. 6C, the shape or curvature of the proximal section (610) of the elongate instrument (600) may be maintained or locked by securing the distal ends of the flex tubes (606A and 606B) into the position they have acquired due to the induced shape or bend of the proximal section (610). The flex tubes (606A and 606B) may be locked in place by using the active control feature of the instrument assembly provided by the various mechanisms (e.g., rack and pins, drive gears, etc.) in the control unit or splayer. While the elongate instrument (600) may be inherently substantially flexible, the elongate instrument or portion of the elongate instrument may become substantially stiff or rigid when the flex tubes are compressed or locked through active control. Once the flex tubes are locked in place, they may become substantially stiff or rigid structures or platforms. As the flex tubes have been locked in place to maintain the induced shape or curvature of the proximal section (610), pull wires (608A and 608B) may be operated to steer or articulate the distal section (620) of the elongate instrument (600). In this example, pull wire (608B) may be pulled or tensioned, as indicated by the arrow illustrated in FIG. 6C, to steer the distal section (620) in a substantially opposite direction of the bend in the proximal section (610). The pull wire (608A) may be relaxed, as indicated by the arrow illustrated in FIG. 6C, to accommodate for the bend at the outside edge or outside region of the bend of the distal section (620). In addition, the bending force or load of the distal section (620) may be substantially absorbed or transferred from the elongate instrument through the flex tube attachment points and then to the flex tubes (606A and 606B), which may be further transferred to the control unit or splayer of the instrument assembly. The proximal section (610) of the elongate instrument (600) may not be affected by the steering or articulation forces applied by the pull wire to steer the distal section (620) of the elongate instrument (600).

In another example, as illustrated in FIG. 7A through FIG. 7C, the proximal section (610) of the elongate instrument may be bent at a curvature induced by the bending, steering, or articulation of the distal section (620) of an elongate instrument (600). FIG. 7A illustrates an elongate instrument (600) of an instrument assembly in an initial substantially neutral state. In this example, the elongate instrument (600) includes an outer body (602), two sets of support tubes (not shown), operational tubes (604A and 604B), flex tubes (606A and 606B), and pull wires (608A and 608B). Each set of support tubes, operational tubes (604A and 604B), flex tubes (606A and 606B), and pull wires (608A and 608B) may be substantially axially aligned, and the pull wires (608A and 608B) may be coupled to a control ring (not shown) or mounting points that are located at the distal section or portion of the elongate instrument (600). As illustrated in FIG. 7A, in the neutral state the flex tubes (606A and 606B) and pull wires (608A and 608B) may extend out of the operational tubes (604A and 604B) at about the same amount or distance. The substantially flexible and steerable elongate instrument (600) may be steered or articulated at the distal section by operation of the pull wires (608A and 608B), as illustrated in FIG. 7B. In this example, the proximal section (610) of the elongate instrument may be bent at a curvature induced by the bending, steering or articulation at the distal section (620). The induced bend and curvature at the proximal section (610) may be locked in place by using the active control feature of the instrument assembly provided by the various mechanisms (e.g., rack and pins, drive gears, etc.) in the control unit or splayer as previously described. While the elongate instrument (600) may be a substantially flexible instrument, the proximal section (610) may become substantially stiff or rigid as the flex tubes (606A and 606B) are locked in place, and proximal section (610) may become a substantially rigid platform to support the manipulation or articulation of the substantially flexible distal section (620). As a result, the flex tubes may act as support structures of the elongate instrument. The ability to lock various sections of the elongate instrument into particular shapes or curvatures by means of the flex tubes allow the elongate instrument to be manipulated into substantially complex shapes or curvatures (e.g., "S" shaped curves, "J" shaped curves, etc.). In this example, pull wire (608B) may be pulled or tensioned, as indicated by the arrow illustrated in FIG. 7C, to steer the distal section (620) in a substantially opposite direction of the bend in the proximal section (610).

In other embodiments of an elongate instrument where flex tube or similar control or support structure may not be used, operating or tensioning a pull wire on the outside edge of a bend may cause the elongate instrument to rotate or twist as the pull wire may tend to rotate the distal section of the elongate instrument until the pull wire is at the inside edge of the bend; this rotation or twist phenomenon or occurrence is known as curve alignment. Embodiments of the present invention may substantially eliminate this problem by providing support structures such as flex tubes that could prevent curve alignment and substantially prevent or eliminate unwanted rotation or twist of the catheter. In other words, the pull wires, flex tubes, and the distal anchor points of the pull wires at the control ring or the body of the elongate instrument may all be substantially aligned, such that operating or tensioning of the pull wires would allow the elongate instrument to bend in a substantially aligned or neutral configuration with the longitudinal axis of the pull wire and flex tube. In this configuration, there may not be any component or vector of force or load that could cause the elongate instrument to rotate or twist resulting in curve alignment as the elongate instrument is steered or bent. FIG. 8A and FIG. 8B illustrate one embodiment of an elongate instrument or catheter (800) that substantially eliminate or prevent curve alignment and the catheter may be biased, steered, or articulated in specific planes, e.g., X-Plane, Y-Plane, Z-Plane, of articulation by using flex tubes as support structures or "backbones" that may be in substantial alignment with a neutral axis. As illustrated in FIGS. 8A and 8B, the pull wires may be substantially aligned with the neutral axes, e.g., in the X-Y Planes. In FIG. 8A, as a pull wire is operated (indicated by the arrow) to steer the elongate instrument, the flex tube supports the pull wire, maintain its alignment to the longitudinal axis, and prevent it from moving to the inside edge of the bend, which may produce a force vector that could cause the elongate instrument to twist or rotate. In this example, the operation of the pull wire causes the distal section of the elongate instrument to be steered or articulated in a substantially upward movement, e.g., the direction or vector of articulation is in the Y-Plane. Similarly, as illustrated in FIG. 8B, as a pull wire is operated (indicated by the arrow) to steer the elongate instrument, the flex tube supports the pull wire, maintain its alignment to the longitudinal axis, and prevent it from moving to the inside edge of the bend, which may produce a force vector that could cause the elongate instrument to twist or rotate. In this example, the operation of the pull wire causes the distal section of the elongate instrument to be steered or articulated in a substantial sideway or rightward movement, e.g., the direction or vector of articulation is in the X-Plane.

Figure 9:
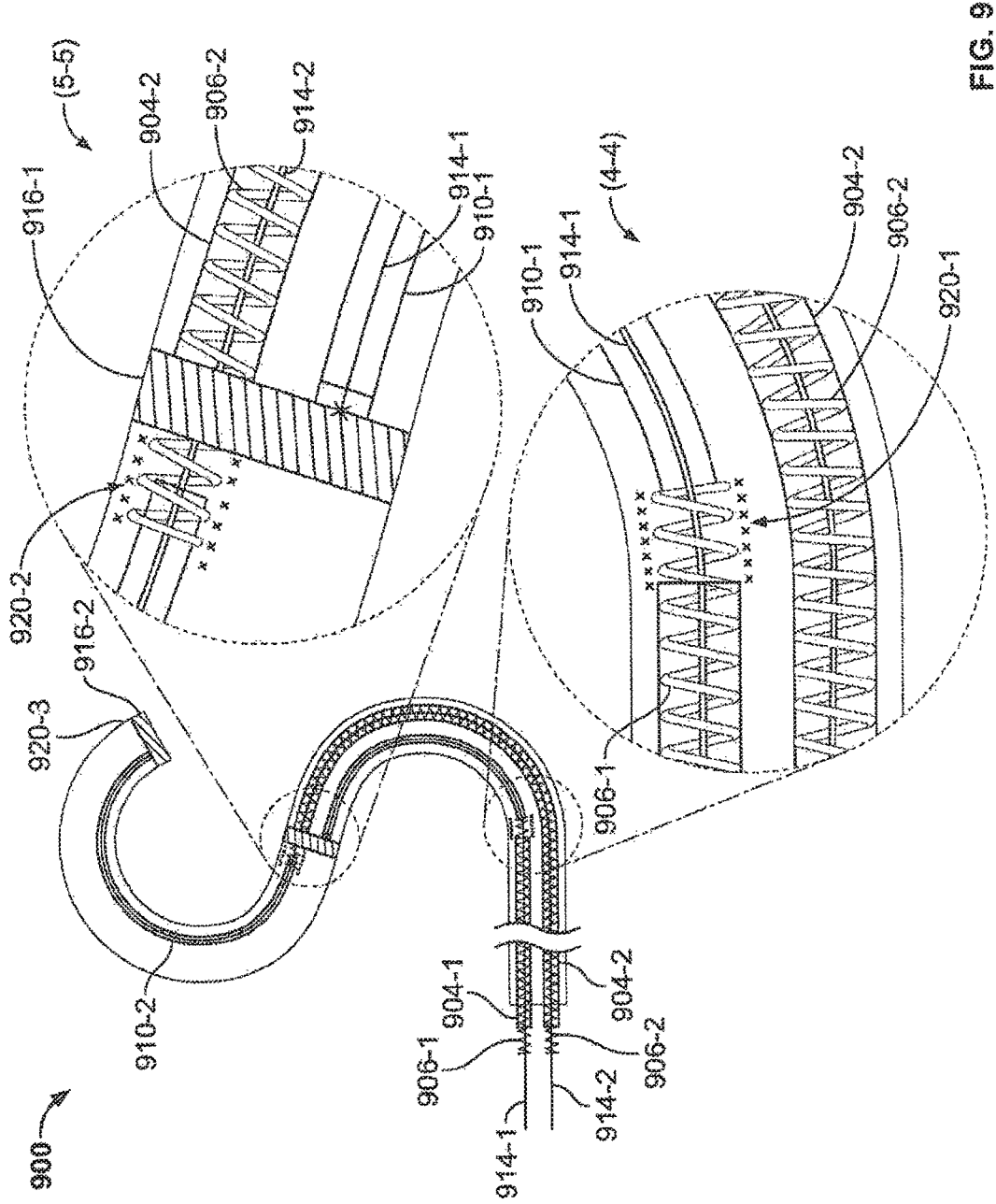
FIG. 9 illustrates the mechanics of variable shape control and support features of a flexible and steerable elongate instrument in which an "S" shaped curve may be formed in accordance with one embodiment.

As described, embodiments of the present invention may allow a flexible and steerable elongate instrument to execute various movements necessary to form variable or changeable shapes and curvatures. For example, FIG. 9 illustrates one embodiment in which a complex "S" shaped curvature may be formed with an elongate instrument (900). In this example, the elongate instrument (900) may include a first flex tube (906-1) which may be disposed inside a lumen of a first operational tube (904-1). The first operational tube (904-1) may terminate near a first anchor point or region (920-1), where the first flex tube (906-1) may be secured, fused, or bonded to the material of the elongate body (900), as illustrated in a first detail view (View 4-4) of FIG. 9. A first pull wire (914-1) may be disposed through a lumen of the flex tube (906-1) and a first support tube (910-1), wherein the proximal end of the first pull wire (914-1) may be operatively coupled to a control unit or splayer (not shown) and the distal end of the first pull wire (914-1) may be anchored to a control ring (916-1) or an anchor point on the body of the elongate instrument (900), as illustrated in a second detail view (View 5-5) of FIG. 9. The support tube (910-1) may be slidably coupled to the first flex tube (906-1), such that it may slide along the surface of the first flex tube as the elongate instrument is steered or articulated. The elongate instrument (900) may include a second flex tube (906-2) which may be disposed inside a lumen of a second operational tube (904-2). The second operational tube (904-2) may terminate near a second anchor point or region (920-2), where the second flex tube (906-2) may be secured, fused, or bonded to the material of the elongate body (900), as illustrated in the second detail view (View 5-5). A second pull wire (914-2) may be disposed through a lumen of the second flex tube (906-2) and a second support tube (910-2), wherein the proximal end of the second pull wire (914-2) may be operatively coupled to a control unit or splayer (not shown) and the distal end of the second pull wire (914-2) may be anchored to a second control ring (916-2) or an anchor point on the body of the elongate instrument (900), as illustrated in FIG. 9. The second support tube (910-2) may be slidably coupled to the second flex tube (906-2), such that it may slide along the surface of the second flex tube as the elongate instrument is steered or bent. Although two flex tubes and associated components are illustrated in FIG. 9, additional number of flex tubes and associated components, e.g., 2 or more sets of flex tubes and associated components, may be used to steer and control the movement as well as the shape of the elongate instrument.

As illustrated in FIG. 9, the first or lower portion of the "S" may be formed by the proximal portion of the elongate instrument (900). The lower portion of the "S" may be obtained by operating the first pull wire (914-1) to steer the proximal portion of the elongate instrument (900) into a curvature that resembles the shape of the lower portion of the "S" shape. The lower portion of the "S" shape formed by the proximal portion of the elongate instrument may be locked in place by locking the second flex tube (906-2) in the position it has acquired by various control means (e.g., active control mechanisms of the control unit or splayer). Once the proximal portion of the elongate instrument has been locked in place, the second pull wire (714-2) may be operated to steer or bend the distal portion of the elongate instrument (900) into a curvature that resembles the upper portion of the "S" as illustrated in FIG. 9.

Figure 10:
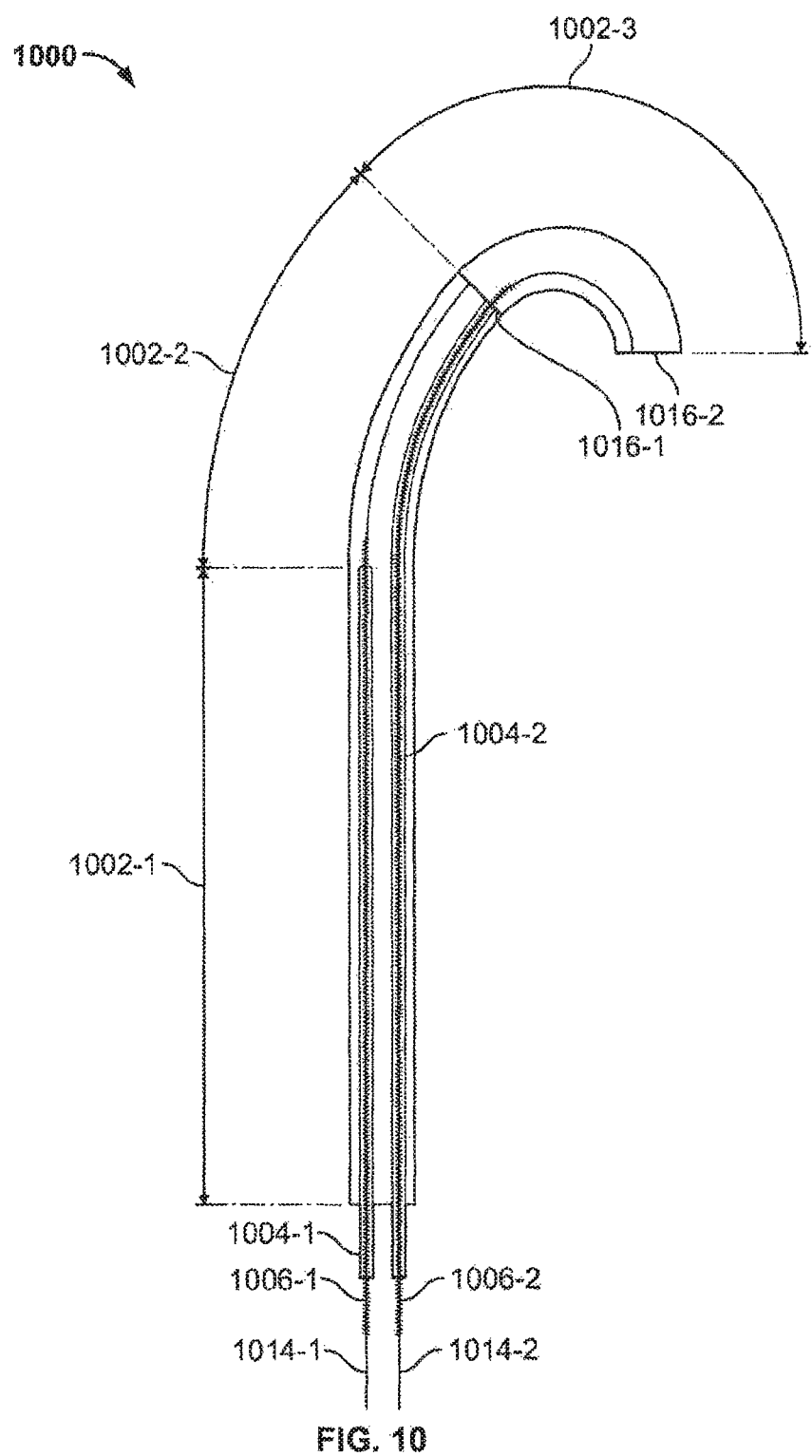
FIG. 10 illustrates the mechanics of variable shape control and support features of a flexible elongate instrument in which a "J" shaped curve may be formed in accordance with one embodiment.

Another complex shape may be formed by an elongate instrument in accordance with another embodiment. FIG. 10 illustrates a complex "J" shaped curvature formed by an elongate instrument (1000). In this example, the elongate instrument (1000) may include two set of flex tubes and their associated components. As illustrated in FIG. 10, the "J" shaped curvature may be formed from three sections of the elongate instrument (1000). The first section (1002-1) may be substantially straight to form the straight portion of the "J", the second section (1002-2) may form a first bend section of the first curvature or initial curvature of the "J", and the third section (1002-3) may form the second bend of the second or final curvature of the "J". As illustrated in FIG. 10, the elongate instrument (1000) may include two flex tubes (1006-1 and 1006-2). The first flex tube (1006-1) may operate as a support structure to provide the support (e.g., lateral stiffness or support) necessary to form or maintain the straight portion of the "J". Similar to the construction of other embodiments as previously described, the distal end of flex tube (1006-1) may be anchored to the elongate body near the distal section of first section (1002-1) of the elongate body where it may not be covered by the operational tube (1004-1). Active control as previously described may be used to apply force or load to compress the flex tube (1006-1), such that the flex tube may become a substantial rigid or stiff structure. Since compression force was applied to the flex tube (1006-1) when it was in a substantially neutral state without having been deflected, steered, or articulated, the flex tube (1006-1) may be maintained or stiffened in its neutral or substantially straight configuration. In its compressed or substantially stiffened or rigid state, the flex tube (1006-1) may be used to support the deflection or articulation of the second section (1002-2) of the elongate instrument. The second section (1002-2) may be deflected or articulated by operating the pull wire (1014-1). The distal end of the pull wire (1014-1) may be anchored to a control ring (1016-1) or an anchoring point near the distal portion of the second section (1002-2). The proximal end of the pull wire (1014-1) may be operatively coupled to a control unit or splayer (not shown) that operates the pull wire. Once the desired curvature of the second section (1002-2) is achieved, the shape of the curvature may be locked in place by compressing and/or locking the second flex tube (1006-2) in place using active control as previously described. The distal end of the second flex tube (1006-2) may be anchored to the elongate instrument near the distal portion of second section (1002-2) where it may be exposed out of the second operational tube (1004-2). Once the second flex tube (1006-2) is locked in place and becomes a substantially stiffened or rigid structure, the second pull wire (1014-2) may be operated to steer or articulate the third section (1002-3) into the desired curvature to form the "J" shape. The distal end of the second pull wire (1014-2) may be anchored to the second control ring (1016-2) or to an anchor point on the elongate body near the distal portion of the third section (1002-3). The proximal end of the second pull wire (1014-2) may be operatively coupled to a control unit or splayer (not shown) that operates the pull wire. Although two examples of complex shapes or curvatures may be formed by a flexible and steerable elongate body with variable or changeable shape control and support elements as illustrated and described, many other complex shapes or curvatures may be form by an elongate body in accordance with various embodiments of the present invention.

Displaceable Flex Member

Figure 11A:
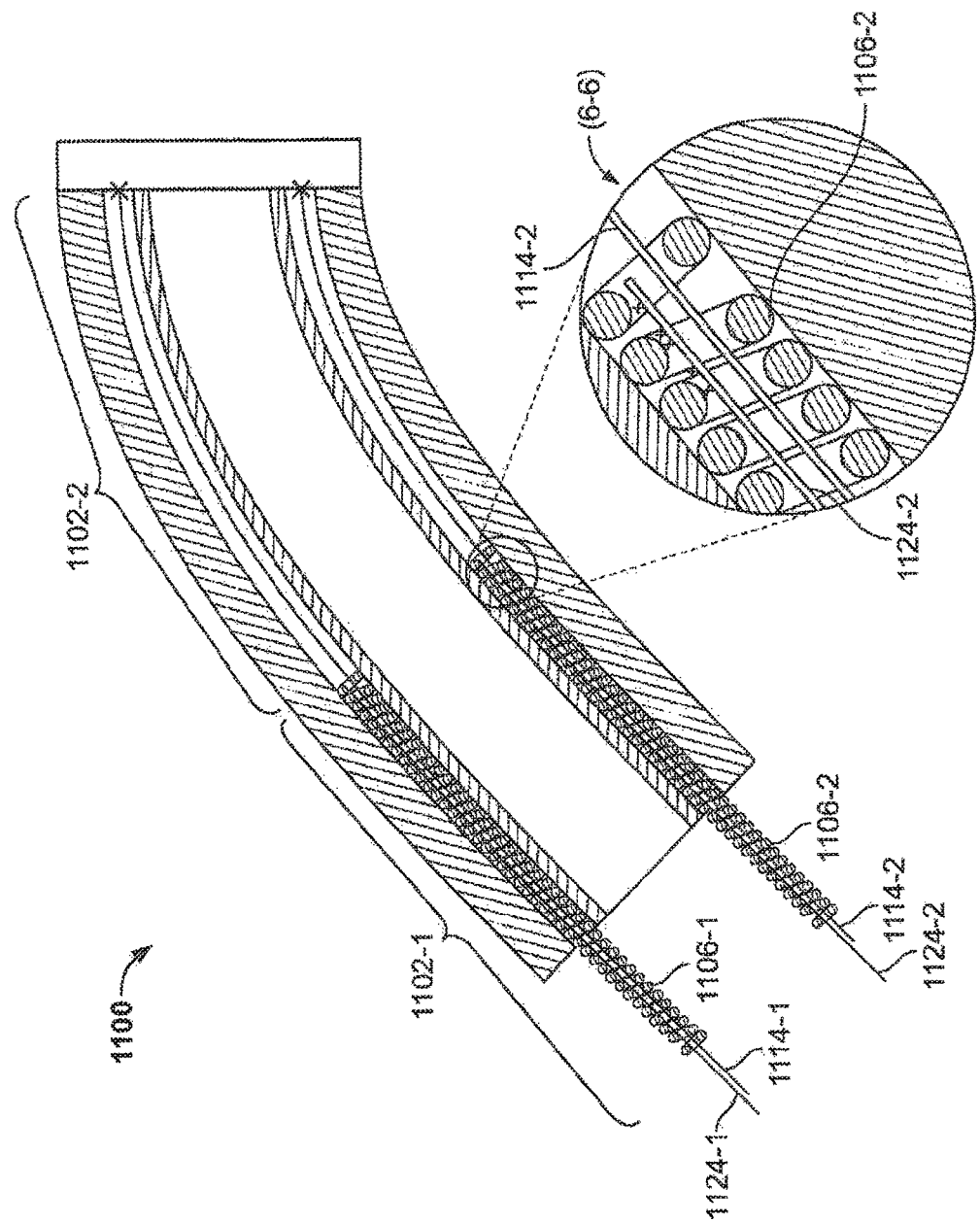
FIG. 11A illustrates one embodiment of an elongate instrument with movable or displaceable flex tubes in accordance with one embodiment.

FIG. 11A illustrates another embodiment of a flexible and steerable elongate instrument in accordance with another embodiment of the present invention. In this embodiment, the flex tubes (1106-1 and 1106-2) may be allowed to slide along the length of the elongate instrument (1100). That is, the flex tubes (1106-1 and 1106-2) may not be fixedly secured to the elongate instrument (1100), instead the flex tubes may include a deployable and retractable anchor that allows the flex tubes to be displaced. As such, the position of the flex tubes (1106-1 and 1106-2) may be changed substantially along the length of the elongate instrument (1100). The positions of the flex tubes (1106-1 and 1106-2) may be changed by operating various pull wires (1124-1 and 1124-2), push tubes (not shown), and active control elements. Pull wires (1124-1 and 1124-2) may be secured near the distal portion of the flex tubes (1106-1 and 1106-2), as illustrated in detail view (View 6-6), and the pull wires (1124-1 and 1124-2) may be used to control the displacement of the flex tubes. The other pull wires (1114-1 and 1114-2) may be extended and coupled to a control ring or the distal portion of the elongate instrument for steering or articulating the distal section of the elongate instrument. The pull wires may be flat wires, round wires, or wires having any suitable shape, cross section, or profile. Because the flex tubes (1106-1 and 1106-2) may not be secured, they may be moved or pushed further toward the distal portion of the elongate instrument (1100) by the respective push tubes or pulled back toward the proximal portion of the elongate instrument (1100) by the respective pull wires (1124-1 and 1124-2). The ability to move the flex tubes along the length of an elongate instrument provides greater variability and control of the possible shapes or curvatures that may be formed with the elongate instrument. In addition, the displacement of the flex tubes may also change the stiffness (e.g., lateral stiffness, bending stiffness) of at least a portion of the elongate instrument. The displacement of the flex tubes as it may affect the stiffness of at least a portion of the elongate instrument may also change or affect the radius of curvature of a least a portion of the elongate instrument as the elongate instrument is articulated or steered. By using the drive mechanisms in the control unit or splayer, the flex tubes (1106-1 and 1106-2) may be moved separately or in concert in a coordinated manner.

Figure 11B:
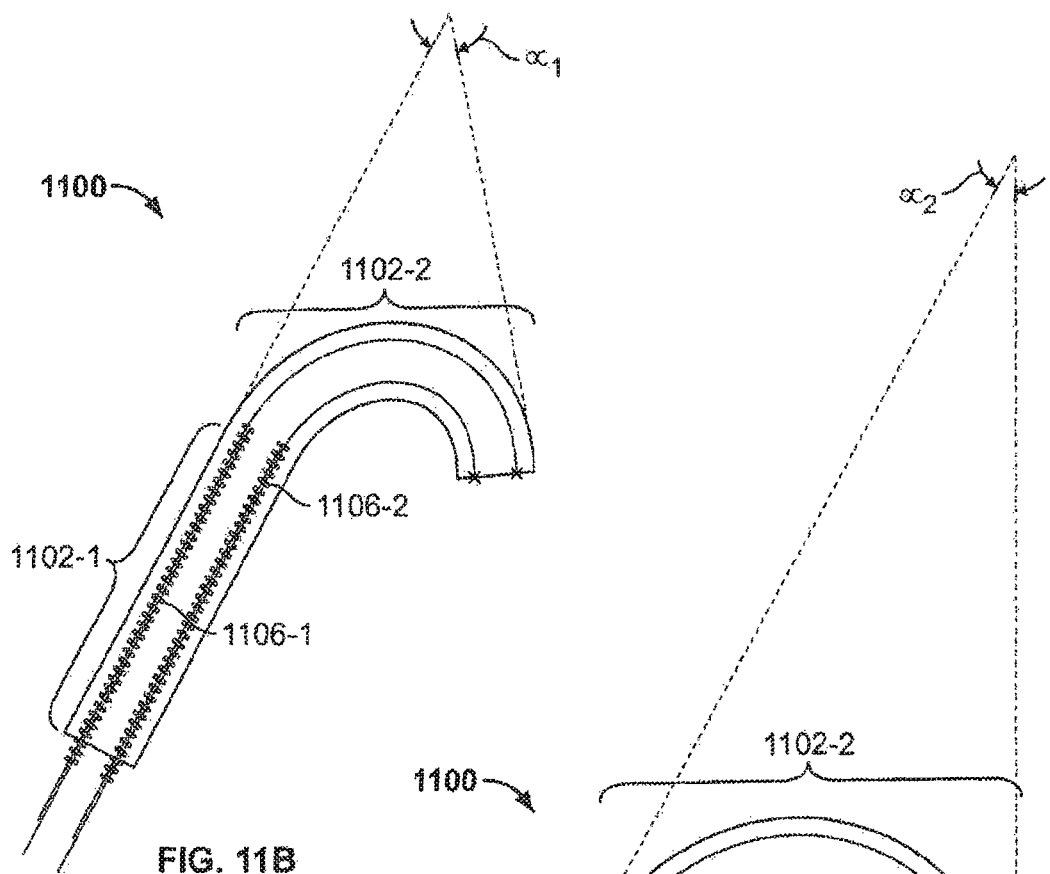
FIG. 11B and FIG. 11C illustrate how movable flex tubes may change the properties of an elongate instrument to form various shapes and/or curvatures in accordance with one embodiment.
Figure 11C:
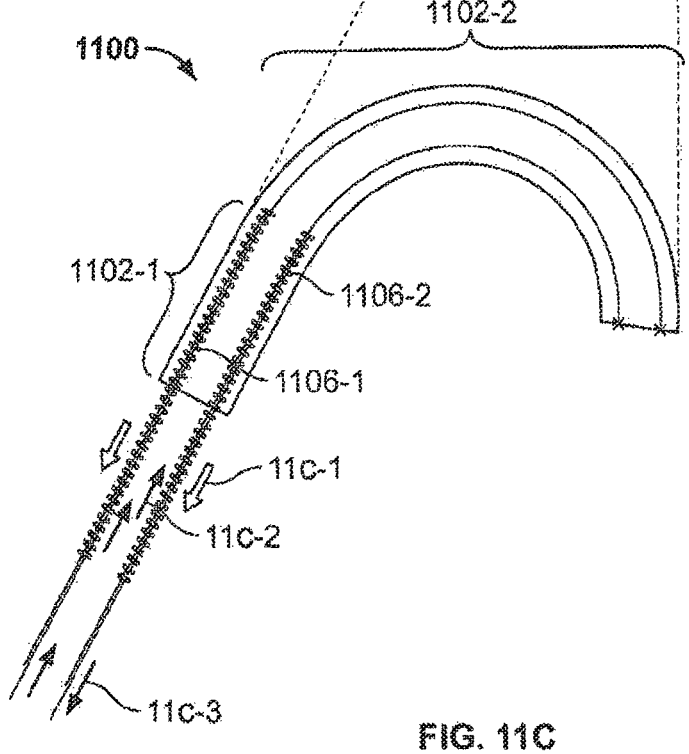

FIG. 11B and FIG. 11C illustrate one example of moving or displacing the flex tubes to alter the variability, shape, or curvature of an elongate instrument (1100) as well as an angle of trajectory (a) between two sections or portions of the elongate instrument (1100). As illustrated in FIG. 11B, the flex tubes (1106-1 and 1106-2) may be positioned along the length of the elongate instrument (1100) up to the location near the distal portion of the first section (1102-1). As illustrated in FIG. 11C and indicated by the first set of arrows (11C-1), the flex tubes (1106-1 and 1106-2) may be moved back toward the proximal end of the elongate instrument (1100). As illustrated, the first section (1102-1) of the elongate instrument (1100) may have become substantially shorter as compared to its initial state as illustrated in FIG. 11B when the same or substantially the same amount of force may be applied to steer or articulate the distal end or portion (1102-2) of the elongate instrument (1100). Correspondingly, the second section (1102-2) may have become substantially longer as compared to its initial state as illustrated in FIG. 11B. In addition, an angle of trajectory (a1) between the first section (1102-1) and the second section (1102-2), as illustrated in FIG. 11B, may have also changed to a different angle of trajectory (a2), as illustrated in FIG. 11C. As the flex tubes (1106-1 and 1106-2) are moved back toward the proximal end of the elongate instrument (1100), the distal portion of the elongate instrument has lost some of it support and rigidity provided by the flex tubes (1106-1 and 1106-2). As a force or load is applied to steer or articulate the elongate instrument (1100), the less supported or more flexible distal portion of the elongate instrument may form a substantially larger or longer arc or curvature as illustrated by a substantially larger or longer second section (1102-2) in FIG. 11C, than the arc or curvature that may be obtained in its initial state illustrated in FIG. 11B. Accordingly, changing the position or location of the flex tubes along the length of an elongate instrument may allow the elongate instrument to change its characteristic properties of being able to form various shapes and/or curvatures as well as angle of trajectory (a) between two sections, portions or segments of elongate instrument. As illustrated in this example, displacement of the flex tubes (1106-1 and 1106-2) may alter the stiffness of a portion of the elongate instrument (1100). As the flex tubes (1106-1 and 1106-2) have certain amount of axial and lateral stiffness, displacing the flex tubes may affect the stiffness, e.g., axial and lateral stiffness, of at least a portion of the elongate instrument (1100). As may be appreciated, the variation or change of stiffness of a portion of the elongate instrument may affect the radius of curvature of at least a portion of the elongate instrument as force or load is applied to steer or articulate the elongate instrument. The displaced flex tubes may be locked in-place by using a deployable and retractable anchor in combination with push tubes or control members. The anchor then allows the flex tubes to serve as passive coils and absorb or bear the articulation loads and isolate or decouple the elongate body from the articulation loads. As such, the altered shape, curvature, and/or angle of trajectory (a) of the elongate instrument may be maintained for various purposes. For example, the altered shape, curvature, and/or angle of trajectory (a) may be maintained to facilitate advancement of the elongate instrument through a particular section of a tortuous pathway. in addition, the altered shape, curvature, and or angle of trajectory (a) may be maintain to facilitate advancement of certain objects, surgical instrument, etc. through a working lumen of the elongate instrument to a target tissue structure inside a patient.

The overall stiffness of at least a portion of the elongate instrument may be further altered or changed by compressing the flex tubes (1106-1 and 1106-2). The second set of arrows (11C-2) indicates that compression forces may be applied to stiffen the flex tubes (1106-1 and 1106-2) and provide substantially rigid structures to support steering or articulation of the second section (1102-2) of the elongate instrument (1100) by operating the pull wires (1114-1 and 1114-2) as indicated by the third set of arrows (11C-3) in FIG. 1 IC as the flex tubes (1106-1 and 1106-2) are supported by corresponding push tubes or control members (not shown).

Deployable and Retractable Anchor

Figure 12A:
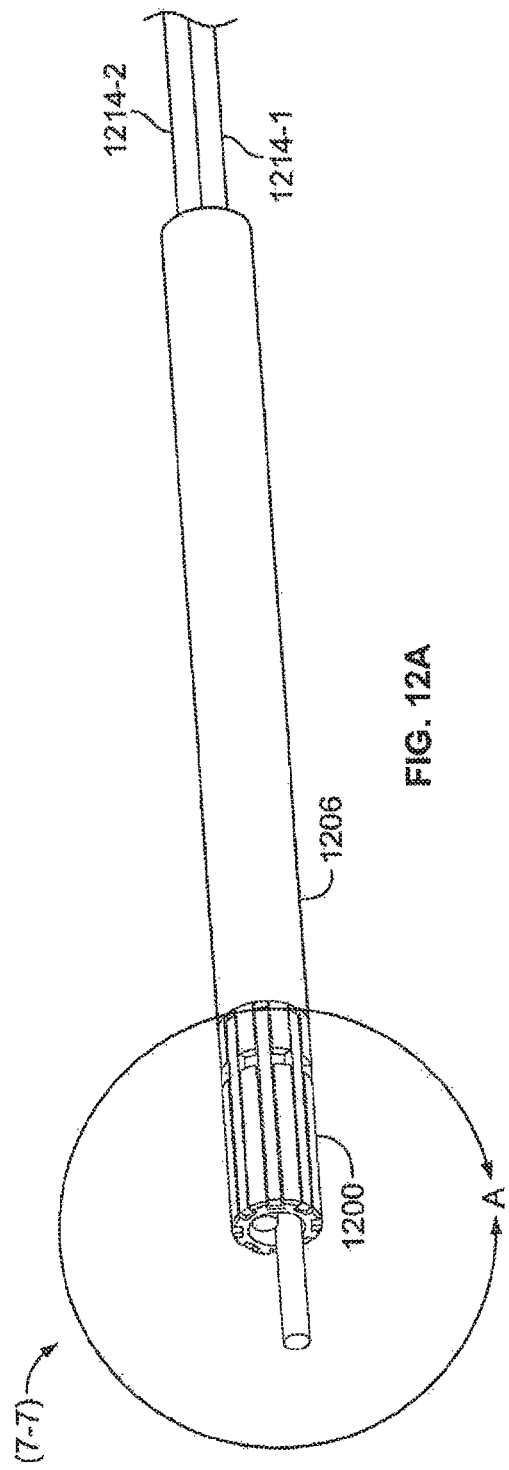
Figure 12B:
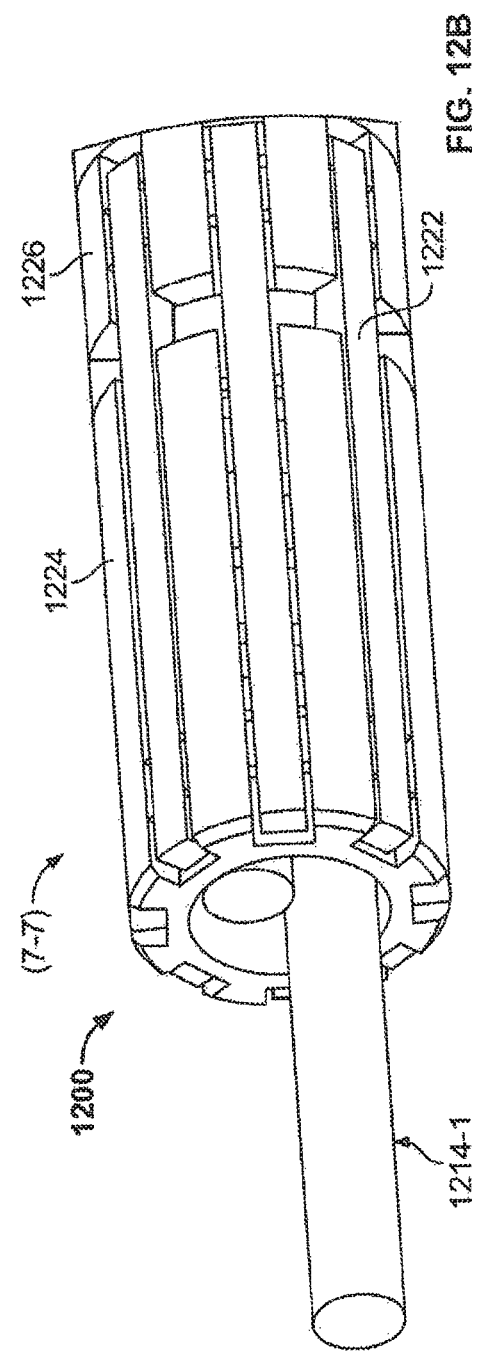
Figure 12E:
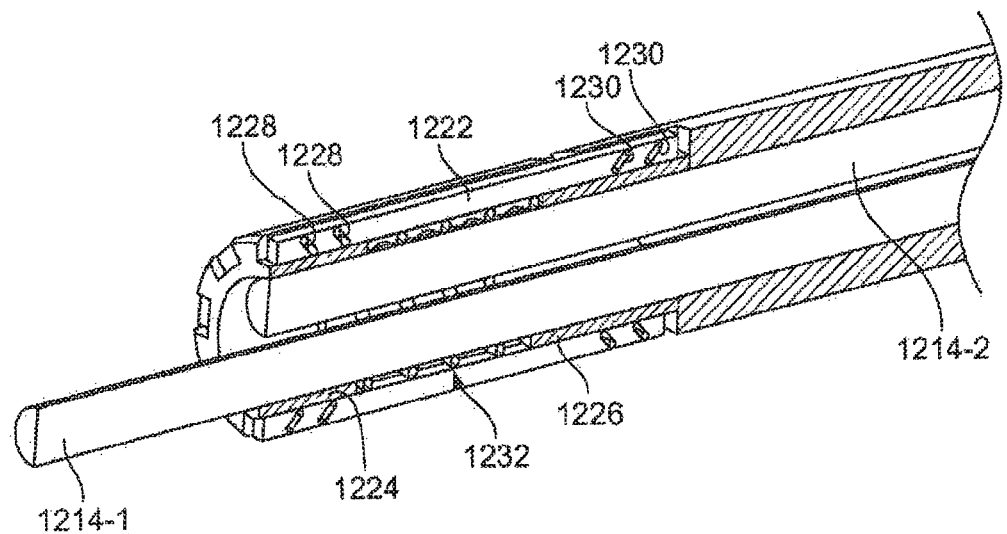
Figure 12F:
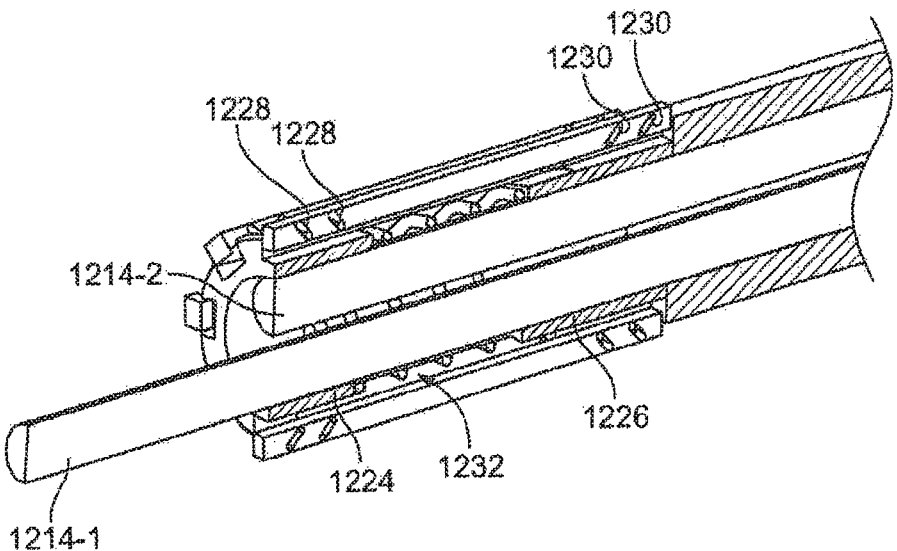

FIG. 12A through FIG. 12F illustrate one embodiment of a deployable and retractable anchor for a displaceable flex tube or flex member of an elongate instrument. FIG. 12A illustrates the deployable and retractable anchor (1200) in its neutral state. That is, the anchoring mechanisms may not be deployed. FIG. 12B illustrates a close-up view of the deployable anchor (1200) in its neutral state, as shown in detail view (View 7-7). FIG. 12C illustrates the deployable anchor (1200) in its activated state. That is, the anchoring mechanisms are deployed or extended in engagement or coupling mode. FIG. 12D illustrates a close-up view of the deployable anchor (1200) in its activated state, as shown in detail view (View 8-8). Referring back to FIG. 12A, the deployable and retractable anchor (1200) may be coupled to a distal end or portion of a flex tube (1206). A distal end of an anchor wire or pull wire (1214-2) may be coupled to the deployable anchor (1200) and a proximal end of the anchor wire or pull wire (1214-2) may be coupled to a control unit (not shown). The control unit may be configured to operate the anchor wire (1214-2) to activate the deployable anchor (1200), such as tensioning the anchor wire, as well as operate the anchor wire (1214-2) to de-activate the deployable anchor, such as releasing the tension on the anchor wire. The anchor wire (1214-2) may be configured to operate the mechanisms of the deployable anchor, such as the distal anchor puck (1224) to operate various cam pins (1228) to travel along the cam pathways (1230) and then displace the anchoring cams (1222) to engage or disengage the deployable anchor (1200) from the body of the elongate instrument or catheter (not shown). The anchoring cams (1222) may be displaced upward to engage the body of the elongate instrument or downward to disengage the anchor (1200) from the body of the elongate instrument or catheter. A pull wire or control wire (1214-1) may be disposed through the flex member (1206) and the deployable anchor (1200) to a distal portion of the elongate instrument for steering or articulating the elongate instrument. As shown in more detail in FIG. 12E and FIG. 12F, distal anchor puck (1224) and proximal anchor puck (1226) support the anchor wire (1214-2). As the anchor wire is operated, e.g., tensioned by a control unit or splayer, the distal anchor puck (1224) may be displaced toward the proximal portion of the anchor (1200). The displacement of the anchor puck (1224) toward the proximal portion of the anchor (1200) may cause the cam pins (1228) to travel along the cam pathways (1230) which may cause the anchoring cams (1222) to be displaced upward to engage or couple the anchor (1200) to the body of the elongate instrument or catheter. The location of engagement or coupling becomes an anchoring point of the flex tube (1206) to the elongate instrument or catheter. In addition, as the anchor wire (1214-2) is operated or tensioned, the cam spring (1232) may be compressed in the activated state. When the anchor wire (1214) is operated to release the tension on the anchor wire (1214-2), the cam spring (1232) pushes the distal anchor puck (1224) toward the distal portion of the anchor (1200). The displacement of the anchor puck (1224) toward the distal portion of the anchor (1200) may cause the cam pins (1228) to travel along the cam pathways (1230) which may cause the anchoring cams (1222) to be displaced downward to disengage or detach the anchor (1200) from the body of the elongate instrument or catheter. The deployable anchor may be restored to its neutral or undeployed state. In the neutral state, the flex member (1206) may be displaced along the length inside a lumen of the elongate instrument or catheter, such as inside the operation tube. The flex member (1206) may be displaced by activating a pull wire that may be coupled to the flex member to pull the flex member (1206) toward the proximal portion of the elongate instrument or by activating push tubes or control members to displace or push the flex member toward the distal portion of the elongate instrument.

Splayer or Control Unit

Figure 13A:
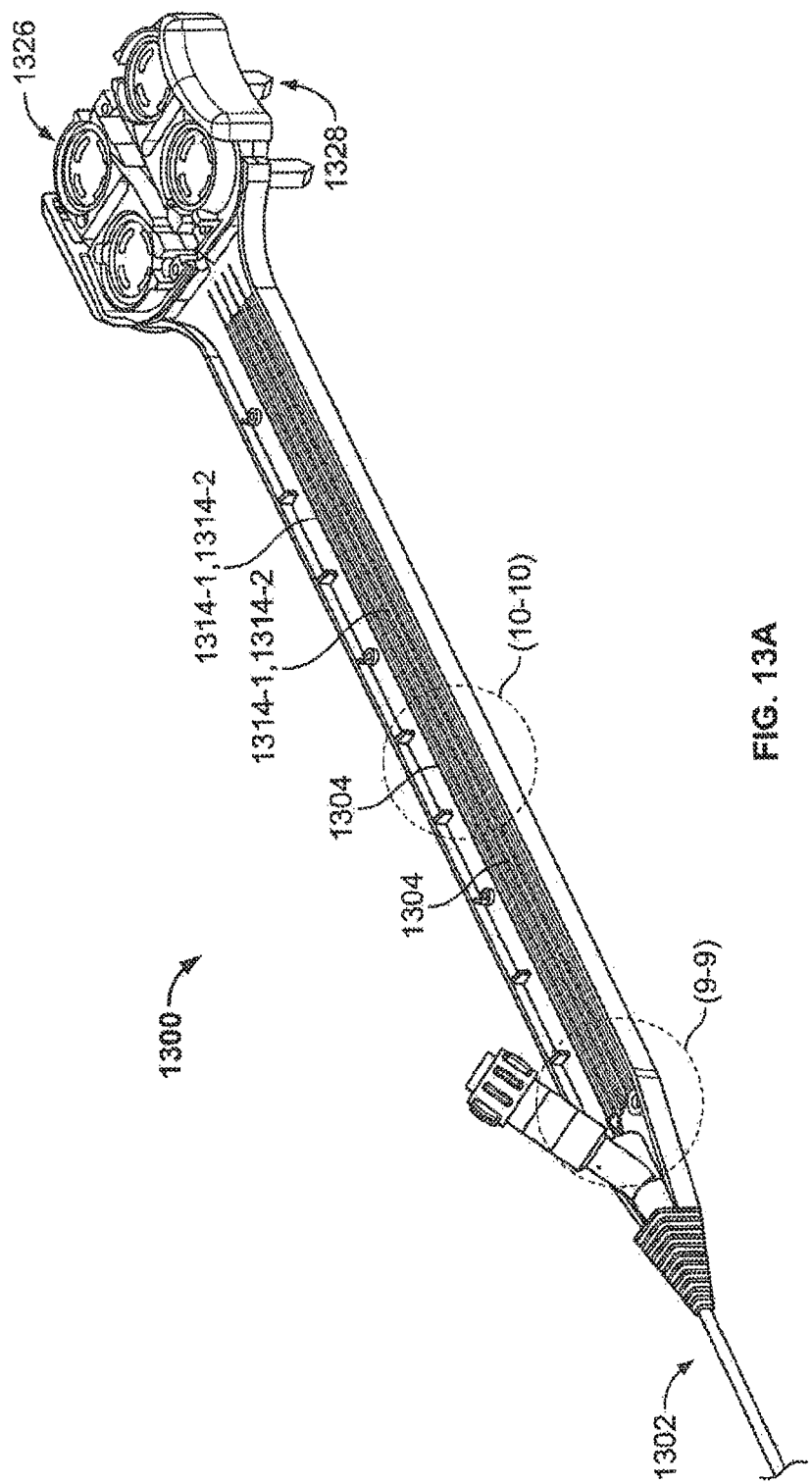
Figure 13B:
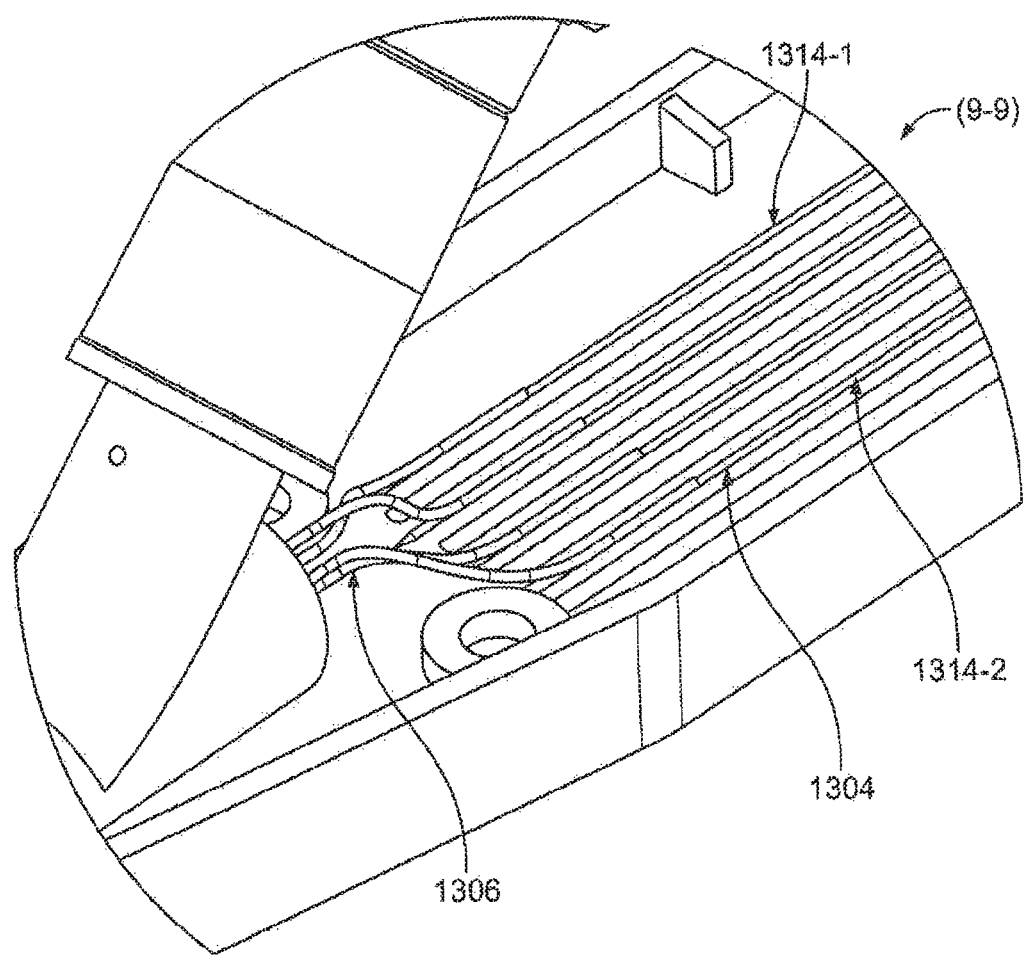
Figure 13C:
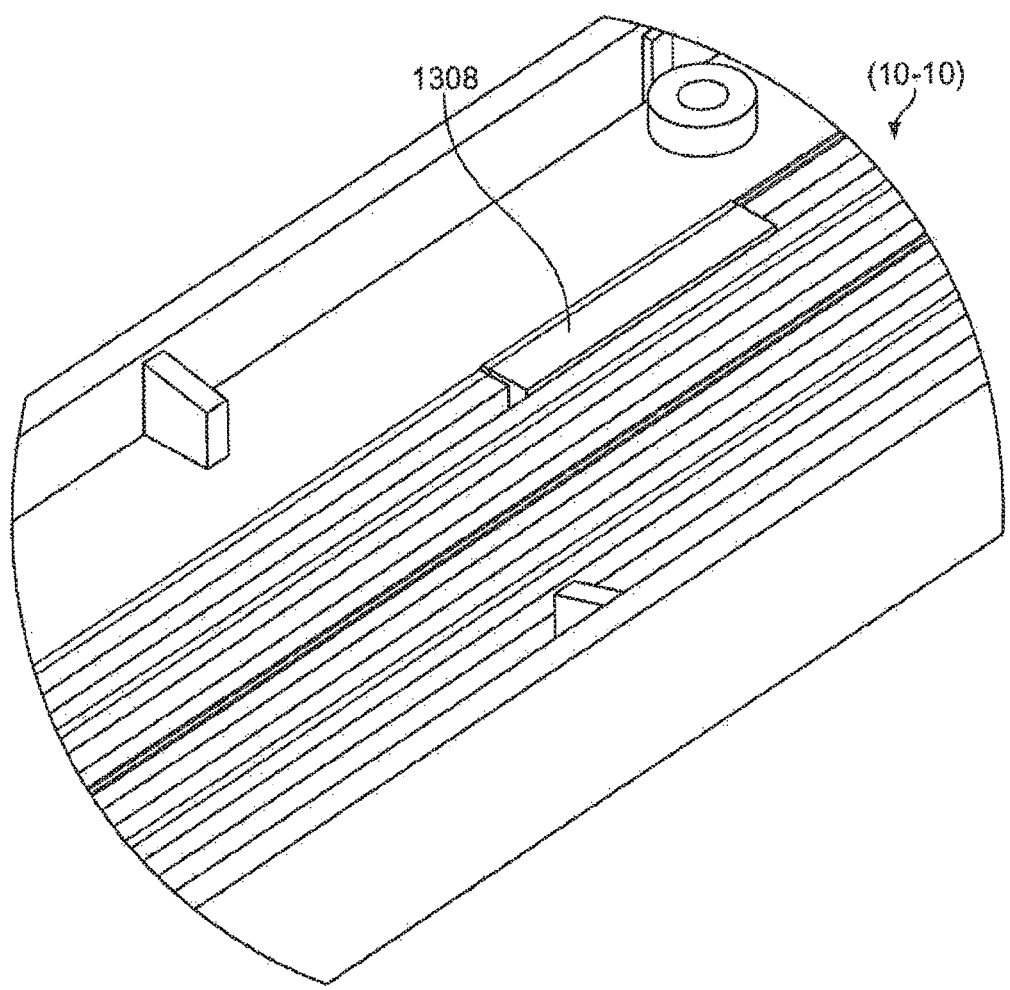
Figure 13E:
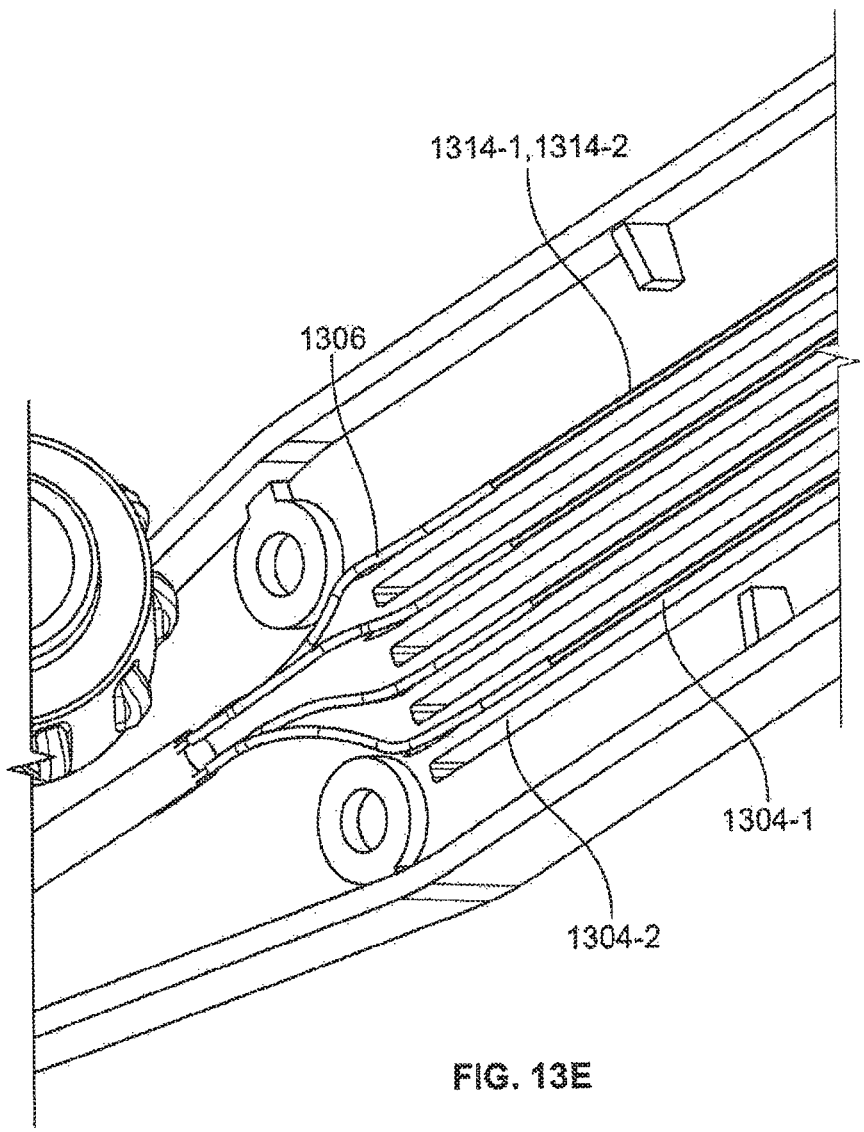

FIG. 13A through FIG. 13F illustrate one variation of a control unit or splayer configured to accommodate and operate multiple flex members, wherein the control unit may include active control components for selective operation or displacement of the flex members. FIG. 13A illustrates one variation of a control unit (1300) and an elongate instrument or catheter (1302) coupled to the control unit. The control unit (1300) includes interface grooves or channels (1304) where the flex tubes (1306), pull wires (1314-1), and anchor wires (1314-2) may be disposed. The control unit (1300) may also include drive pulleys (1326) and drive pins (1328) configured to operate pull wires and anchor wires. The drive pins (1328) may be operated by one or more drive mechanisms in the instrument driver (not shown). The drive pins (1328) may drive the drive pulleys (1326) to operate the pull wires (1314-1) and anchor wires (1314-2) to respectively steer or articulate the elongate instrument (1302) as well as drive or displace the flex tubes (1306). FIG. 13B illustrates a close up exposed detail view (View 9-9) of the control unit (1300) and some of its components and features, such as the interface grooves or channels (1304) where the flex tubes (1306) are disposed within the control unit. Furthermore, the control unit (1300) may also include interface slides (1308) which may be configured to drive or displace the flex tubes (1306) as illustrated in detail view (View 10-10) of FIG. 13C. The interface slide (1308) may be operated by a drive mechanism or an interface slide carriage (1310) located in the instrument driver (1316) of a robotic system, as illustrated in FIG. 13D. The interface slide carriage (1310) may be operated by a worm gear, a screw drive, a rail system or any suitable motion control system that allows the interface slide carriage to be moved or displaced, such that the interface slide may be displaced to act on the flex tubes (1306). FIG. 13E illustrates a further close-up detail view of the control unit (1300). This close-up detail view shows that the flex tubes (1306), pull wires (1314-1) and anchor wires (1314-2) are disposed in interface grooves or channels (1304-1), while interface grooves or channels (1304-2) may be used by the interface slides (1308) as guide tracks or guide channels for traversing up and down the length of the control unit to displace the flex tubes (1306). FIG. 13F illustrates the underside of the control unit (1300). As shown in this figure, the interface slides (1308) may be exposed through the interface grooves or channels (1304-1), such that the interface slides (1308) may be interfaced with the interface slide carriage (1310) in the instrument driver (1316).

Various Implementations of Flex Members

FIG. 14A through FIG. 14D illustrate various embodiments where flex tubes may be secured, placed, or positioned to obtain various variability of shape and/or curvature of an elongate instrument by way of active displacement of the flex tube members as previously described. In addition, the various embodiments, as illustrated in FIG. 14A through FIG. 14D may also be obtained or configured by way of fixedly coupling the distal portions of the flex tubes as provided by passively controlled or actively controlled flex tubes installations. FIG. 14A illustrates an initial state in which one or more flex tubes and their associated components of an elongate instrument (1400) may be displaced and/or secured to a first position or location (1400-1), e.g., by a deployable anchor or fixed coupling, along the length of the elongate instrument in accordance with one embodiment. In this example, the elongate instrument (1400) may have substantially two sections of variability (1402-1 and 1402-2) to steer and/or adjust the shape and/or curvature of the elongate instrument (1400). Section of variability may be described as a portion of the elongate instrument having particular characteristics of axial stiffness, flexibility, and pliability; lateral stiffness, flexibility, and pliability; bending stiffness, flexibility, and pliability, etc. FIG. 14B illustrates another embodiment in which one of a plurality of flex tubes and their associated components of an elongate instrument (1400) may be displaced and/or secured to a second position or location (1400-2) on the elongate instrument (1400), while one or more different flex tubes may be displaced and/or secured to a first position or location (1400-1) on the elongate instrument (1400). In this example, the elongate instrument (1400) may have substantially three sections of variability (1002-1, 1002-2, and 1002-3) to steer and/or adjust the shape and/or curvature of the elongate instrument (1400). FIG. 14C illustrates another embodiment in which one of a plurality of flex tubes and their associated component of an elongate instrument (1400) may be displaced and/or secured to a second position or location (1400-2) on the elongate instrument (1400), while a different flex tube may be displaced and/or secured to a third position or location (1400-3), and one or more of other flex tubes may be displaced and/or secured to a first position or location (1400-1) on the elongate instrument (1400). In this example, the elongate instrument may have substantially four sections of variability (1402-1, 1402-2, 1402-3, and 1402-4) to steer and/or adjust the shape and/or curvature of the elongate instrument (1400). FIG. 14D illustrates another embodiment in which one of a plurality of flex tubes and their associated components of an elongate instrument (1400) may be displaced arid/or secured to a fourth position or location (1400-4), while another one of a plurality of flex tubes may be displaced and/or secured to a second position or location (1400-2) on elongate instrument (1400), another different flex tube may be displaced and/or secured to a third position or location (1400-3), and another flex tubes may be displaced and/or secured to a first position or location (1400-1) on the elongate instrument (1400). In this example, the elongate instrument may have substantially five sections of variability (1402-1, 1402-2, 1402-3, 1402-4, and 1402-5) to steer and/or adjust the shape and/or curvature of the elongate instrument (1400). As described, the various embodiments illustrated in this example may be obtained by displacing the flex tubes through the application of displaceable control of the flex tubes or by fixedly coupling the distal portion of the flex tubes at the various locations along the length of the elongate instrument in actively control configurations or passively controlled configurations.

FIG. 15A through 115C illustrate a simplified construction of an elongate instrument (1500) with variable shape control and support in accordance with one embodiment. In this embodiment, the elongate instrument may be formed into a desired shape in a passive manner. That is instead of using pull wires to steer the elongate instrument (1500) into a desired shape or curvature, a separate shape or curvature forming instrument (1550) may be used to put the elongate instrument (1500) into a desired shape or curvature. The shape or curvature forming instrument (1550) may be a miniaturized instrument that when it is in its neutral state, it may be substantially flexible, pliable, and may conform to any shape or curvatures without significant resistance. As illustrated in FIG. 11A, the shape forming instrument (1550) in its neutral state may conform to the shape of the elongate instrument (1500). However, when it is activated, it may become erected or stiffened into a preprogrammed or pre-determined shape or curvature, as illustrated in FIG. 15B. The elongate instrument (1500) in its neutral state conforms to the shape or curvature of the shape forming instrument (1550). Once the desired shape or curvature is formed, flex tubes (1506-1 and 1506-2) may be locked in place to lock the elongate instrument (1500) into the desired shape or curvature, as illustrated in FIG. 15B. The shape forming instrument (1550) may then be deactivated, so that it may become substantially flexible and pliable again. In its deactivated or neutral state, the shape forming instrument (1550) may then be withdrawn from the elongate instrument (1500), as indicated by the arrow in FIG. 15C. As such, the flexible and steerable elongate instrument (1500) with variable shape control and support may be comprised of a simplified construction with one or more flex tubes and active control to lock the flex tube after the elongate instrument (1500) has acquired a desired shape or curvature. For illustrative purposes, this example describes a method of using two flex tubes to lock or maintain an elongate instrument in a particular desired shape or curvature. As may be appreciated, one or more flex tubes may be used to lock or maintain an elongate instrument in a particular desired shape or curvature. In addition, the flex tubes may be positioned or disposed in various locations, positions, or orientations within the wall or lumens of the elongate instrument to allow the flex tubes to lock or maintain the elongate instrument in various shapes, curvatures, or orientations.

Figure 16J:
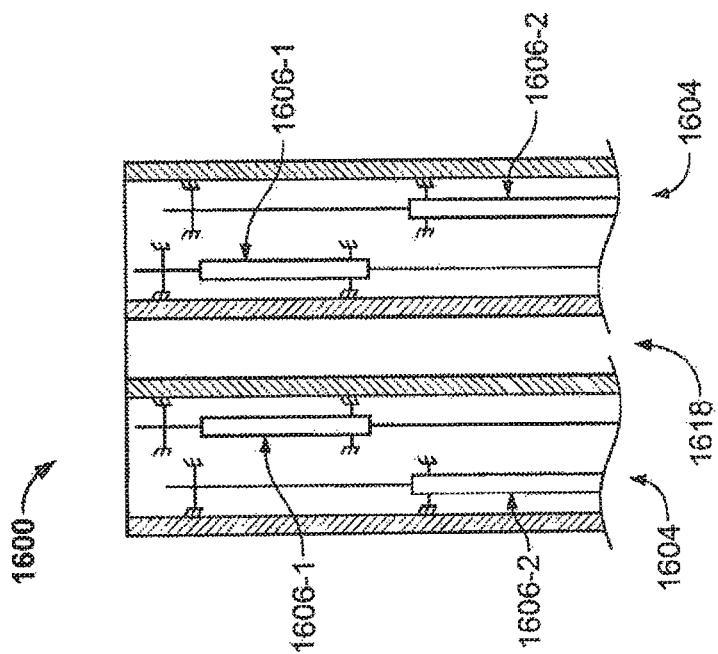
Figure 16I:
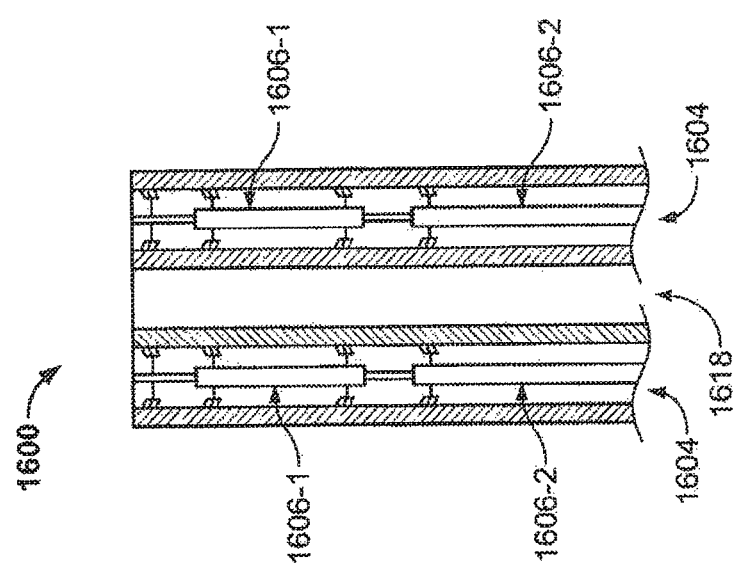

FIG. 16A through FIG. 16J illustrate various embodiments where flex tubes and associated components may be disposed within the wall or lumens of an elongate instrument to provide various variety of steering, articulation, shape, and curvature control to the elongate instrument. The flex tubes may be secured, placed, or positioned in the elongate instrument to obtain various variety or variability of steering, articulation, shape and/or curvature control of an elongate instrument by way of active displacement of the flex tube members as previously described in this disclosure. In addition, the various embodiments, as illustrated in FIG. 16A through FIG. 16J, may also be obtained or configured by way of fixedly coupling the distal portions of the flex tubes as described in this disclosure by way of passive control or active control configurations or installations of flex tubes and associated components. As illustrated in FIG. 16A through 16J, an elongate instrument or catheter (1600) may include an elongate body with a working lumen (1618) and one or more control lumens (1604) where control elements, such as flex tubes (1606), control wires (1614), and various associated components may be disposed. The embodiments as illustrated in FIG. 16A through 16J are for illustrative purposes only and not to limit the variety of possible configurations in which the flex tubes and associated components may be implemented to provide various means to steer and articulate the elongate instrument or to control the shape or curvature of the body of the elongate instrument. With that understanding, FIG. 16A through 16F illustrate a sample of variations in which one set of flex tubes (1606) may be configured or implemented in a set of control lumens (1604) within the body of an elongate instrument (1600). For example, the distal portion of the flex tubes (1606) and associated pull wires (1614) may be attached, coupled, or secured to any portion or location on the body of the elongate instrument (1600) to affect the stiffness and steering, articulation, and bending characteristics of the elongate instrument. For the configuration with active control of the flex tubes (1606), the implementation may also include push tubes or control members (1608) to displace the proximal portion of the flex tubes. FIG. 16G through FIG. 16J illustrate a sample of variations in which a plurality of flex tubes (1606) may be disposed or implemented in a control lumen (1604) of an elongate instrument (1600) to create various stiffness, and steering, articulation, and bending characteristics of the elongate instrument. FIG. 16G and FIG. 16H illustrate examples of a plurality of flex tubes (1606) configured in a substantially parallel configuration within a control lumen (1604) affect the stiffness and steering, articulation, and bending characteristics of the elongate instrument. The flex tubes (1606) may be configured or implemented by way of passively controlled, actively controlled, displaceable controlled configuration, or combination of passively controlled, actively controlled or displaceable controlled configuration. FIG. 16I and FIG. 16J illustrate a sample of variations in which one of the plurality of flex tubes (e.g., 1606-1) in a control lumen (1604) may be configured in a passively controlled manner, while one or more other flex tubes (160602) may be configured in a passively controlled manner, actively controlled manner, or displaceable controlled manner.

Various Methods of Application

Figure 17A:
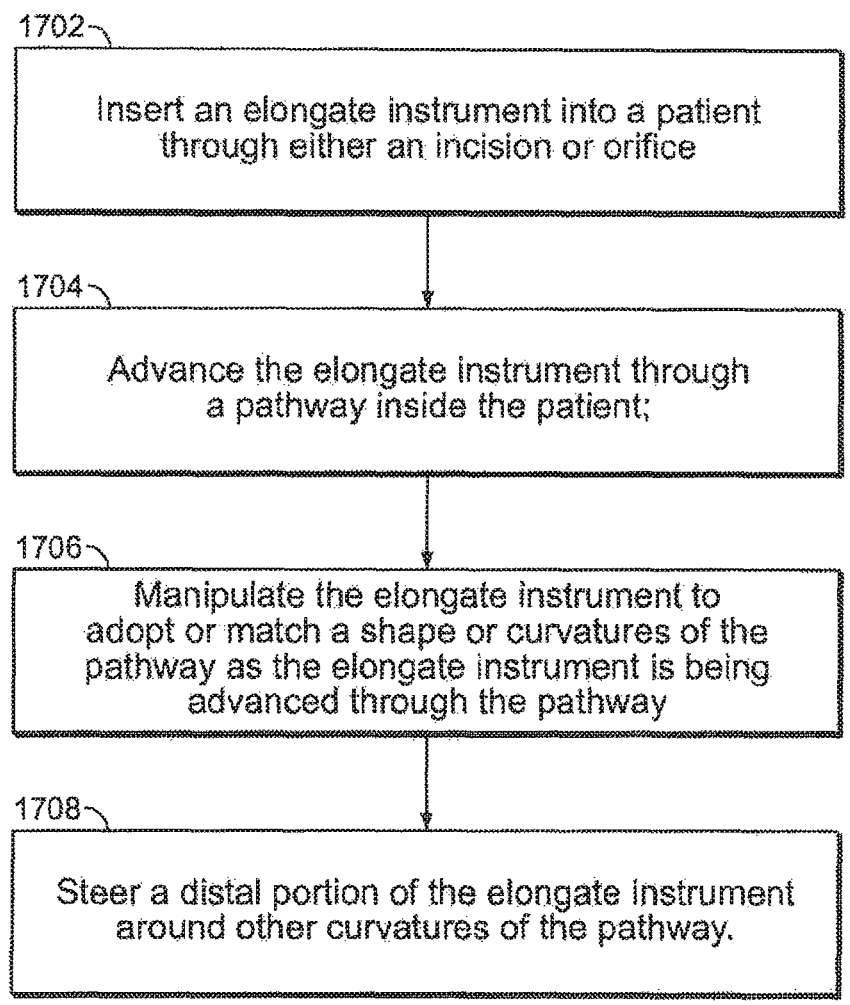
FIG. 17A through FIG. 17F illustrate various methods in which an elongate instrument with passive control, active control, or displaceable control may be used to approach and treat a target site or tissue structure in a minimally invasive procedure.
Figure 17B:
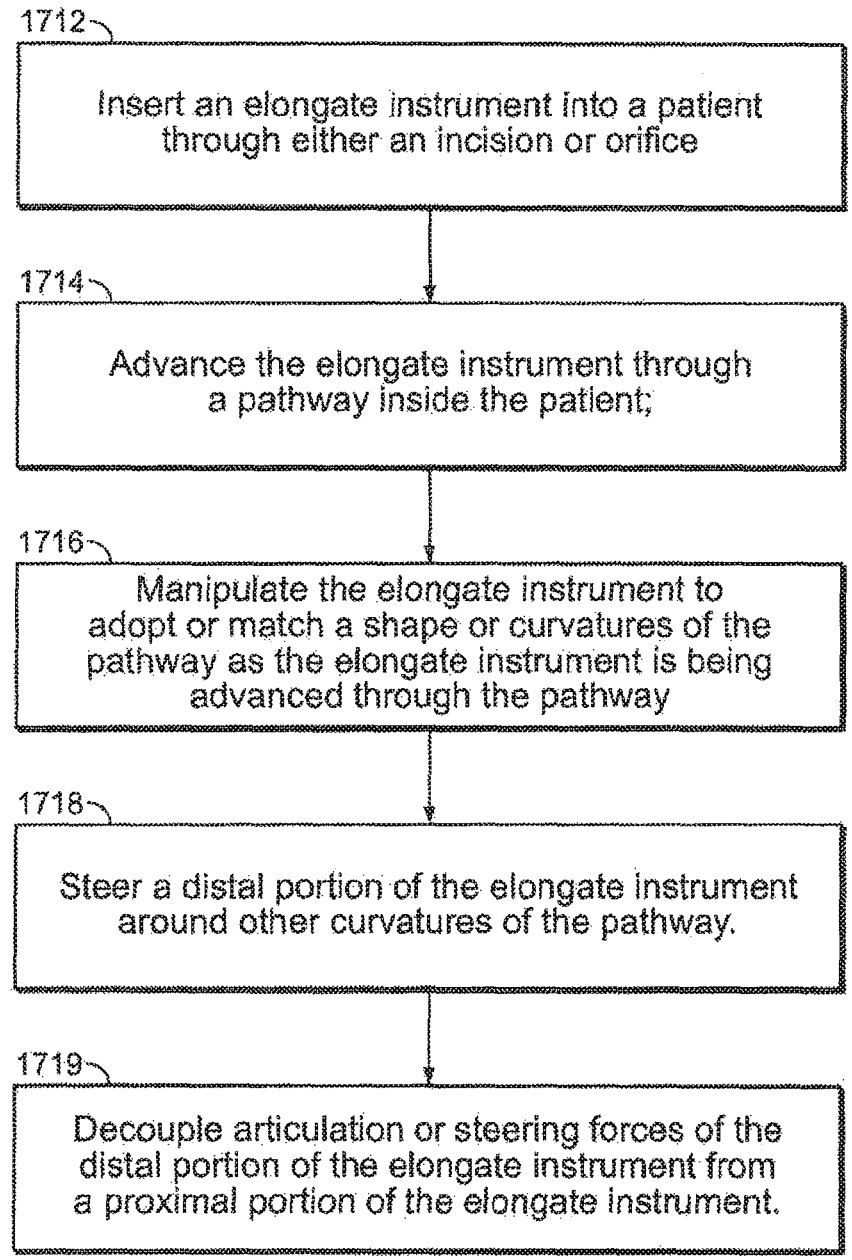
Figure 17C:
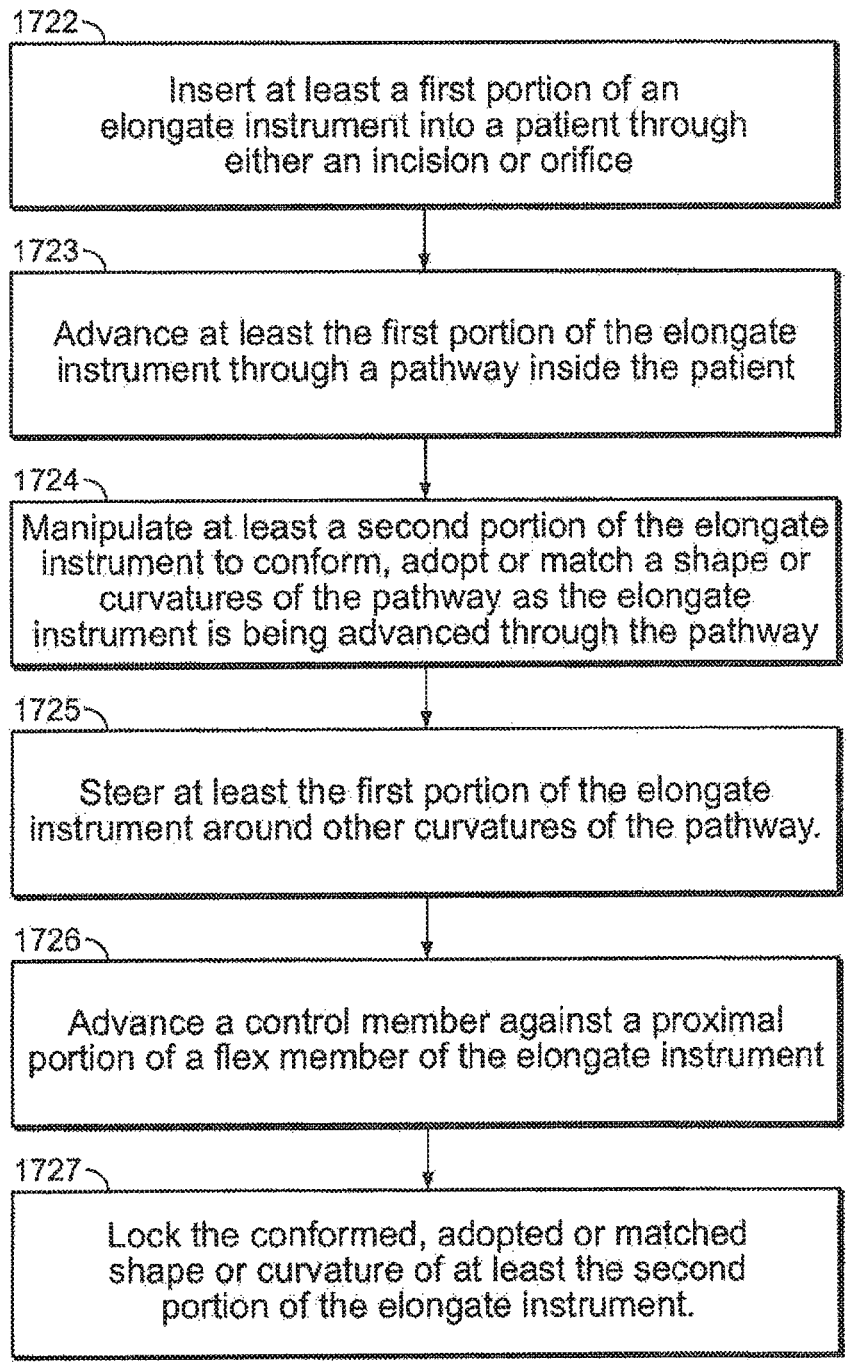
Figure 17D:
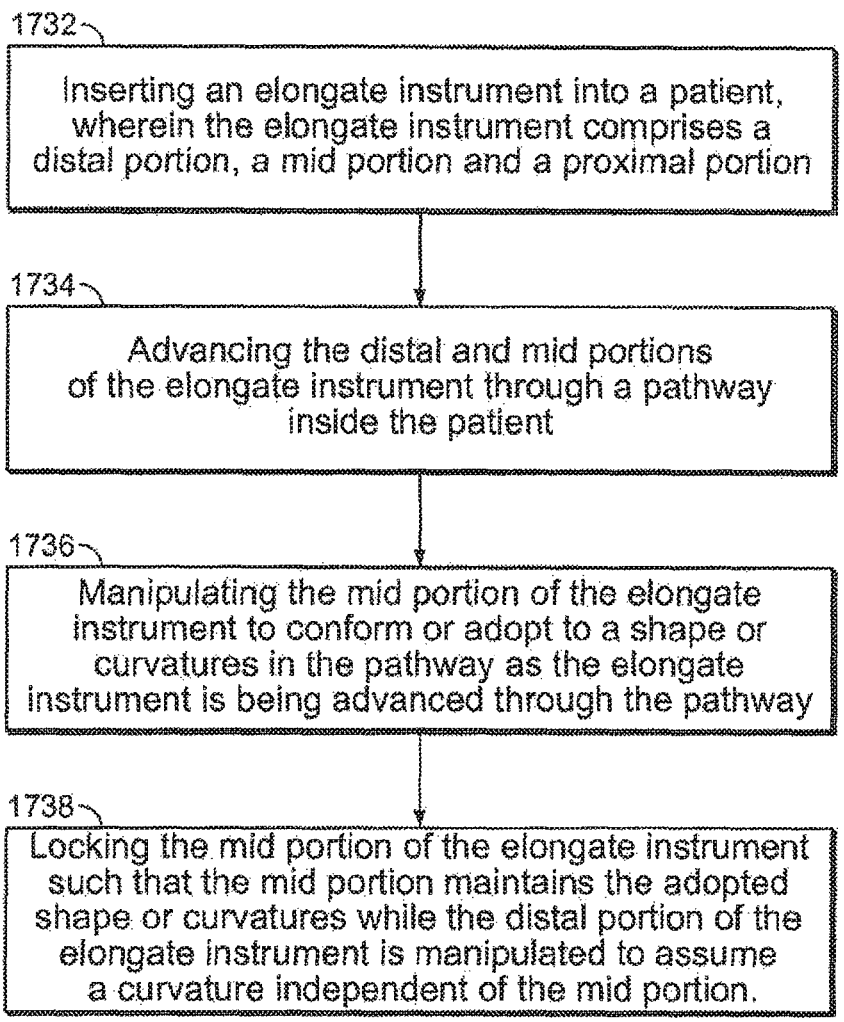
Figure 17E:
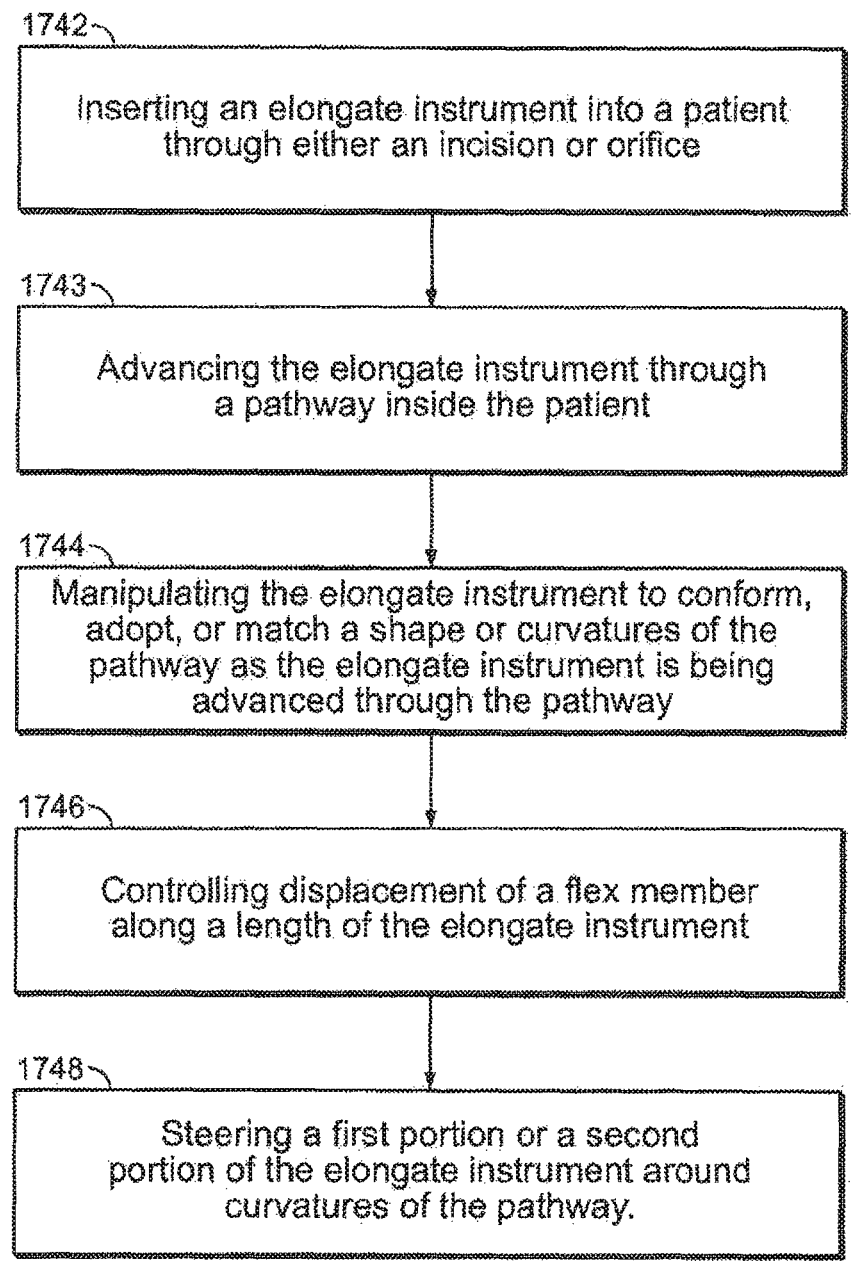
Figure 17F:
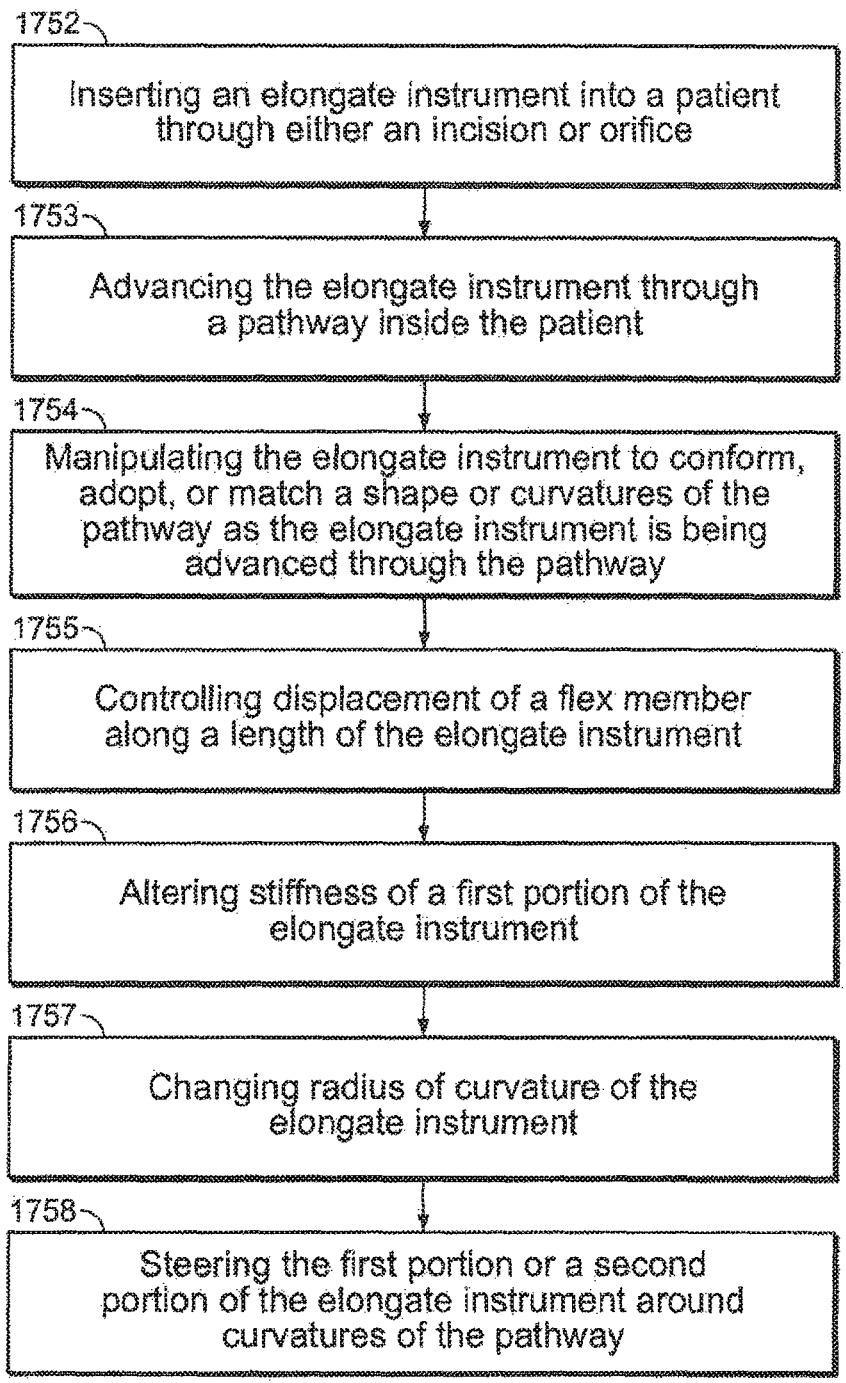

FIG. 17A through FIG. 17F illustrate various methods in which an elongate instrument with passive control, active control, or displaceable control may be used to approach and treat a target site or tissue structure in a minimally invasive procedure. In one method as FIG. 17A illustrates, at least a portion, e.g., a first portion or distal portion, of an elongate instrument may be inserted into a patient percutaneously through the skin either by way of an incision or orifice, as described in Step 1702. Advance at least a portion, e.g., first portion or distal portion, of the elongate instrument through a pathway inside the patient, as described in Step 1704. At least a portion, e.g., a second portion or proximal portion, of the elongate instrument may be manipulated to conform, adopt, or match a shape or curvature of the pathway as the elongate instrument is being advanced through the pathway, as described in Step 1706. Steer, or articulate at least a portion, e.g., first portion or distal portion, of the elongate instrument around other curvatures of the pathway as the elongate instrument is navigated through the anatomy of the patient, as described in Step 1708. In another method as FIG. 17B illustrates, at least a portion, e.g., a first portion or distal portion, of an elongate instrument may be inserted into a patient percutaneously through the skin either by way of an incision or orifice, as described in Step 1712. Advance at least a portion, e.g., first portion or distal portion, of the elongate instrument through a pathway inside the patient, as described in Step 1714. At least a portion, e.g., a second portion or proximal portion, of the elongate instrument may be manipulated to conform, adopt, or match a shape or curvature of the pathway as the elongate instrument is being advanced through the pathway, as described in Step 1716. At least a portion, e.g., first portion or distal portion, of the elongate instrument may be steered or articulated around other curvatures of the pathway as the elongate instrument is navigated through the anatomy of the patient, as described in Step 1718. In addition, articulation forces from steering the one portion, e.g., first portion or distal portion, of the elongate instrument may be decoupled from another portion, e.g., second portion or proximal portion, of the elongate instrument, as described in Step 1719. Furthermore, the conformed, adopted, or matched shape or curvature of the one portion, e.g., second portion or proximal portion, may be maintained by way of decoupling the one portion, e.g., first portion or distal portion, of the elongate instrument from another portion, e.g., second portion or proximal portion, of the elongate instrument. The act of decoupling the articulation or steering forces may include preventing a flex member from moving in reaction to the articulation or steering forces and compressing the flex member to support the articulating or steering forces. In another method as FIG. 17C illustrates, at least a portion, e.g., a first portion or distal portion, of an elongate instrument may be inserted into a patient percutaneously through the skin either by way of an incision or orifice, as described in Step 1722. Advance at least a portion, e.g., first portion or distal portion, of the elongate instrument through a pathway inside the patient, as described in Step 1723. At least a portion, e.g., a second portion or proximal portion, of the elongate instrument may be manipulated to conform, adopt, or match a shape or curvature of the pathway as the elongate instrument is being advanced through the pathway, as described in Step 1724. At least a portion, e.g., first portion or distal portion, of the elongate instrument may be steered or articulated around other curvatures of the pathway as the elongate instrument is navigated through the anatomy of the patient, as described in Step 1725. In addition, a control member may be advanced a control unit or splayer against a flex member or flex tube, as described in Step 1726, at the proximal portion of the flex member to hold the flex member at a particular position or orientation. As such, at least a portion, e.g., second portion or proximal portion, of the elongate instrument may be locked in the conformed, adopted or matched shape or curvature. In another method as FIG. 17D illustrates, an elongate instrument may be inserted into a patient percutaneously through the skin either by way of an incision or orifice, as shown in Step 1732. The elongate instrument may include a first portion, a second portion, and a third portion, or a distal portion, a mid portion, and a proximal portion. The first portion or distal portion and the second portion or mid portion of the elongate instrument may be advanced through a pathway inside the patient, as described in Step 1734. At least a portion, e.g., second portion or mid portion, of the elongate instrument may be manipulated to conform, adopt, or match a shape or curvatures of the pathway as the elongate instrument is being advanced through the pathway, as described in Step 1736. The second portion or mid portion of the elongate instrument may be locked in place to maintain the conformed, adopted, or matched shape or curvatures of the pathway while the first portion or distal portion of the elongate instrument may be manipulated to assume a curvature independent of the second portion or mid portion, as described in Step 1738. In another method as FIG. 17E illustrates, an elongate instrument may be inserted into a patient percutaneously through the skin either by way of an incision or orifice, as shown in Step 1742. The elongate instrument may include a first portion, a second portion, and a third portion, or a distal portion, a mid portion, and a proximal portion. The first portion or distal portion and the second portion or mid portion of the elongate instrument may be advanced through a pathway inside the patient, as described in Step 1743. At least a portion, e.g., second portion or mid portion, of the elongate instrument may be manipulated to conform, adopt, or match a shape or curvatures of the pathway as the elongate instrument is being advanced through the pathway, as described in Step 1744. Controlling the displacement of a flex member within the elongate instrument, wherein the flex member may be configured to assist with steering or articulation of the elongate instrument, as described in Step 1746. Steering a first portion or a second portion of the elongate instrument around curvatures of the pathway inside the patient, as described in Step 1748. In another method as FIG. 17F illustrates, an elongate instrument may be inserted into a patient percutaneously through the skin either by way of an incision or orifice, as shown in Step 1752. The elongate instrument may include a first portion, a second portion, and a third portion, or a distal portion, a mid portion, and a proximal portion. The first portion or distal portion and the second portion or mid portion of the elongate instrument may be advanced through a pathway inside the patient, as described in Step 1753. At least a portion, e.g., second portion or mid portion, of the elongate instrument may be manipulated to conform, adopt, or match a shape or curvatures of the pathway as the elongate instrument is being advanced through the pathway, as described in Step 1754. Controlling the displacement of a flex member along a length of the elongate instrument, wherein the flex member may be disposed within the elongate instrument and the flex member may be configured to assist with steering or articulation of the elongate instrument, as described in Step 1755. The stiffness of at least a portion, e.g., first portion or distal portion, of the elongate instrument may be altered by the displacement of the flex member, as described in Step 1756. In addition, the radius of curvature for a least a portion of the elongate instrument may be changed by the displacement of the flex member, as described in Step 1757. After altering the stiffness and/or radius of curvature of at least a portion of the elongate instrument, steer a portion, e.g., first portion or second portion, of the elongate instrument around curvatures of the pathway inside the patient, as described in Step 1758.

Multiple embodiments and variations of the various aspects of the invention have been disclosed and described herein. Many combinations and permutations of the disclosed system may be useful in minimally invasive medical intervention and diagnostic procedures, and the system may be configured to support various flexible robotic instruments. One of ordinary skill in the art having the benefit of this disclosure would appreciate that the foregoing illustrated and described embodiments of the invention may be modified or altered, and it should be understood that the invention generally, as well as the specific embodiments described herein, are not limited to the particular forms or methods disclosed, but also cover all modifications, equivalents and alternatives. Further, the various features and aspects of the illustrated embodiments may be incorporated into other embodiments, even if not so described herein, as will be apparent to those ordinary skilled in the art having the benefit of this disclosure. Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:
1. A steerable elongate instrument, comprising:
an elongate body, comprising:
a proximal portion;
a distal portion;
a first lumen extending through the proximal portion and the distal portion; and
multiple secondary lumens extending through the proximal portion and the distal portion;
multiple flex tubes disposed within the secondary lumens within the proximal portion of the elongate body, wherein a proximal portion of each flex tube is slideable into and out of the elongate body at a proximal end of the elongate body, wherein a distal end of each flex tube is fixedly coupled to a distal end of the proximal portion of the elongate body, and wherein, when the elongate body is placed in a bend such that a first side of the elongate body contracts and a second side of the elongate body stretches, one of the flex tubes located in the first side slides at least partially out of the secondary lumen in which it is disposed, and another of the flex tubes located in the second side slides at least partially into the secondary lumen in which it is disposed;
multiple pull wires, wherein each of the flex tubes has a different one of the pull wires disposed therein; and
a control unit positioned proximal to the elongate body, wherein a distal portion of each of the pull wires is coupled to the distal portion of the elongate body, and wherein a proximal portion of each of the pull wires is operatively coupled to the control unit.

2. The elongate instrument of claim 1, wherein the distal portion of each of the pull wires is coupled to the elongate body via a control ring fixedly coupled to the elongate body.

3. The elongate instrument of claim 1, further comprising multiple liners, wherein each of the liners is disposed within each of the secondary lumens between the secondary lumen and the flex tube and comprises a slidable surface for the flex tubes to slide within the secondary lumens.

4. The elongate instrument of claim 1, configured such that a tension applied to the pull wires via the control unit results in articulation of the distal portion of the elongate instrument.

5. The elongate instrument of claim 1, wherein each of the flex tubes is a coil tube.

6. The elongate instrument of claim 1, wherein each of the flex tubes is a ring.

7. The elongate instrument of claim 1, wherein each of the flex tubes is a spirally cut tube.

8. The elongate instrument of claim 1, wherein the flex tubes are configured to support articulation forces that steer the distal portion of the elongate body while decoupling the articulation forces from the proximal portion of the elongate body.

9. The elongate instrument of claim 1, wherein the flex tubes are configured to support articulation forces that steer the distal portion of the elongate body such that the proximal portion of the elongate body remains flexible while the articulation forces are applied.

10. The elongate instrument of claim 1, wherein a proximal end of each of the flex tubes is fixedly coupled to the control unit or other structural element such that outward sliding of one of the flex tubes from the elongate body forms a buffer loop that maintains a constant path length for the respective pull wire for accurate articulation as the elongate instrument is steered through a patient's anatomy.

11. The elongate instrument of claim 1, wherein the control unit is a splayer.

12. A steerable elongate instrument, comprising:
an elongate body, comprising:
a proximal portion;
a distal portion;
a first lumen extending through the proximal portion and the distal portion; and
a secondary lumen extending through the proximal portion and the distal portion;
a flex tube disposed within the secondary lumen within the proximal portion of the elongate body, wherein a proximal end of the flex tube is free to slide such that a proximal portion of the flex tube is slideable into and out of the elongate body at a proximal end of the elongate body, wherein a distal end of the flex tube is fixedly coupled to a distal end of the proximal portion of the elongate body, and wherein, when the elongate body is placed in a bend oriented such that the flex tube is positioned in a contracted side of the elongate body, the proximal portion of the flex tube slides at least partially out of the secondary lumen, and when the bend is oriented such that the flex tube is positioned in a stretched side of the elongate body, the proximal portion of the flex tube slides at least partially into the secondary lumen;
a pull wire disposed within the flex tube; and
a control unit positioned proximal to the elongate body, wherein a distal portion of the pull wire is coupled to the distal portion of the elongate body, and a proximal portion of the pull wire is operatively coupled to the control unit.

13. The elongate instrument of claim 12, wherein the distal portion of the pull wire is coupled to the elongate body via a control ring fixedly coupled to the elongate body.

14. The elongate instrument of claim 12, further comprising a liner disposed within the secondary lumen between the secondary lumen and the flex tube and comprising a slidable surface for the flex tube to slide within the secondary lumen.

15. The elongate instrument of claim 12, configured such that a tension applied to the pull wire via the control unit results in articulation of the distal portion of the elongate instrument.

16. The elongate instrument of claim 12, wherein the flex tube is configured to support an articulation force that steers the distal portion of the elongate body while decoupling the articulation force from the proximal portion of the elongate body.

17. The elongate instrument of claim 16, wherein the flex tube is configured to prevent compression of the proximal portion of the elongate body from the articulation forces while maintaining flexibility of the distal portion of the elongate body.

18. The elongate instrument of claim 12, wherein the proximal end of the flex tube is fixedly coupled to the control unit or other structural element such that outward sliding of the flex tube from the elongate body forms a buffer loop that maintains a constant path length for the pull wire for accurate articulation as the elongate instrument is steered through a patient's anatomy.

19. The elongate instrument of claim 12, wherein the control unit is a splayer.

20. The elongate instrument of claim 12, wherein the flex tube is selected from the group consisting of a coil tube, a ring tube, and a spirally cut tube.

* * * * *